US009657322B2

(12) United States Patent
Dijkhuizen et al.

(10) Patent No.: US 9,657,322 B2
(45) Date of Patent: May 23, 2017

(54) GLUCOOLIGOSACCHARIDES COMPRISING (ALPHA 1->4) AND (ALPHA 1->6) GLYCOSIDIC BONDS, USE THEREOF, AND METHODS FOR PROVIDING THEM

(75) Inventors: Lubbert Dijkhuizen, Zuidlaren (NL); Marc Jos Elise Cornelis van der Maarel, Haren (NL); Johannis Paulus Kamerling, Linschoten (NL); Reinder Johannes Leemhuis, Groningen (NL); Slavko Kralj, Oegstgeest (NL); Justyna Malgorzata Dobruchowska, Groningen (NL)

(73) Assignee: RIJKSUNIVERSITEIT GRONINGEN, CP Groningen (NL)

( * ) Notice: Subject to any disclaimer, the term of this patent is extended or adjusted under 35 U.S.C. 154(b) by 884 days.

(21) Appl. No.: 13/319,237

(22) PCT Filed: May 10, 2010

(86) PCT No.: PCT/NL2010/050269
§ 371 (c)(1),
(2), (4) Date: Jan. 24, 2012

(87) PCT Pub. No.: WO2010/128859
PCT Pub. Date: Nov. 11, 2010

(65) Prior Publication Data
US 2012/0165290 A1  Jun. 28, 2012

Related U.S. Application Data

(60) Provisional application No. 61/181,315, filed on May 27, 2009.

(30) Foreign Application Priority Data

May 8, 2009  (EP) ..................... 09159825

(51) Int. Cl.
C12P 19/04 (2006.01)
C12P 19/00 (2006.01)
C12N 9/10 (2006.01)

(52) U.S. Cl.
CPC ............... *C12P 19/00* (2013.01); *C12P 19/04* (2013.01); *C12N 9/1051* (2013.01); *C12Y 204/01005* (2013.01)

(58) Field of Classification Search
CPC ........ C12P 19/00; C12P 19/04; C12N 9/1051; C12Y 204/01005
See application file for complete search history.

(56) References Cited

U.S. PATENT DOCUMENTS 6,004,790 A * 12/1999 Dijkhuizen et al. .......... 435/193
2002/0042120 A1* 4/2002 Andersen et al. ............ 435/221
(Continued)

FOREIGN PATENT DOCUMENTS

JP      03187390       8/1991
JP      5-236982       9/1993
(Continued)

OTHER PUBLICATIONS

Imanaka, T., et al., 1989, "Pattern of action of Bacillus stearothermophilus neopullulanase on pullullan", Journal of Bacteriology, vol. 171, No. 1, pp. 369-374.*
(Continued)

*Primary Examiner* — Karen Carlson
(74) *Attorney, Agent, or Firm* — Hoffmann & Baron, LLP

(57) ABSTRACT

The invention relates to the field of poly-and oligosaccharides and their nutritional effects. In particular, it relates to the application of α-glucanotransferases in methods for preparing dietary fibers, including prebiotic oligosaccharides, and to novel oligosaccharides obtainable thereby. Provided is a method for producing a mixture of gluco-
(Continued)

Figure 2:
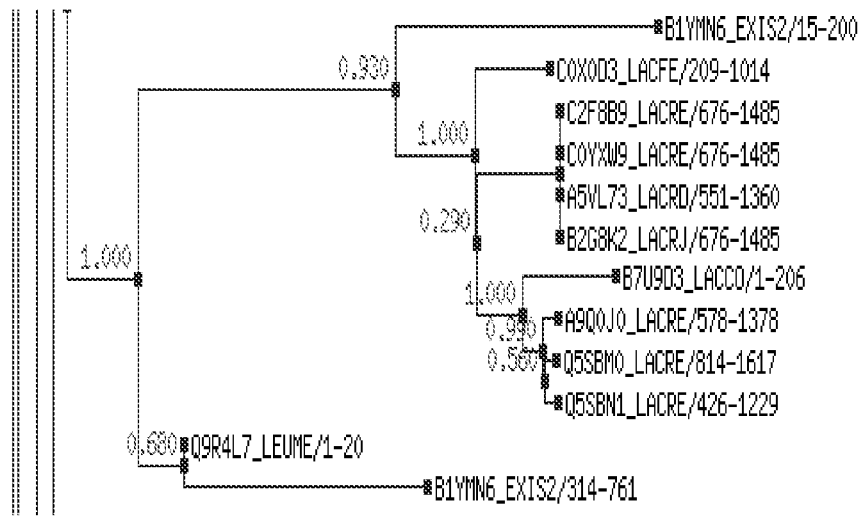

oligosaccharides having one or more consecutive (α1→6) glucosidic linkages and one or more consecutive (α1→4) glucosidic linkages, comprising contacting a poly- and/or oligosaccharide substrate comprising at least two (α1→4) linked D-glucose units with an α-glucanotransferase capable of cleaving (α1→4) glucosidic linkages and making new (α1→4) and (α1→6) glucosidic linkages. Also provided are (isolated) gluco-oligosaccharides obtainable thereby, and their application in nutritional and cosmetic compositions.

17 Claims, 8 Drawing Sheets

(56) References Cited

U.S. PATENT DOCUMENTS

| | | | |
|---|---|---|---|
| 2002/0155568 A1* | 10/2002 | Van Geel-Schutten et al. | 435/193 |
| 2004/0161835 A1 | 8/2004 | Kubota et al. | |
| 2004/0259213 A1* | 12/2004 | Van Geel-Schutten et al. | 435/101 |
| 2009/0022872 A1 | 1/2009 | Nishimoto et al. | |
| 2010/0120710 A1 | 5/2010 | Watanabe et al. | |
| 2010/0317065 A1* | 12/2010 | Van Der Kaaij et al. | 435/97 |
| 2011/0020496 A1 | 1/2011 | Shimada et al. | |
| 2012/0165290 A1* | 6/2012 | Dijkhuizen et al. | 514/54 |

FOREIGN PATENT DOCUMENTS

| | | |
|---|---|---|
| JP | 08023990 | 1/1996 |
| JP | 2001-258589 | 9/2001 |
| JP | 2006312705 A | 11/2006 |
| JP | 20100095701 A | 4/2010 |
| KR | WO/2008/093911 A1 | 8/2008 |
| WO | 2008136331 A1 | 11/2008 |
| WO | 2009113652 A1 | 9/2009 |

OTHER PUBLICATIONS

Takata, H., et al., 1992, "Action of neopullulanase: Neopullulanase catalyzes both hydrolysis and transglycosylation at (α1→4) and (α1→6) glucosidic linkages", The Journal of Biological Chemistry, vol. 267, No. 26,pp. 18447-18452.*
Kuriki, T., et al., 1993, "Highly branched oligosaccharides produced by the transglycosylation reaction of neopullulanase", Journal of Fermentation Bioengneering, vol. 76, No. 1, pp. 184-190.*
Fujii, K., et al., 2003, "Bioengineering and application of novel glucose polymers", Biocatalysis and Biotransformation, vol. 21, No. 1, pp. 1676-172.*
Kralj, S., et al., 2005, "Rational transformation of Lactobacillus reuteri 121 reuteransucrase into a dextransucrase", Biochemistry, vol. 44, No. 25, pp. 9206-9216.*
Kuriki, T., et al., 2006, "The concept of the α-amylase family: a rational tool for interconverting glucanohydrolases—glucanotransferases, and their specificities", Journal of Applied Glycoscience, vol. 53, No. 2, pp. 155-161.*
Van der Kaaij, R.M., et al., 2007, "Two novel, putatively cell wall-associated and glycosylphosphatidylinositol-anchored α-glucanotransferase enzymes of Aspergillus niger", Eukaryotic Cell, vol. 6, No. 7, pp. 1178-1188.*
Hellmuth, H., 2008, et al., "Engineering the glucansucrase GTFR enzyme reaction and glycosidic bond specificity: Toward tailor-made polymer and oligosaccharide products", Biochemistry, vol. 47, No. 25, pp. 6678-6684.*
Kralj, S., et al., 2011, "4,6-alpha-glucanotransferase, a novel enzyme that structurally and functionally provides an evolutionary link between glycoside hydrolase enzyme families 13 and 70", Applied and Environmental Microbiology, vol. 77, No. 22, pp. 8154-8163.*

Gibson, et al.—Dietary Modulation of the Human Colonic Microbiota: Updating the Concept of Prebiotics—Nutrition Research Reviews—(2004), 17, 259-275.
Helmuth, et al.—Engineering the Glucansucrase GTFR Enzyme Reaction and Glycosidic Bond Specificity: Toward Tailor-Made Polymer and Oligosaccharide Products—Biochemistry (2008) 47, 6678-6684.
Swistowska, et al.—Identification of Structural Determinants for Substrate Binding and Turnover by Glucosyltransferase R Supports the Permutation Hypothesis—FEBS Letters, (2007) 518, 4036-4042.
Sequence Listing—GH70 sequences from PFAM database, downloaded on Mar. 27, 2012.
Arguello-Morales, et al.—Sequence Analysis of the Gene Encoding Alternansucrase, a Sucrose Glucosyltransferase from Leuconostoc Mesenteroides NRRL B-1355—(2000) FEMS Microbiology Letters 182, 81-85.
Barends, et al.—Three-way Stabilization of the Covalent Intermediate in Amylomaltase, an a-Amylase-like Transglycosylase—(2007) J. Biol. Chem. 282, 17242-17249.
Fabre, et al.—Role of the Two Catalytic Domains of DSR-E Dextransucrase and Their Involvement in the Formation of Highly a-1,2 Branched Dextran—(2005) J. Bacteriol. 187, 296-303.
Van Geel-Schutten, et al.—Biochemical and Structural Characterization of the Glucan and Fructan Exopolysaccharides Synthesized by the Lactobacillus reuteri Wild-Type Strain and by Mutant Strains—(1999) Appl. Environ. Microbiol. 65, 3008-3014.
Hard, et al.—The Asn-linked Carbohydrate Chains of Human Tamm-Horsfall Glycoprotein of One Male—(1992). Eur. J. Biochem. 209, 895-915.
Hondoh, et al.—Three-dimensional Structure and Substrate Binding of Bacillus stearothermophilus Neopullulanase—(2003) J. Mol. Biol. 326, 177-188.
Van Hijum, et al.—Structure-Function Relationships of Glucansucrase and Fructansucrase Enzymes from Lactic Acid Bacteria—(2006). Microbiol. Mol. Biol. Rev. 70, 157-176.
Kaditzky, et al.—Influence of pH on the Formation of Glucan by Lactobacillus reuteri TMW 1.106 Exerting a Protective Function Against Extreme pH Values—(2008) Food Biotechnol. 22[4], 398-418.
Kralj, et al.—Molecular Characterization of a Novel Glucosyltransferase from Lactobacillus reuteri Strain 121 Synthesizing a Unique, Highly Branched Glucan with a-(1->4) and a-(1->6) Glucosidic Bonds—(2002) Appl. Environ. Microbiol. 68, 4283-4291.
Kralj, et al.—Efficient Screening Methods for Glucosyltransferase Genes in Lactobacillus Strains—(2003). Biocatal. Biotransform. 21, 181-187.
Kralj, et al.—Glucan Synthesis in the Genus Lactobacillus: Isolation and Characterization of Glucansucrase Genes, Enzymes and Glucan Products from Six Different Strains—(2004) Microbiology 150, 3681-3690.
Kralj, et al.—Highly Hydrolytic Reuteransucrase from Probiotic Lactobacillus reuteri Strain ATCC 55730—(2005) Appl. Environ. Microbiol. 71, 3942-3950.
Van Leeuwen, et al.—Structural Analysis of the a-D-glucan (EPS180) Produced by the Lactobacillus reuteri Strain 180 Glucansucrase GTF180 Enzyme—(2008) Carbohydr. Res. 343, 1237-1250.
Van Leeuwen, et al.—Structural Analysis of the a-D-glucan (EPS35-5) Produced by the Lactobacillus reuteri Strain 35-5 Glucansucrase GTFA Enzyme—(2008) Carbohydr. Res. 343, 1251-1265.
Linden, et al.—Differential Regulation of a Hyperthermophilic a-Amylase with a Novel (Ca,Zn) Two-metal Center by Zinc—(2003). J. Biol. Chem. 278, 9875-9884.
MacGregor, et al.—A Circularly Permuted a-amylase-type a/B-barrel Structure in Glucan-Synthesizing Glucosyltransferases—(1996) FEBS Lett. 378, 263-266.
MacGregor, et al.—Relationship of Sequence and Structure to Specificity in the a-amylase Family of Enzymes—(2001) Biochim. Biophys. Acta 1546, 1-20.

(56) References Cited

OTHER PUBLICATIONS

Monchois, et al.—Glucansucrases: Mechanism of Action and Structure-Function Relationships—(1999) FEMS Microbiol. Rev. 23, 131-151.
Moore, et al.—Arrangements in the Modular Evolution of Proteins—(2008). Trends Biochem. Sci. 33, 444-451.
Peisajovich, et al.—Evolution of New Protein Topologies Through Multistep Gene Rearrangements—(2006) Nat. Genet. 38, 168-174.
Pijning, et al.—Biochemical and Crystallographic Characterization of Glucansucrase from Lactobacillus reuteri 180—(2008). Biocatal. Biotransform. 26, 12-17.
Przylas, et al.—Crystal Structure of Amylomaltase from Thermus aquaticus, a Glycosyltransferase Catalysing the Production of Large Cyclic Glucans—(2000) J. Mol. Biol. 296, 873-886.
Rondeau-Mouro, et al.—High Resolution Solid-State NMR of B-Type Amylose—(2006) Biomacromolecules. 7, 2455-2460.
Sarkar, et al.—The "Megaprimer" Method of Site-Directed Mutagenesis—(1990). Biotechniques 8, 404-407.
Stam, et al.—Dividing the Large Glycoside Hydrolase Family 13 into Subfamilies: Towards Improved Functional Annotations of a-amylase-related Proteins—(2006) Protein Eng Des Sel. 19, 555-562.
Tokuriki, et al.—Protein Dynamism and Evolvability—(2009). Science. 324, 203-207.
Uitdehaag, et al.—X-ray Structures Along the Reaction Pathway of Cyclodextrin Glycosyltransferase Elucidate Catalysis in the a-amylase Family—(1999) Nat. Struct. Biol. 6, 432-436.
Vuijcic-Zagar, A.—Structural and Functional Investigations of Lactobacillus reuteri Glucansucrase . . . with crystallographic studies on an a-amylase and a prolyl endoprotease from Aspergillus niger—(2007) University of Groningen. PhD Thesis/Dissertation.
http://www.cazy.org.—CAZy-GH70 Family—Glycoside Hydrolase Family 70, ( 2012 download from database).
Kralj, et al.—Rational Transformation of Lactobacillus reuteri 121 Reuteransucrase into a Dextransucrase—(2005) Biochemistry, 44, 9206-9216.
Kralj, et al.—Role of Asparagine 1134 in Glucosidic Bond and Transglycosylation Specificity of Reuteransucrase from Lactobacillus reuteri 121—(2006) FEBS J. 273, 3735-3742.

Tamura, et al.—(2007) MEGA4: Molecular Evolutionary Genetics Analysis (MEGA) Software Version 4.0. Molecular Biology and Evolution 24: 1596-1599.
Van Leeuwen, et al.—Development of a 1H NMR structural-reporter-group concept for the primary structural characterisation of α-d-glucans—Carbohydrate Research—(2008) Carbohyd. Res., vol. 343, 1114-1119.
Kralj, et al.—Biochemical and Molecular Characterization of Lactobacillus reuteri 121 Reuteransucrace—(2004) Microbiology 150, 2099-2112.
Kralj, et al.—Hybrid reuteransucrase enzymes reveal regions important for glucosidic linkage specificity and the transglucosylation/hydrolysis ratio—(2008) FEBS Journal 275, 6002-6010.
Kelly, et al.—Starch and a-glucan acting enzymes, modulating their properties by directed evolution—(2009). J. Biotechnol. 140, 184-193.
Kamerling, et al.—Mass Spectrometry. In Clinical Biochemistry—Principles, Methods, Applications. (Lawson,A.M., ed), (1989), pp. 176-263. Walter de Gruyter, Berlin.
Kralj et al., "Molecular Characterization of a Novel Glucosyltransferase from Lactobacillus reuteri Strain 121 Synthesizing a Unique, Highly Branched Glucan with α-(1→4) and α-(1→6) Glucosidic Bonds", Applied and Environmental Microbiology, vol. 68, No. 9, pp. 4283-4291; 2002.
Takaha et al., "Disproportionating Enzyme (4-α-Glucanotransferase; EC 2.4.1.25) of Potato: Purification, Molecular Cloning, and Potential Role in Starch Metabolism", The Journal of Biological Chemistry, vol. 268, No. 2, pp. 1391-1396; 1993.
Borovsky et al., "Purification and Properties of Potato 1, 4-α-D-Glucan 6-α-(1,4-α-Glucano)-Transferase: Evidence Against a Dual Catalytic Function in Amylose-Branching Enzyme", Eur. J. Biochem. vol. 59, pp. 615-625; 1975.
Kralj et al., "Efficient Screening Methods for Glucosyltransferase Genes in Lactobacillus Strains", Biocatalysts and Biotransformation, vol. 21, No. 4-5, pp. 181-187; 2003.
Yamamoto et al., "Detailed Mechanism of Dextrin Dextranase from Acetobacter capsulatus ATCC 11894", Biosci. Biotech, Biochem, vol. 57, No. 1, pp. 47-50, 1993.

\* cited by examiner

Figure 1

| Bacterial Strain | Enzyme | II | III | IV | I |
|---|---|---|---|---|---|
| A | | 1 2 *1019* | 3 *1055* | 4 5 *1128* | 6 7 |
| Lb. reuteri 121 | GTFB | FDGFRVDAADNIDADVLDQ | HLSYNEGYHSGAA | WSFVTNHDQR-KNLI | GLKVQEDIVMNQ |
| Lb. reuteri TMW 1.106 | GTF106B | FDGFRVDAADNIDADVLDQ | HLSYNEGYHSGAA | WSFVTNHDQR-KNLI | GLKVQEDIVMNQ |
| Lb. reuteri ML1 | GTFML4 | FDGFRVDAADNIDADVLDQ | HLSYNEGYHSGAA | WSFVTNHDQR-KNLI | GLKVQEDIVMNQ |
| Lb. reuteri DSM 20016^ | GTFDSM | FDGFRVDAADNIDADVLDQ | HLVYNEGYHSGAA | WSFVTNHDQR-KNVI | GLKVQEDLVMNQ |
| | | *1015* | *1053* | *1125* | *1484* |
| B | | | | | |
| Ln. mesenteroides NRRL B-1299 | DSRE CD2 | FDSIRIDAVDFIHNDTIQR | HISLVEAGLDAGT | YSIIHAHDKGVQEKV | NMQVMADVVDNQ |
| Ln. mesenteroides ATCC 8293 | DSRP CD2 | FDSIRIDAVDFIDNDAIQR | HISLVEAGLDAGT | YSIIHAHDKGIQEKV | NMQVMADVVDNQ |
| C | | | | | |
| Lb. reuteri 121 | GTFA | FDSVRVDAPDNIDADLMNI | HINILEDWNHADP | YSFVRAHDNNSQDQI | GLQVMADWVPDQ |
| Lb. reuteri TMW 1.106 | GTFA106 | FDSIRVDAVDNVDADLLNI | HLNILEDWSHADP | YTFIRAHDSNAQDQI | GLQVMADWVPDQ |
| Lb. reuteri ATCC 55370 | GTFO | FDSVRVDAPDNIDADLMNI | HINILEDWNSSDP | YSFIRAHDNNSQDQI | GLQVMADWVPDQ |
| Lb. reuteri 180 | GTF180 | FDGIRVDAVDNVDVDLLSI | HINILEDWGWDDP | YNFVRAHDSNAQDQI | GLQAIADWVPDQ |
| Lb. reuteri ML1 | GTFML1 | FDSIRVDAVDNVDADLLDI | HINILEDWGGQDP | YSFIRAHDNGSQDDI | GIQAMADWVPDQ |
| Lb. parabuchneri 33 | GTF33 | FDGYRVDAVDNVDADLLNI | HLSILEDWDNNDP | YTFIRAHDSEVQTII | GIQAIDDWVPDQ |
| Lb. sakei Kg15 | GTFKg15 | FDSVRVDAVDNVDADLLNI | HLSILEDWGHNDP | YSFVRAHDSEVQTVI | GIQVMADFVPDQ |
| Lb. fermentum Kg3 | GTFKg3 | FDAIRIDAVDNVDADLLQL | HLSILEDWSHNDP | YSFVRAHDSEVQTVI | GMQVMADFVPDQ |
| Ln. mesenteroides NRRL B-1299 | DSRE CD1 | FDGYRVDAVDNVDADLLQI | HISILEDWDNNDS | YAFIRAHDSEVQTVI | GIQAINDWVPDQ |
| Ln. mesenteroides ATCC 8293 | DSRP CD1 | FDGYRVDAVDNVNADLLQI | HISILEDWDNNDP | YSFIRAHDSEVQTVI | GIQAINDWVPDQ |

A    B

A  B

A    -(1→4)-α-D-Glcp-(1→4)-
B    α-D-Glcp-(1→4)-
C    -(1→6)-α-D-Glcp-(1→4)-
D    -(1→6)-α-D-Glcp-(1→6)-
E    -(1→4)-α-D-Glcp-(1→6)-
F    α-D-Glcp-(1→6)-
Rα/β -(1→6)-D-Glcp
Rα/β -(1→4)-D-Glcp

SEQUENCE LISTING

```
<160> NUMBER OF SEQ ID NOS: 68

<210> SEQ ID NO 1
<211> LENGTH: 19
<212> TYPE: PRT
<213> ORGANISM: Artificial
<220> FEATURE:
<223> OTHER INFORMATION: GTF conserved region II

<400> SEQUENCE: 1

Phe Asp Gly Phe Arg Val Asp Ala Ala Asp Asn Ile Asp Ala Asp Val
1               5                   10                  15

Leu Asp Gln

<210> SEQ ID NO 2
<211> LENGTH: 13
<212> TYPE: PRT
<213> ORGANISM: Artificial
<220> FEATURE:
<223> OTHER INFORMATION: GTF conserved region III
<220> FEATURE:
<221> NAME/KEY: VARIANT
<222> LOCATION: (3)..(3)
<223> OTHER INFORMATION: May be V
```

```
<400> SEQUENCE: 2

His Leu Ser Tyr Asn Glu Gly Tyr His Ser Gly Ala Ala
1               5                   10

<210> SEQ ID NO 3
<211> LENGTH: 14
<212> TYPE: PRT
<213> ORGANISM: Artificial
<220> FEATURE:
<223> OTHER INFORMATION: GTF conserved region IV
<220> FEATURE:
<221> NAME/KEY: VARIANT
<222> LOCATION: (13)..(13)
<223> OTHER INFORMATION: may be V

<400> SEQUENCE: 3

Trp Ser Phe Val Thr Asn His Asp Gln Arg Lys Asn Leu Ile
1               5                   10

<210> SEQ ID NO 4
<211> LENGTH: 12
<212> TYPE: PRT
<213> ORGANISM: Artificial
<220> FEATURE:
<223> OTHER INFORMATION: GTF conserved region 1
<220> FEATURE:
<221> NAME/KEY: VARIANT
<222> LOCATION: (8)..(8)
<223> OTHER INFORMATION: May be L

<400> SEQUENCE: 4

Gly Leu Lys Val Gln Glu Asp Ile Val Met Asn Gln
1               5                   10

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
gtaagtcgtt actcagcaga tgctaatgg                                    29

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
ggtcagtaaa tccaccgtta ttaattgg                                     28

<210> SEQ ID NO 7
<211> LENGTH: 50
<212> TYPE: DNA
<213> ORGANISM: Artificial
<220> FEATURE:
<223> OTHER INFORMATION: primer

<400> SEQUENCE: 7
gcaattgtcg accatggata caaatactgg tgatcagcaa actgaacagg             50
```

```
<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
ggactgttat cactattatt atttccggcc                                      30

<210> SEQ ID NO 9
<211> LENGTH: 29
<212> TYPE: DNA
<213> ORGANISM: Artificial
<220> FEATURE:
<223> OTHER INFORMATION: primer

<400> SEQUENCE: 9
cgctatgtaa ttgaacagag tattgctgc                                       29

<210> SEQ ID NO 10
<211> LENGTH: 68
<212> TYPE: DNA
<213> ORGANISM: Artificial
<220> FEATURE:
<223> OTHER INFORMATION: primer

<400> SEQUENCE: 10
cctcctttct agatctatta gtgatggtga tggtgatggt tgttaaagtt taatgaaatt     60
gcagttgg                                                              68

<210> SEQ ID NO 11
<211> LENGTH: 19
<212> TYPE: PRT
<213> ORGANISM: Lactobacillus reuteri

<400> SEQUENCE: 11

Phe Asp Gly Phe Arg Val Asp Ala Ala Asp Asn Ile Asp Ala Asp Val
1               5                   10                  15

Leu Asp Gln

<210> SEQ ID NO 12
<211> LENGTH: 13
<212> TYPE: PRT
<213> ORGANISM: Lactobacillus reuteri

<400> SEQUENCE: 12

His Leu Ser Tyr Asn Glu Gly Tyr His Ser Gly Ala Ala
1               5                   10

<210> SEQ ID NO 13
<211> LENGTH: 13
<212> TYPE: PRT
<213> ORGANISM: Lactobacillus reuteri

<400> SEQUENCE: 13

His Leu Val Tyr Asn Glu Gly Tyr His Ser Gly Ala Ala
1               5                   10

<210> SEQ ID NO 14
<211> LENGTH: 14
<212> TYPE: PRT
<213> ORGANISM: Lactobacillus reuteri
```

```
<400> SEQUENCE: 14

Trp Ser Phe Val Thr Asn His Asp Gln Arg Lys Asn Leu Ile
1               5                   10

<210> SEQ ID NO 15
<211> LENGTH: 14
<212> TYPE: PRT
<213> ORGANISM: Lactobacillus reuteri

<400> SEQUENCE: 15

Trp Ser Phe Val Thr Asn His Asp Gln Arg Lys Asn Val Ile
1               5                   10

<210> SEQ ID NO 16
<211> LENGTH: 12
<212> TYPE: PRT
<213> ORGANISM: Lactobacillus reuteri

<400> SEQUENCE: 16

Gly Leu Lys Val Gln Glu Asp Ile Val Met Asn Gln
1               5                   10

<210> SEQ ID NO 17
<211> LENGTH: 12
<212> TYPE: PRT
<213> ORGANISM: Lactobacillus reuteri

<400> SEQUENCE: 17

Gly Leu Lys Val Gln Glu Asp Leu Val Met Asn Gln
1               5                   10

<210> SEQ ID NO 18
<211> LENGTH: 19
<212> TYPE: PRT
<213> ORGANISM: Lactobacillus mesenteroides

<400> SEQUENCE: 18

Phe Asp Ser Ile Arg Ile Asp Ala Val Asp Phe Ile His Asn Asp Thr
1               5                   10                  15

Ile Gln Arg

<210> SEQ ID NO 19
<211> LENGTH: 19
<212> TYPE: PRT
<213> ORGANISM: Lactobacillus mesenteroides

<400> SEQUENCE: 19

Phe Asp Ser Ile Arg Ile Asp Ala Val Asp Phe Ile Asp Asn Asp Ala
1               5                   10                  15

Ile Gln Arg

<210> SEQ ID NO 20
<211> LENGTH: 13
<212> TYPE: PRT
<213> ORGANISM: Lactobacillus mesenteroides

<400> SEQUENCE: 20

His Ile Ser Leu Val Glu Ala Gly Leu Asp Ala Gly Thr
1               5                   10
```

```
<210> SEQ ID NO 21
<211> LENGTH: 15
<212> TYPE: PRT
<213> ORGANISM: Lactobacillus mesenteroides

<400> SEQUENCE: 21

Tyr Ser Ile Ile His Ala His Asp Lys Gly Val Gln Glu Lys Val
1               5                   10                  15

<210> SEQ ID NO 22
<211> LENGTH: 15
<212> TYPE: PRT
<213> ORGANISM: Lactobacillus mesenteroides

<400> SEQUENCE: 22

Tyr Ser Ile Ile His Ala His Asp Lys Gly Ile Gln Glu Lys Val
1               5                   10                  15

<210> SEQ ID NO 23
<211> LENGTH: 12
<212> TYPE: PRT
<213> ORGANISM: Lactobacillus mesenteroides

<400> SEQUENCE: 23

Asn Met Gln Val Met Ala Asp Val Val Asp Asn Gln
1               5                   10

<210> SEQ ID NO 24
<211> LENGTH: 19
<212> TYPE: PRT
<213> ORGANISM: Lactobacillus reuteri

<400> SEQUENCE: 24

Phe Asp Ser Val Arg Val Asp Ala Pro Asp Asn Ile Asp Ala Asp Leu
1               5                   10                  15

Met Asn Ile

<210> SEQ ID NO 25
<211> LENGTH: 19
<212> TYPE: PRT
<213> ORGANISM: Lactobacillus reuteri

<400> SEQUENCE: 25

Phe Asp Ser Ile Arg Val Asp Ala Val Asp Asn Val Asp Ala Asp Leu
1               5                   10                  15

Leu Asn Ile

<210> SEQ ID NO 26
<211> LENGTH: 19
<212> TYPE: PRT
<213> ORGANISM: Lactobacillus reuteri

<400> SEQUENCE: 26

Phe Asp Gly Ile Arg Val Asp Ala Val Asp Asn Val Asp Val Asp Leu
1               5                   10                  15

Leu Ser Ile

<210> SEQ ID NO 27
<211> LENGTH: 19
<212> TYPE: PRT
<213> ORGANISM: Lactobacillus reuteri
```

```
<400> SEQUENCE: 27

Phe Asp Ser Ile Arg Val Asp Ala Val Asp Asn Val Asp Ala Asp Leu
1               5                   10                  15

Leu Asp Ile

<210> SEQ ID NO 28
<211> LENGTH: 19
<212> TYPE: PRT
<213> ORGANISM: Lactobacillus parabuchneri

<400> SEQUENCE: 28

Phe Asp Gly Tyr Arg Val Asp Ala Val Asp Asn Val Asp Ala Asp Leu
1               5                   10                  15

Leu Asn Ile

<210> SEQ ID NO 29
<211> LENGTH: 19
<212> TYPE: PRT
<213> ORGANISM: Lactobacillus sake

<400> SEQUENCE: 29

Phe Asp Ser Val Arg Val Asp Ala Val Asp Asn Val Asp Ala Asp Leu
1               5                   10                  15

Leu Asn Ile

<210> SEQ ID NO 30
<211> LENGTH: 19
<212> TYPE: PRT
<213> ORGANISM: Lactobacillus fermentum

<400> SEQUENCE: 30

Phe Asp Ala Ile Arg Ile Asp Ala Val Asp Asn Val Asp Ala Asp Leu
1               5                   10                  15

Leu Gln Leu

<210> SEQ ID NO 31
<211> LENGTH: 19
<212> TYPE: PRT
<213> ORGANISM: Lactobacillus mesenteroides

<400> SEQUENCE: 31

Phe Asp Gly Tyr Arg Val Asp Ala Val Asp Asn Val Asp Ala Asp Leu
1               5                   10                  15

Leu Gln Ile

<210> SEQ ID NO 32
<211> LENGTH: 19
<212> TYPE: PRT
<213> ORGANISM: Lactobacillus mesenteroides

<400> SEQUENCE: 32

Phe Asp Gly Tyr Arg Val Asp Ala Val Asp Asn Val Asn Ala Asp Leu
1               5                   10                  15

Leu Gln Ile

<210> SEQ ID NO 33
<211> LENGTH: 13
<212> TYPE: PRT
<213> ORGANISM: Lactobacillus reuteri
```

```
<400> SEQUENCE: 33

His Ile Asn Ile Leu Glu Asp Trp Asn His Ala Asp Pro
1               5                   10

<210> SEQ ID NO 34
<211> LENGTH: 13
<212> TYPE: PRT
<213> ORGANISM: Lactobacillus reuteri

<400> SEQUENCE: 34

His Leu Asn Ile Leu Glu Asp Trp Ser His Ala Asp Pro
1               5                   10

<210> SEQ ID NO 35
<211> LENGTH: 13
<212> TYPE: PRT
<213> ORGANISM: Lactobacillus reuteri

<400> SEQUENCE: 35

His Ile Asn Ile Leu Glu Asp Trp Asn Ser Ser Asp Pro
1               5                   10

<210> SEQ ID NO 36
<211> LENGTH: 13
<212> TYPE: PRT
<213> ORGANISM: Lactobacillus reuteri

<400> SEQUENCE: 36

His Ile Asn Ile Leu Glu Asp Trp Gly Trp Asp Asp Pro
1               5                   10

<210> SEQ ID NO 37
<211> LENGTH: 13
<212> TYPE: PRT
<213> ORGANISM: Lactobacillus reuteri

<400> SEQUENCE: 37

His Ile Asn Ile Leu Glu Asp Trp Gly Gly Gln Asp Pro
1               5                   10

<210> SEQ ID NO 38
<211> LENGTH: 13
<212> TYPE: PRT
<213> ORGANISM: Lactobacillus parabuchneri

<400> SEQUENCE: 38

His Leu Ser Ile Leu Glu Asp Trp Asp Asn Asn Asp Pro
1               5                   10

<210> SEQ ID NO 39
<211> LENGTH: 13
<212> TYPE: PRT
<213> ORGANISM: Lactobacillus sake

<400> SEQUENCE: 39

His Leu Ser Ile Leu Glu Asp Trp Gly His Asn Asp Pro
1               5                   10

<210> SEQ ID NO 40
<211> LENGTH: 13
<212> TYPE: PRT
<213> ORGANISM: Lactobacillus fermentum
```

```
<400> SEQUENCE: 40

His Leu Ser Ile Leu Glu Asp Trp Ser His Asn Asp Pro
1               5                   10

<210> SEQ ID NO 41
<211> LENGTH: 13
<212> TYPE: PRT
<213> ORGANISM: Lactobacillus mesenteroides

<400> SEQUENCE: 41

His Ile Ser Ile Leu Glu Asp Trp Asp Asn Asn Asp Ser
1               5                   10

<210> SEQ ID NO 42
<211> LENGTH: 13
<212> TYPE: PRT
<213> ORGANISM: Lactobacillus mesenteroides

<400> SEQUENCE: 42

His Ile Ser Ile Leu Glu Asp Trp Asp Asn Asn Asp Pro
1               5                   10

<210> SEQ ID NO 43
<211> LENGTH: 15
<212> TYPE: PRT
<213> ORGANISM: Lactobacillus reuteri

<400> SEQUENCE: 43

Tyr Ser Phe Val Arg Ala His Asp Asn Asn Ser Gln Asp Gln Ile
1               5                   10                  15

<210> SEQ ID NO 44
<211> LENGTH: 15
<212> TYPE: PRT
<213> ORGANISM: Lactobacillus reuteri

<400> SEQUENCE: 44

Tyr Thr Phe Ile Arg Ala His Asp Ser Asn Ala Gln Asp Gln Ile
1               5                   10                  15

<210> SEQ ID NO 45
<211> LENGTH: 15
<212> TYPE: PRT
<213> ORGANISM: Lactobacillus reuteri

<400> SEQUENCE: 45

Tyr Ser Phe Ile Arg Ala His Asp Asn Asn Ser Gln Asp Gln Ile
1               5                   10                  15

<210> SEQ ID NO 46
<211> LENGTH: 15
<212> TYPE: PRT
<213> ORGANISM: Lactobacillus reuteri

<400> SEQUENCE: 46

Tyr Asn Phe Val Arg Ala His Asp Ser Asn Ala Gln Asp Gln Ile
1               5                   10                  15

<210> SEQ ID NO 47
<211> LENGTH: 15
<212> TYPE: PRT
<213> ORGANISM: Lactobacillus reuteri
```

-continued

```
<400> SEQUENCE: 47

Tyr Ser Phe Ile Arg Ala His Asp Asn Gly Ser Gln Asp Asp Ile
1               5                   10                  15

<210> SEQ ID NO 48
<211> LENGTH: 15
<212> TYPE: PRT
<213> ORGANISM: Lactobacillus buchneri

<400> SEQUENCE: 48

Tyr Thr Phe Ile Arg Ala His Asp Ser Glu Val Gln Thr Ile Ile
1               5                   10                  15

<210> SEQ ID NO 49
<211> LENGTH: 15
<212> TYPE: PRT
<213> ORGANISM: Lactobacillus sake

<400> SEQUENCE: 49

Tyr Ser Phe Val Arg Ala His Asp Ser Glu Val Gln Thr Val Ile
1               5                   10                  15

<210> SEQ ID NO 50
<211> LENGTH: 15
<212> TYPE: PRT
<213> ORGANISM: Lactobacillus mesenteroides

<400> SEQUENCE: 50

Tyr Ala Phe Ile Arg Ala His Asp Ser Glu Val Gln Thr Val Ile
1               5                   10                  15

<210> SEQ ID NO 51
<211> LENGTH: 15
<212> TYPE: PRT
<213> ORGANISM: Lactobacillus mesenteroides

<400> SEQUENCE: 51

Tyr Ser Phe Ile Arg Ala His Asp Ser Glu Val Gln Thr Val Ile
1               5                   10                  15

<210> SEQ ID NO 52
<211> LENGTH: 12
<212> TYPE: PRT
<213> ORGANISM: Lactobacillus reuteri

<400> SEQUENCE: 52

Gly Leu Gln Val Met Ala Asp Trp Val Pro Asp Gln
1               5                   10

<210> SEQ ID NO 53
<211> LENGTH: 12
<212> TYPE: PRT
<213> ORGANISM: Lactobacillus reuteri

<400> SEQUENCE: 53

Gly Leu Gln Ala Ile Ala Asp Trp Val Pro Asp Gln
1               5                   10

<210> SEQ ID NO 54
<211> LENGTH: 12
<212> TYPE: PRT
<213> ORGANISM: Lactobacillus reuteri
```

<400> SEQUENCE: 54

Gly Ile Gln Ala Met Ala Asp Trp Val Pro Asp Gln
1               5                   10

<210> SEQ ID NO 55
<211> LENGTH: 12
<212> TYPE: PRT
<213> ORGANISM: Lactobacillus buchneri

<400> SEQUENCE: 55

Gly Ile Gln Ala Ile Asp Asp Trp Val Pro Asp Gln
1               5                   10

<210> SEQ ID NO 56
<211> LENGTH: 12
<212> TYPE: PRT
<213> ORGANISM: Lactobacillus sake

<400> SEQUENCE: 56

Gly Ile Gln Val Met Ala Asp Phe Val Pro Asp Gln
1               5                   10

<210> SEQ ID NO 57
<211> LENGTH: 12
<212> TYPE: PRT
<213> ORGANISM: Lactobacillus fermentum

<400> SEQUENCE: 57

Gly Met Gln Val Met Ala Asp Phe Val Pro Asp Gln
1               5                   10

<210> SEQ ID NO 58
<211> LENGTH: 12
<212> TYPE: PRT
<213> ORGANISM: Lactobacillus mesenteroides

<400> SEQUENCE: 58

Gly Ile Gln Ala Ile Asn Asp Trp Val Pro Asp Gln
1               5                   10

<210> SEQ ID NO 59
<211> LENGTH: 1619
<212> TYPE: PRT
<213> ORGANISM: Lactobacillus fermentum

<400> SEQUENCE: 59

Met Glu Leu Lys Lys His Phe Lys Leu Tyr Lys Ser Gly Lys Gln Trp
1               5                   10                  15

Val Thr Ala Ala Val Ala Thr Ile Ala Phe Ser Ala Gly Val Leu Thr
                20                  25                  30

Thr Ser Glu Val Val His Ala Asp Thr Asn Thr Gly Asp Gln Gln Thr
            35                  40                  45

Glu Gln Val Thr Gln Pro Ser Asn Ser Thr Thr Gln Asp Val Lys Pro
        50                  55                  60

Val Ser Thr Asp Ala Ser Ser Asp Thr Lys Ile Val Ser Asp Asn Lys
65                  70                  75                  80

Glu Asn Asn Asn Gln Val Gly Asn Thr Asn Val Ser Gly Gln Asn Ser
                85                  90                  95

Ser Lys Asp Thr Lys Ser Val Leu Thr Gly Thr Asn Ser Val Thr Gln
                100                 105                 110

```
Asn Tyr Asp His Asn Asp Asn Gly Asn Tyr Gly Tyr Ile Asp Ser Ala
            115                 120                 125
Asn Leu Asn Asn Asn Gln Leu Gln Val Ser Gly Trp Ser Ala Thr Asn
        130                 135                 140
Gln Asn Ile Asn Lys Asp Asn His Phe Ile Ile Ala Tyr Asp Ser Thr
145                 150                 155                 160
Ser Gln Gln Glu Leu Gly Arg Thr Lys Val Glu Thr Pro Val Ala Arg
                165                 170                 175
Pro Asp Val Lys Ala Val His Asn Val Tyr Asn Ala Glu Asn Ser Gly
            180                 185                 190
Phe Asn Val Asn Val Ser Leu Asn Phe Asp Lys Met Asn Asn Tyr Arg
        195                 200                 205
Asp Ala Ile Lys Ile Ile Ser Arg Tyr Ser Gly Val Pro Asp Gly Asn
    210                 215                 220
Ser Asp Tyr Val Asp Phe Val Ser Gln Pro Ile Ile Phe Asp Glu Asn
225                 230                 235                 240
Asn Tyr Ala His Leu Asp Asp Phe Ser Val Gln Asn Gly Lys Leu His
                245                 250                 255
Val Ser Gly Trp Asn Ala Thr Asn Lys Ala Ile Gln Asn Pro Asn His
            260                 265                 270
Phe Leu Ile Leu Phe Asp Arg Thr Ile Asn Arg Glu Val Ala Arg Gln
        275                 280                 285
Lys Val Thr Ala Gly Ile Asn Arg Pro Asp Val Glu Lys Ala Tyr Pro
    290                 295                 300
Gln Val Ile Asn Ala Asn Ile Ser Gly Phe Asp Ala Ala Phe Asp Ile
305                 310                 315                 320
Thr Thr Leu Asn Pro Asn Asp Glu Tyr Gln Ile Leu Ser Arg Tyr Ser
                325                 330                 335
Asn Asp Asp Asn Gly Glu Gly Ser Tyr Val Thr Tyr Trp Phe Lys Pro
            340                 345                 350
Gln Arg Ile Ala Pro Ala Asn Gln Phe Asn Ser Gly His Leu Asp Ser
        355                 360                 365
Phe Asn Ile Ser Lys Ala Gly Lys Val Thr Val Ser Gly Trp Gln Ala
    370                 375                 380
Thr Asn Leu Ser Asn Ile Gln Ser Asn Arg Phe Ile Ile Leu Phe Asp
385                 390                 395                 400
Asn Thr Ala Asn His Gln Ile Ala Ser Thr Lys Ile Thr Asn Thr Ala
                405                 410                 415
Arg Pro Asp Val Glu Lys Val Tyr Pro Gln Val Leu Asn Ala Thr Asn
            420                 425                 430
Ser Gly Tyr Asp Val Thr Phe Asp Leu Thr Gln Asp Gln Ile Ala Gln
        435                 440                 445
Leu Leu Pro Asn His Ser Tyr Ser Ile Val Ser Arg Tyr Ser Ala Asp
    450                 455                 460
Ala Asn Gly Asn Gly Asn Asp Lys Gln His Thr Asp Phe Trp Ser Thr
465                 470                 475                 480
Pro Ile Thr Leu Asn Lys Thr Ala Ser Tyr Ile Asp Ser Ile Ser Leu
                485                 490                 495
Asn Gly Asn Glu Leu Asn Val Arg Gly Trp Met Ala Ser Asp Ala Ser
            500                 505                 510
Ala Thr Gln Ala Asn Pro Tyr Leu Ile Val Leu Asn Asn Gly Lys Glu
        515                 520                 525
```

Val Thr Arg Gln Lys Leu Thr Leu Val Ala Arg Pro Asp Val Ala Lys
530                     535                     540

Val Tyr Pro Asp Val Tyr Ser Ser Leu Asp Ser Gly Phe Asn Thr Thr
545                     550                     555                     560

Ile Lys Leu Thr Val Pro Gln Leu Asn Glu Leu Thr Gly Asn Met Gln
                565                     570                     575

Val Leu Leu Arg Tyr Ser Thr Ala Ala Asp Gly Asn Pro Ile Asn Asn
                580                     585                     590

Gly Gly Phe Thr Asp Gln Tyr Ser Lys Asn Tyr Ala Thr Asn Gly Gly
                595                     600                     605

Ser Phe Asp Phe Val Lys Val Asp Asn Gln Val Ala Phe Ser Gly
610                     615                     620

Trp His Val Ser Asp Gln Ala Thr Asp Lys Pro Tyr Gln Trp Ile Ile
625                     630                     635                     640

Val Leu Ala Asn Gly Lys Glu Val Gly Arg Gln Leu Ile Ser Ser Thr
                645                     650                     655

Thr Asn Gly Phe Val Ser Tyr Asn Arg Pro Asp Val Tyr Asn Val Asn
                660                     665                     670

Pro Ala Ile Ser Asn Ser Ser Thr Ser Gly Phe Gln Gly Ile Met Thr
                675                     680                     685

Leu Lys Asp Asn Ile Lys Asn Ala Asn Val Gln Leu Val His Arg Phe
690                     695                     700

Ser Asp Asp Gly Gln Asn Gly Glu Gly Asn Arg Val Asp Tyr Trp Ser
705                     710                     715                     720

Glu Val Met Pro Val Thr Asn Thr Phe Gln Lys Gly Thr Asp Gln Leu
                725                     730                     735

Met Arg Asn Leu Val Ala Lys Pro Asn Lys Asn Gln Leu Lys Ile Tyr
                740                     745                     750

Asn Gly Asn Thr Leu Val Lys Thr Leu Gly Pro Gly Thr Trp Glu Asn
                755                     760                     765

Met Ala Phe Ala Gln Asp Ser Ser Ala Ile Asn Asn Ile Asp Gly Tyr
770                     775                     780

Leu Ser Tyr Thr Asp Trp Tyr Arg Pro Tyr Gly Thr Ser Gln Asp Gly
785                     790                     795                     800

Lys Thr Trp Tyr Lys Thr Thr Ala Met Asp Trp Arg Pro Leu Leu Met
                805                     810                     815

Tyr Ile Trp Pro Ser Lys Asp Val Gln Ala Gln Phe Ile Lys Tyr Phe
                820                     825                     830

Val Asn Asn Gly Tyr Glu Asn Ala Asn Tyr Gly Leu Thr Lys Asp Thr
                835                     840                     845

Val Ala Asn Ile Asn Lys Asp Thr Asn Thr Val Leu Ala Asn Met
850                     855                     860

Ala Gln Asn Leu Arg Tyr Val Ile Glu Gln Ser Ile Ala Ala Asn Lys
865                     870                     875                     880

Gly Thr Ser Lys Leu Ala Asn Asp Ile Asn Ser Phe Ala Ala Thr Val
                885                     890                     895

Pro Glu Leu Ser Ala Ser Ser Glu Leu Ser Leu Gln Ser Met Pro Asn
                900                     905                     910

Tyr Arg Pro Asp Lys Ser Gly Thr Ile Asp Ser Asp Gln Val Ile Phe
                915                     920                     925

Val Asn Asn Asn Ser Lys Asp Pro Arg Lys Gly Asn Thr Ser Tyr Ala
930                     935                     940

Asp Ser Asn Tyr Arg Leu Met Asn Arg Thr Ile Asn Asn Gln Ala Gly

-continued

```
945             950             955             960
Asn Asn Asn Ser Asp Asn Ser Pro Glu Leu Leu Val Gly Asn Asp Ile
                965             970             975
Asp Asn Ser Asn Pro Val Val Gln Ala Glu Asn Leu Asn Trp Glu Tyr
                980             985             990
Phe Leu Leu Asn Tyr Gly Lys Leu Met Gly Tyr Asn Pro Asp Gly Asn
                995             1000            1005
Phe Asp Gly Phe Arg Val Asp Ala Ala Asp Asn Ile Asp Ala Asp
    1010            1015            1020
Val Leu Asp Gln Met Gly Gln Leu Met Asn Asp Met Tyr His Thr
    1025            1030            1035
Lys Gly Asn Pro Gln Asn Ala Asn Asp His Leu Ser Tyr Asn Glu
    1040            1045            1050
Gly Tyr His Ser Gly Ala Ala Gln Met Leu Asn Glu Lys Gly Asn
    1055            1060            1065
Pro Gln Leu Tyr Met Asp Ser Gly Glu Phe Tyr Thr Leu Glu Asn
    1070            1075            1080
Val Leu Gly Arg Ala Asn Asn Arg Asp Asn Ile Gly Asn Leu Ile
    1085            1090            1095
Thr Asn Ser Ile Val Asn Arg Gln Asn Asp Thr Thr Glu Asn Glu
    1100            1105            1110
Ala Thr Pro Asn Trp Ser Phe Val Thr Asn His Asp Gln Arg Lys
    1115            1120            1125
Asn Leu Ile Asn Arg Leu Ile Ile Lys Asp His Ser Asn Ile Pro
    1130            1135            1140
Asp Ile Met Gly Ser Ala Tyr Lys Val Glu Tyr Ala Asn Gln Ala
    1145            1150            1155
Trp Gln Glu Phe Tyr Ala Asp Gln Glu Lys Thr Asn Lys Gln Tyr
    1160            1165            1170
Ala Gln Tyr Asn Val Pro Ala Gln Tyr Ala Ile Leu Leu Ser Asn
    1175            1180            1185
Lys Asp Thr Val Pro Gln Val Tyr Tyr Gly Asp Leu Tyr Asn Glu
    1190            1195            1200
Thr Ala Gln Tyr Met Gln Glu Lys Ser Ile Tyr Tyr Asp Ala Ile
    1205            1210            1215
Thr Thr Leu Met Arg Ala Arg Lys Gln Phe Val Ser Gly Gly Gln
    1220            1225            1230
Thr Met Thr Lys Leu Asn Asn Asn Leu Leu Ala Ser Val Arg Tyr
    1235            1240            1245
Gly Lys Gly Val Val Asp Ala Asn Ser Asn Gly Thr Asp Lys Leu
    1250            1255            1260
Ser Arg Thr Ser Gly Met Ala Val Leu Val Gly Asn Asp Ser Asn
    1265            1270            1275
Met Ala Gln Gln Ser Val Ala Ile Asn Met Gly Arg Ala His Ala
    1280            1285            1290
Asn Gln Gln Tyr Arg Asn Leu Ile Asp Thr Thr Glu Asn Gly Leu
    1295            1300            1305
Thr Tyr Asp Ala Asp Asn Ser Glu Asn Pro Ala Ile Leu Thr Thr
    1310            1315            1320
Asp Ser Asn Gly Ile Leu Lys Val Thr Val Lys Gly Tyr Ser Asn
    1325            1330            1335
Pro Tyr Val Ser Gly Tyr Leu Gly Val Trp Val Pro Val Ile Ser
    1340            1345            1350
```

```
Gly Asp Gln Asp Val Thr Thr Asn Ala Ser Asp Val Val Ala Asn
    1355                1360                1365

Lys Glu Lys Thr Phe Glu Ser Asn Ala Ala Leu Asp Ser His Met
1370                1375                1380

Ile Tyr Glu Asp Phe Ser Leu Phe Gln Pro Glu Pro Thr Ser Val
    1385                1390                1395

Glu Asn His Ala Tyr Asn Val Ile Ala Lys Asn Ala Ser Leu Phe
1400                1405                1410

Ser Asp Leu Gly Ile Thr Asp Phe Trp Met Ala Pro Ala Tyr Thr
    1415                1420                1425

Pro Phe Gly Arg Ser Arg Tyr Asn Glu Gly Tyr Ser Met Thr Asp
1430                1435                1440

Arg Tyr Asn Leu Gly Thr Thr Ala Asn Pro Thr Lys Tyr Gly Ser
    1445                1450                1455

Gly Glu Glu Leu Ala Asn Thr Ile Ala Ala Leu His Lys Ala Gly
1460                1465                1470

Leu Lys Val Gln Glu Asp Ile Val Met Asn Gln Met Ile Gly Phe
    1475                1480                1485

Ser Gly Gln Glu Ala Val Thr Val Thr Arg Thr Asn Asn Arg Gly
1490                1495                1500

Met Gln Ile His Val Asn Gly Gln Thr Tyr Ala Asn Gln Ile Tyr
    1505                1510                1515

Phe Ala Tyr Thr Thr Gly Gly Gly Asn Gly Gln Glu Thr Tyr Gly
1520                1525                1530

Gly Lys Tyr Leu Ala Glu Leu Gln Lys Asn Tyr Pro Asp Leu Phe
    1535                1540                1545

Thr Thr Lys Ala Ile Ser Thr Gly Val Ala Pro Asp Pro Thr Val
1550                1555                1560

Arg Ile Asn Lys Trp Ser Ala Lys Tyr Gln Asn Gly Thr Ser Leu
    1565                1570                1575

Gln Asn Ile Gly Ile Gly Leu Ala Val Lys Leu Ala Asn Gly Asp
1580                1585                1590

Tyr Ala Tyr Leu Asn Ser Gly Asp Asn Lys Ala Phe Asn Thr Leu
    1595                1600                1605

Leu Pro Thr Ala Ile Ser Leu Asn Phe Asn Asn
    1610                1615

<210> SEQ ID NO 60
<211> LENGTH: 695
<212> TYPE: PRT
<213> ORGANISM: Lactobacillus fermentum

<400> SEQUENCE: 60

Trp Tyr Arg Pro Tyr Gly Thr Ser Gln Asp Gly Lys Thr Trp Tyr Lys
1               5                   10                  15

Thr Thr Ala Met Asp Trp Arg Pro Leu Leu Met Tyr Ile Trp Pro Ser
            20                  25                  30

Lys Asp Val Gln Ala Gln Phe Ile Lys Tyr Phe Val Asn Asn Gly Tyr
        35                  40                  45

Glu Asn Ala Asn Tyr Gly Leu Thr Lys Asp Thr Val Ala Asn Ile Asn
    50                  55                  60

Lys Asp Thr Asn Thr Thr Val Leu Ala Asn Met Ala Gln Asn Leu Arg
65                  70                  75                  80

Tyr Val Ile Glu Gln Ser Ile Ala Ala Asn Lys Gly Thr Ser Lys Leu
```

```
                     85                 90                  95
Ala Asn Asp Ile Asn Ser Phe Ala Ala Thr Val Pro Glu Leu Ser Ala
                100                105                110
Ser Ser Glu Leu Ser Leu Gln Ser Met Pro Asn Tyr Arg Pro Asp Lys
                115                120                125
Ser Gly Thr Ile Asp Ser Asp Gln Val Ile Phe Val Asn Asn Asn Ser
            130                135                140
Lys Asp Pro Arg Lys Gly Asn Thr Ser Tyr Ala Asp Ser Asn Tyr Arg
145                150                155                160
Leu Met Asn Arg Thr Ile Asn Asn Gln Ala Gly Asn Asn Asn Ser Asp
                165                170                175
Asn Ser Pro Glu Leu Leu Val Gly Asn Asp Ile Asp Asn Ser Asn Pro
                180                185                190
Val Val Gln Ala Glu Asn Leu Asn Trp Glu Tyr Phe Leu Leu Asn Tyr
                195                200                205
Gly Lys Leu Met Gly Tyr Asn Pro Asp Gly Asn Phe Asp Gly Phe Arg
            210                215                220
Val Asp Ala Ala Asp Asn Ile Asp Ala Asp Val Leu Asp Gln Met Gly
225                230                235                240
Gln Leu Met Asn Asp Met Tyr His Thr Lys Gly Asn Pro Gln Asn Ala
                    245                250                255
Asn Asp His Leu Ser Tyr Asn Glu Gly Tyr His Ser Gly Ala Ala Gln
                260                265                270
Met Leu Asn Glu Lys Gly Asn Pro Gln Leu Tyr Met Asp Ser Gly Glu
                275                280                285
Phe Tyr Thr Leu Glu Asn Val Leu Gly Arg Ala Asn Asn Arg Asp Asn
                290                295                300
Ile Gly Asn Leu Ile Thr Asn Ser Ile Val Asn Arg Gln Asn Asp Thr
305                310                315                320
Thr Glu Asn Glu Ala Thr Pro Asn Trp Ser Phe Val Thr Asn His Asp
                325                330                335
Gln Arg Lys Asn Leu Ile Asn Arg Leu Ile Ile Lys Asp His Ser Asn
                340                345                350
Ile Pro Asp Ile Met Gly Ser Ala Tyr Lys Val Glu Tyr Ala Asn Gln
                355                360                365
Ala Trp Gln Glu Phe Tyr Ala Asp Gln Glu Lys Thr Asn Lys Gln Tyr
                370                375                380
Ala Gln Tyr Asn Val Pro Ala Gln Tyr Ala Ile Leu Leu Ser Asn Lys
385                390                395                400
Asp Thr Val Pro Gln Val Tyr Tyr Gly Asp Leu Tyr Asn Glu Thr Ala
                    405                410                415
Gln Tyr Met Gln Glu Lys Ser Ile Tyr Tyr Asp Ala Ile Thr Thr Leu
                420                425                430
Met Arg Ala Arg Lys Gln Phe Val Ser Gly Gly Gln Thr Met Thr Lys
                435                440                445
Leu Asn Asn Asn Leu Leu Ala Ser Val Arg Tyr Gly Lys Gly Val Val
                450                455                460
Asp Ala Asn Ser Asn Gly Thr Asp Lys Leu Ser Arg Thr Ser Gly Met
465                470                475                480
Ala Val Leu Val Gly Asn Asp Ser Asn Met Ala Gln Gln Ser Val Ala
                    485                490                495
Ile Asn Met Gly Arg Ala His Ala Asn Gln Gln Tyr Arg Asn Leu Ile
                500                505                510
```

Asp Thr Thr Glu Asn Gly Leu Thr Tyr Asp Ala Asp Asn Ser Glu Asn
            515                 520                 525

Pro Ala Ile Leu Thr Thr Asp Ser Asn Gly Ile Leu Lys Val Thr Val
        530                 535                 540

Lys Gly Tyr Ser Asn Pro Tyr Val Ser Gly Tyr Leu Gly Val Trp Val
545                 550                 555                 560

Pro Val Ile Ser Gly Asp Gln Asp Val Thr Thr Asn Ala Ser Asp Val
                565                 570                 575

Val Ala Asn Lys Glu Lys Thr Phe Glu Ser Asn Ala Ala Leu Asp Ser
            580                 585                 590

His Met Ile Tyr Glu Asp Phe Ser Leu Phe Gln Pro Glu Pro Thr Ser
        595                 600                 605

Val Glu Asn His Ala Tyr Asn Val Ile Ala Lys Asn Ala Ser Leu Phe
    610                 615                 620

Ser Asp Leu Gly Ile Thr Asp Phe Trp Met Ala Pro Ala Tyr Thr Pro
625                 630                 635                 640

Phe Gly Arg Ser Arg Tyr Asn Glu Gly Tyr Ser Met Thr Asp Arg Tyr
                645                 650                 655

Asn Leu Gly Thr Thr Ala Asn Pro Thr Lys Tyr Gly Ser Gly Glu Glu
            660                 665                 670

Leu Ala Asn Thr Ile Ala Ala Leu His Lys Ala Gly Leu Lys Val Gln
        675                 680                 685

Glu Asp Ile Val Met Asn Gln
    690                 695

<210> SEQ ID NO 61
<211> LENGTH: 1383
<212> TYPE: PRT
<213> ORGANISM: Lactobacillus reuteri
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 61

Phe Xaa Glu Asn Asn Xaa Ala Tyr Leu Asp Asp Phe Ser Val Gln Asn
1               5                   10                  15

Gly Lys Leu His Val Ser Gly Trp Asn Ala Thr Asn Lys Ala Ile Gln
            20                  25                  30

Arg Pro Asn His Phe Leu Ile Leu Phe Asp Arg Thr Val Asn Arg Glu
        35                  40                  45

Val Ala Arg Gln Lys Val Thr Ala Gly Ile Asn Arg Ser Asp Val Glu
    50                  55                  60

Lys Val Tyr Pro Gln Val Val Asn Ala Asn Val Ser Gly Phe Asp Ala
65                  70                  75                  80

Thr Phe Asp Thr Ile Asn Leu Asn Pro Asn His Glu Tyr Gln Ile Leu
                85                  90                  95

Ser Arg Tyr Ser Asn Asn Gly Asp Gly Glu Gly Asp Tyr Val Thr Tyr
            100                 105                 110

Trp Phe Asn Pro Gln Arg Ile Ala Pro Val Asn Gln Phe Asn Asn Gly
        115                 120                 125

His Leu Asp Asn Phe Asp Ile Ser Lys Ala Gly Lys Val Thr Val Ser
    130                 135                 140

```
Gly Trp Gln Ala Thr Asn Leu Ser Asn Ile Gln Asn Arg Tyr Ile
145                 150                 155                 160

Ile Leu Phe Asp Thr Thr Ala Asn Arg Gln Ile Ala Ser Met Lys Val
                165                 170                 175

Thr Gly Val Asp Arg Pro Asp Val Ala Lys Val Tyr Pro Gln Ile Leu
            180                 185                 190

Asn Ala Asn Lys Ser Gly Tyr Asn Val Thr Phe Asp Leu Thr Gln Ala
            195                 200                 205

Gln Ile Ala Gln Leu Phe Pro Asn His Ser Tyr Ser Ile Val Ser Arg
210                 215                 220

Tyr Ser Ala Asp Pro Asn Gly Asn Gly Asn Asp Lys Gln His Thr Asp
225                 230                 235                 240

Phe Trp Ser Ala Pro Ile Val Leu Asn Lys Thr Ala Ser Tyr Ile Asp
                245                 250                 255

Asp Ile Ser Leu Asn Gly Asp Val Leu Asn Val Lys Gly Trp Met Ala
            260                 265                 270

Ser Asp Ala Ser Ala Thr Gln Ala Asn Pro Tyr Ile Ile Leu Asn
            275                 280                 285

Asn Gly Lys Glu Val Thr Arg Gln Lys Leu Thr Leu Asn Asp Arg Pro
290                 295                 300

Asp Val Ala Lys Val Tyr Pro Asp Val Tyr Asn Ser Leu Ala Ser Gly
305                 310                 315                 320

Phe Asp Thr Thr Ile Lys Leu Thr Asn Ser Gln Leu Asn Ala Leu Asn
                325                 330                 335

Gly Asn Met Gln Ile Leu Leu Arg Tyr Ser Ala Ala Asp Gly Asn
            340                 345                 350

Pro Ile Asn Asn Gly Gly Phe Thr Asp Gln Tyr Ser Lys Asn Tyr Ala
            355                 360                 365

Thr Asn Gly Gly Ser Phe Asp Phe Val Lys Val Asp Asn Asn Gln Val
370                 375                 380

Ala Phe Ser Gly Trp His Val Ser Asp Gln Ala Thr Asp Lys Pro Tyr
385                 390                 395                 400

Gln Trp Ile Ile Val Leu Val Asn Gly Lys Glu Val Gly Arg Gln Leu
                405                 410                 415

Ile Ser Ser Thr Thr Asn Gly Leu Val Ser Tyr Asn Arg Pro Asp Val
            420                 425                 430

Tyr Asn Val Asn Pro Ala Ile Ser Asn Ser Thr Ser Gly Phe Gln
            435                 440                 445

Gly Ile Met Thr Leu Lys Asp Asn Ile Lys Asn Ala Asn Val Gln Leu
            450                 455                 460

Val His Arg Phe Ser Asp Asp Gln Asn Gly Glu Gly Asn Arg Val
465                 470                 475                 480

Asp Tyr Trp Ser Glu Val Met Pro Val Thr Asn Thr Phe Gln Lys Gly
                485                 490                 495

Thr Asp Gln Leu Met Arg Asn Leu Val Ala Lys Pro Asn Lys Asn Gln
            500                 505                 510

Leu Lys Ile Tyr Asn Gly Asn Thr Leu Val Lys Thr Leu Gly Pro Gly
            515                 520                 525

Thr Trp Glu Asn Met Ala Phe Ala Gln Asp Ser Ser Ala Ile Asn Asn
            530                 535                 540

Ile Asp Gly Tyr Leu Ser Tyr Thr Gly Trp Tyr Arg Pro Tyr Gly Thr
545                 550                 555                 560
```

```
Ser Gln Asp Gly Lys Thr Trp Tyr Glu Thr Ala Met Asp Trp Arg
            565                 570                 575

Pro Leu Leu Met Tyr Ile Trp Pro Ser Lys Asp Val Gln Ala Gln Phe
            580                 585                 590

Ile Lys Tyr Phe Val Asn Asn Gly Tyr Glu Asn Ala Asn Tyr Gly Leu
            595                 600                 605

Thr Lys Ser Ser Val Ala Ser Phe Ser Lys Asp Thr Asn Ala Asn Leu
            610                 615                 620

Leu Asp Val Thr Ala Gln Asn Leu Arg Tyr Val Ile Glu Gln Ser Ile
625                 630                 635                 640

Ala Ala Asn Lys Gly Thr Ser Lys Leu Ala Asn Asp Ile Asn Ser Phe
            645                 650                 655

Ala Ala Thr Val Pro Glu Leu Ser Ala Ser Ser Glu Leu Ser Leu Gln
            660                 665                 670

Ser Met Pro Asn Tyr Arg Pro Asp Glu Ser Gly Thr Val Asp Ser Asp
            675                 680                 685

Gln Val Ile Phe Val Asn Asn Ser Lys Asp Pro Arg Lys Gly Asn
            690                 695                 700

Thr Ser Tyr Ala Asp Ser Asn Tyr Arg Leu Met Asn Arg Thr Ile Asn
705                 710                 715                 720

Asn Gln Ala Gly Asn Asn Ser Asp Asn Ser Pro Glu Leu Leu Val
            725                 730                 735

Gly Asn Asp Ile Asp Asn Ser Asn Pro Val Val Gln Ala Glu Asn Leu
            740                 745                 750

Asn Trp Glu Tyr Phe Leu Leu Asn Tyr Gly Lys Leu Met Gly Tyr Asn
            755                 760                 765

Pro Asp Gly Asn Phe Asp Gly Phe Arg Val Asp Ala Ala Asp Asn Ile
            770                 775                 780

Asp Ala Asp Val Leu Asp Gln Met Gly Gln Leu Met Asn Asp Met Tyr
785                 790                 795                 800

His Thr Lys Gly Asn Pro Gln Asn Ala Asn Asp His Leu Ser Tyr Asn
            805                 810                 815

Glu Gly Tyr His Ser Gly Ala Ala Gln Met Leu Asn Glu Lys Gly Asn
            820                 825                 830

Pro Gln Leu Tyr Met Asp Ser Gly Glu Phe Tyr Thr Leu Glu Asn Val
            835                 840                 845

Leu Gly Arg Ala Asn Asn Arg Asp Asn Ile Gly Asn Leu Ile Thr Asn
            850                 855                 860

Ser Ile Val Asn Arg Gln Asn Asp Thr Thr Glu Asn Glu Ala Thr Pro
865                 870                 875                 880

Asn Trp Ser Phe Val Thr Asn His Asp Gln Arg Lys Asn Leu Ile Asn
            885                 890                 895

Arg Leu Ile Ile Lys Asp His Ser Asn Ile Pro Asp Ile Met Gly Ser
            900                 905                 910

Ala Tyr Lys Val Glu Tyr Ala Asn Gln Ala Trp Gln Glu Phe Tyr Ala
            915                 920                 925

Asp Gln Glu Lys Thr Asn Lys Gln Tyr Ala Gln Tyr Asn Val Pro Ala
            930                 935                 940

Gln Tyr Ala Ile Leu Leu Ser Asn Lys Asp Thr Val Pro Gln Val Tyr
945                 950                 955                 960

Tyr Gly Asp Leu Tyr Asn Glu Thr Ala Gln Tyr Met Gln Glu Lys Ser
            965                 970                 975

Ile Tyr Tyr Asp Ala Ile Thr Thr Leu Met Arg Ala Arg Lys Gln Phe
```

-continued

Val Ser Gly Gly Gln Thr Met Thr Lys Leu Asn Asn Asn Leu Leu Ala
    980             985             990
                995             1000            1005

Ser Val Arg Tyr Gly Lys Gly Val Val Asp Ala Asn Ser Asn Gly
    1010            1015            1020

Thr Asp Lys Leu Ser Arg Thr Ser Gly Met Ala Val Leu Val Gly
    1025            1030            1035

Asn Asp Ser Asn Met Ala Gln Gln Thr Val Ala Ile Asn Met Gly
    1040            1045            1050

Arg Val His Ala Asn Gln Gln Tyr Arg Asn Leu Ile Asp Thr Thr
    1055            1060            1065

Glu Asn Gly Leu Thr Tyr Asp Ala Lys Asn Ser Glu Asn Pro Ala
    1070            1075            1080

Ile Leu Thr Thr Asp Ser Asn Gly Ile Leu Lys Val Thr Val Lys
    1085            1090            1095

Gly Tyr Ser Asn Pro Tyr Val Ser Gly Tyr Leu Gly Val Trp Val
    1100            1105            1110

Pro Val Ile Ser Gly Asp Gln Asp Val Thr Thr Ser Val Ser Asp
    1115            1120            1125

Val Val Ala Asp Lys Glu Lys Thr Phe Glu Ser Asn Ala Ala Leu
    1130            1135            1140

Asp Ser His Met Ile Tyr Glu Asp Phe Ser Leu Phe Gln Pro Glu
    1145            1150            1155

Pro Thr Ser Val Glu Asn His Ala Tyr Asn Val Ile Ala Lys Asn
    1160            1165            1170

Ala Ser Leu Phe Ser Asp Leu Gly Ile Thr Asp Phe Trp Met Ala
    1175            1180            1185

Pro Ala Tyr Thr Pro Phe Gly Arg Ser Arg Tyr Lys Glu Gly Tyr
    1190            1195            1200

Ser Met Thr Asp Arg Tyr Asn Leu Gly Thr Thr Ala Asn Pro Thr
    1205            1210            1215

Lys Tyr Gly Ser Gly Glu Glu Leu Ala Asn Thr Ile Ala Ala Leu
    1220            1225            1230

His Lys Ala Gly Leu Lys Val Gln Glu Asp Ile Val Met Asn Gln
    1235            1240            1245

Met Ile Gly Phe Ser Gly Gln Glu Ala Val Thr Val Thr Arg Thr
    1250            1255            1260

Asn Asn Arg Gly Met Gln Ile His Val Asn Gly Lys Thr Tyr Ala
    1265            1270            1275

Asn Gln Ile Tyr Phe Ala Tyr Thr Thr Gly Gly Asn Gly Gln
    1280            1285            1290

Lys Thr Tyr Gly Gly Lys Tyr Leu Ser Glu Leu Gln Arg Asn Tyr
    1295            1300            1305

Pro Asp Leu Phe Thr Thr Lys Ala Val Ser Thr Gly Val Ala Pro
    1310            1315            1320

Asp Pro Thr Ile His Ile Asn Glu Trp Ser Ala Lys Tyr Glu Asn
    1325            1330            1335

Gly Thr Ser Leu Gln Asn Ile Gly Ile Gly Leu Ala Val Lys Leu
    1340            1345            1350

Pro Asn Gly Asp Tyr Ala Tyr Leu Asn Ser Gly Ile Asp Lys Ser
    1355            1360            1365

Phe Ser Thr Leu Leu Pro Ser Glu Ile Ala Pro Ile Phe Asn Asp
    1370            1375            1380

<210> SEQ ID NO 62
<211> LENGTH: 695
<212> TYPE: PRT
<213> ORGANISM: Lactobacillus reuteri

<400> SEQUENCE: 62

Trp Tyr Arg Pro Tyr Gly Thr Ser Gln Asp Gly Lys Thr Trp Tyr Glu
1               5                   10                  15

Thr Thr Ala Met Asp Trp Arg Pro Leu Leu Met Tyr Ile Trp Pro Ser
            20                  25                  30

Lys Asp Val Gln Ala Gln Phe Ile Lys Tyr Phe Val Asn Asn Gly Tyr
        35                  40                  45

Glu Asn Ala Asn Tyr Gly Leu Thr Lys Ser Ser Val Ala Ser Phe Ser
50                  55                  60

Lys Asp Thr Asn Ala Asn Leu Leu Asp Val Thr Ala Gln Asn Leu Arg
65                  70                  75                  80

Tyr Val Ile Glu Gln Ser Ile Ala Ala Asn Lys Gly Thr Ser Lys Leu
                85                  90                  95

Ala Asn Asp Ile Asn Ser Phe Ala Ala Thr Val Pro Glu Leu Ser Ala
            100                 105                 110

Ser Ser Glu Leu Ser Leu Gln Ser Met Pro Asn Tyr Arg Pro Asp Glu
        115                 120                 125

Ser Gly Thr Val Asp Ser Asp Gln Val Ile Phe Val Asn Asn Asn Ser
130                 135                 140

Lys Asp Pro Arg Lys Gly Asn Thr Ser Tyr Ala Asp Ser Asn Tyr Arg
145                 150                 155                 160

Leu Met Asn Arg Thr Ile Asn Asn Gln Ala Gly Asn Asn Ser Asp
                165                 170                 175

Asn Ser Pro Glu Leu Leu Val Gly Asn Asp Ile Asp Asn Ser Asn Pro
            180                 185                 190

Val Val Gln Ala Glu Asn Leu Asn Trp Glu Tyr Phe Leu Leu Asn Tyr
        195                 200                 205

Gly Lys Leu Met Gly Tyr Asn Pro Asp Gly Asn Phe Asp Gly Phe Arg
210                 215                 220

Val Asp Ala Ala Asp Asn Ile Asp Ala Asp Val Leu Asp Gln Met Gly
225                 230                 235                 240

Gln Leu Met Asn Asp Met Tyr His Thr Lys Gly Asn Pro Gln Asn Ala
                245                 250                 255

Asn Asp His Leu Ser Tyr Asn Glu Gly Tyr His Ser Gly Ala Ala Gln
            260                 265                 270

Met Leu Asn Glu Lys Gly Asn Pro Gln Leu Tyr Met Asp Ser Gly Glu
        275                 280                 285

Phe Tyr Thr Leu Glu Asn Val Leu Gly Arg Ala Asn Asn Arg Asp Asn
290                 295                 300

Ile Gly Asn Leu Ile Thr Asn Ser Ile Val Asn Arg Gln Asn Asp Thr
305                 310                 315                 320

Thr Glu Asn Glu Ala Thr Pro Asn Trp Ser Phe Val Thr Asn His Asp
                325                 330                 335

Gln Arg Lys Asn Leu Ile Asn Arg Leu Ile Ile Lys Asp His Ser Asn
            340                 345                 350

Ile Pro Asp Ile Met Gly Ser Ala Tyr Lys Val Glu Tyr Ala Asn Gln
        355                 360                 365

Ala Trp Gln Glu Phe Tyr Ala Asp Gln Glu Lys Thr Asn Lys Gln Tyr

```
                    370                 375                 380
Ala Gln Tyr Asn Val Pro Ala Gln Tyr Ala Ile Leu Leu Ser Asn Lys
385                 390                 395                 400

Asp Thr Val Pro Gln Val Tyr Tyr Gly Asp Leu Tyr Asn Glu Thr Ala
            405                 410                 415

Gln Tyr Met Gln Glu Lys Ser Ile Tyr Tyr Asp Ala Ile Thr Thr Leu
            420                 425                 430

Met Arg Ala Arg Lys Gln Phe Val Ser Gly Gln Thr Met Thr Lys
            435                 440                 445

Leu Asn Asn Asn Leu Leu Ala Ser Val Arg Tyr Gly Lys Gly Val Val
            450                 455                 460

Asp Ala Asn Ser Asn Gly Thr Asp Lys Leu Ser Arg Thr Ser Gly Met
465                 470                 475                 480

Ala Val Leu Val Gly Asn Asp Ser Asn Met Ala Gln Gln Thr Val Ala
            485                 490                 495

Ile Asn Met Gly Arg Val His Ala Asn Gln Gln Tyr Arg Asn Leu Ile
            500                 505                 510

Asp Thr Thr Glu Asn Gly Leu Thr Tyr Asp Ala Lys Asn Ser Glu Asn
            515                 520                 525

Pro Ala Ile Leu Thr Thr Asp Ser Asn Gly Ile Leu Lys Val Thr Val
            530                 535                 540

Lys Gly Tyr Ser Asn Pro Tyr Val Ser Gly Tyr Leu Gly Val Trp Val
545                 550                 555                 560

Pro Val Ile Ser Gly Asp Gln Asp Val Thr Thr Ser Val Ser Asp Val
            565                 570                 575

Val Ala Asp Lys Glu Lys Thr Phe Glu Ser Asn Ala Ala Leu Asp Ser
            580                 585                 590

His Met Ile Tyr Glu Asp Phe Ser Leu Phe Gln Pro Glu Pro Thr Ser
            595                 600                 605

Val Glu Asn His Ala Tyr Asn Val Ile Ala Lys Asn Ala Ser Leu Phe
            610                 615                 620

Ser Asp Leu Gly Ile Thr Asp Phe Trp Met Ala Pro Ala Tyr Thr Pro
625                 630                 635                 640

Phe Gly Arg Ser Arg Tyr Lys Glu Gly Tyr Ser Met Thr Asp Arg Tyr
            645                 650                 655

Asn Leu Gly Thr Thr Ala Asn Pro Thr Lys Tyr Gly Ser Gly Glu Glu
            660                 665                 670

Leu Ala Asn Thr Ile Ala Ala Leu His Lys Ala Gly Leu Lys Val Gln
            675                 680                 685

Glu Asp Ile Val Met Asn Gln
            690                 695

<210> SEQ ID NO 63
<211> LENGTH: 1620
<212> TYPE: PRT
<213> ORGANISM: Lactobacillus reuteri

<400> SEQUENCE: 63

Met Glu Ile Lys Lys His Phe Lys Leu Tyr Lys Ser Gly Lys Gln Trp
1               5                   10                  15

Val Thr Ala Ser Ile Ala Thr Phe Ala Val Ser Thr Gly Leu Val Leu
            20                  25                  30

Gly Gly Gly Val Val His Ala Ala Asp Asn His Pro Thr Thr Thr Ser
            35                  40                  45
```

```
Ala Ser Val Thr Asn Thr Val Asn Asn Leu Lys Pro Gln Asn Asp Pro
 50                  55                  60

Glu Gln Gln Asn Thr Gln Glu Ser Asn Thr Val Glu Phe Pro Lys
 65                  70                  75                  80

Lys Asp Ser Gln Asp Asn Ala Val Gln Pro Leu Lys Glu Thr Ala Val
                 85                  90                  95

Met Pro Asn Ala Thr Asn Lys Asp Gly Ala Lys Ala Ser Ile Thr Asn
                100                 105                 110

Asn Ala His Thr Asp Asn Thr Ile Tyr Gly Asn Ile Asp Pro Thr Thr
                115                 120                 125

Ile Asn Asp Lys Glu Leu His Val Thr Gly Trp Asn Ala Thr Asn Gln
130                 135                 140

Ala Ile Asn Lys Asn Glu Ser Arg Tyr Val Ile Ala Tyr Asp Asp Thr
145                 150                 155                 160

Thr Asn Ser Glu Leu Gly Arg Thr Lys Ile Thr Asn Gln Ile Ala Arg
                165                 170                 175

Pro Asp Val Glu Lys Val His Lys Asp Ile Tyr Asn Ala Gln Asn Ser
                180                 185                 190

Gly Phe Asn Val Asn Ile Ser Leu Asp Phe Asn Lys Met Asn Asn Tyr
                195                 200                 205

Arg Asp Ala Ile Lys Ile Ile Ser Arg Tyr Ser Gly Val Pro Asn Gly
                210                 215                 220

Asn Ser Asp Tyr Val Asp Phe Val Ser Gln Pro Ile Ile Phe Asp Glu
225                 230                 235                 240

Asn Asn Tyr Ala Tyr Leu Asp Asp Phe Ser Val Gln Asn Gly Arg Leu
                245                 250                 255

His Val Ser Gly Arg Asn Ala Thr Asn Lys Ala Ile Gln Arg Pro Asn
                260                 265                 270

His Phe Leu Ile Leu Phe Asp Arg Thr Val Asn Arg Glu Val Ala Arg
                275                 280                 285

Gln Lys Val Thr Ala Gly Ile Asn Arg Ser Asp Val Glu Lys Val Tyr
                290                 295                 300

Pro Gln Val Val Asn Ala Asn Val Ser Gly Phe Asp Ala Thr Phe Asp
305                 310                 315                 320

Thr Ile Asn Leu Asn Pro Asn His Glu Tyr Gln Ile Leu Ser Arg Tyr
                325                 330                 335

Ser Asn Asn Gly Asp Gly Glu Gly Asp Tyr Val Thr Tyr Trp Phe Asn
                340                 345                 350

Pro Gln Arg Ile Ala Pro Val Asn Gln Phe Asn Asn Gly His Leu Asp
                355                 360                 365

Asn Phe Asp Ile Ser Lys Ala Gly Lys Val Thr Val Ser Gly Trp Gln
                370                 375                 380

Ala Thr Asn Leu Ser Asn Ile Gln Asn Asn Arg Tyr Ile Ile Leu Phe
385                 390                 395                 400

Asp Thr Thr Ala Asn Cys Gln Ile Ala Ser Met Lys Val Thr Gly Val
                405                 410                 415

Asp Arg Pro Asp Val Ala Lys Val Tyr Pro Gln Ile Leu Asn Ala Asn
                420                 425                 430

Lys Ser Gly Tyr Asn Val Thr Phe Asp Leu Thr Gln Ala Gln Ile Ala
                435                 440                 445

Gln Leu Phe Pro Asn His Ser Tyr Ser Ile Val Ser Arg Tyr Ser Ala
                450                 455                 460

Asp Pro Asn Gly Asn Gly Asn Asp Lys Gln His Thr Asp Phe Trp Ser
```

-continued

```
            465                 470                 475                 480
        Ala Pro Ile Val Leu Asn Lys Thr Ala Ser Tyr Ile Asp Asp Ile Ser
                        485                 490                 495

Leu Asn Gly Asp Val Leu Asn Val Lys Gly Trp Met Ala Ser Asp Ala
                        500                 505                 510

Ser Ala Thr Gln Ala Asn Pro Tyr Ile Ile Leu Asn Asn Gly Lys
                        515                 520                 525

Glu Val Thr Arg Gln Lys Leu Thr Leu Asn Asp Arg Pro Asp Val Ala
                        530                 535                 540

Lys Val Tyr Pro Asp Val Tyr Asn Ser Leu Ala Ser Gly Phe Asp Thr
        545                 550                 555                 560

Thr Ile Lys Leu Thr Asn Ser Gln Leu Asn Ala Leu Asn Gly Asn Met
                        565                 570                 575

Gln Ile Leu Leu Arg Tyr Ser Ala Ala Asp Gly Asn Pro Ile Asn
                        580                 585                 590

Asn Gly Gly Phe Thr Asp Gln Tyr Ser Lys Asn Tyr Ala Thr Asn Gly
                        595                 600                 605

Gly Ser Phe Asp Phe Val Lys Val Asp Asn Asn Gln Val Ala Phe Ser
                        610                 615                 620

Gly Trp His Val Ser Asp Gln Ala Thr Asp Lys Pro Tyr Gln Trp Ile
        625                 630                 635                 640

Ile Val Leu Val Asn Gly Lys Glu Val Gly Arg Gln Leu Ile Ser Ser
                        645                 650                 655

Thr Thr Asn Gly Leu Val Ser Tyr Asn Arg Pro Asp Val Tyr Asn Val
                        660                 665                 670

Asn Pro Ala Ile Ser Asn Ser Thr Ser Gly Phe Gln Gly Ile Met
                        675                 680                 685

Thr Leu Lys Asp Asn Ile Lys Asn Ala Asn Val Gln Leu Val His Arg
                        690                 695                 700

Phe Ser Asp Asp Gly Gln Asn Gly Glu Gly Asn Arg Val Asp Tyr Trp
        705                 710                 715                 720

Ser Glu Val Met Pro Val Thr Asn Thr Phe Gln Lys Gly Thr Asp Gln
                        725                 730                 735

Leu Met Arg Asn Leu Val Ala Lys Pro Asn Lys Asn Gln Leu Lys Ile
                        740                 745                 750

Tyr Asn Gly Asn Thr Leu Val Lys Thr Leu Gly Pro Gly Thr Trp Glu
                        755                 760                 765

Asn Met Ala Phe Ala Gln Asp Ser Ser Ala Ile Asn Asn Ile Asp Gly
                        770                 775                 780

Tyr Leu Ser Tyr Thr Gly Trp Tyr Arg Pro Tyr Gly Thr Ser Gln Asp
        785                 790                 795                 800

Gly Lys Thr Trp Tyr Glu Thr Thr Ala Met Asp Trp Arg Pro Leu Leu
                        805                 810                 815

Met Tyr Ile Trp Pro Ser Lys Asp Val Gln Ala Gln Phe Ile Lys Tyr
                        820                 825                 830

Phe Val Asn Asn Gly Tyr Glu Asn Ala Asn Tyr Gly Leu Thr Glu Ser
                        835                 840                 845

Ser Val Ala Ser Phe Ser Lys Asp Thr Asn Ala Asn Leu Leu Asp Val
                        850                 855                 860

Thr Ala Gln Asn Leu Arg Tyr Val Ile Glu Gln Ser Ile Ala Ala Asn
        865                 870                 875                 880

Lys Gly Thr Ser Lys Leu Ala Asn Asp Ile Asn Ser Phe Ala Ala Thr
                        885                 890                 895
```

-continued

Val Pro Glu Leu Ser Ala Ser Ser Glu Leu Ser Leu Gln Ser Met Pro
            900                 905                 910

Asn Tyr Arg Pro Asp Glu Ser Gly Thr Val Asp Ser Asp Gln Val Ile
            915                 920                 925

Phe Val Asn Asn Ser Lys Asp Pro Arg Lys Gly Asn Thr Gly Tyr
            930                 935                 940

Ala Asp Ser Asn Tyr Arg Leu Met Asn Arg Thr Ile Asn Asn Gln Ala
945                 950                 955                 960

Gly Asn Asn Asn Ser Asp Asn Ser Pro Glu Leu Leu Val Gly Asn Asp
                965                 970                 975

Ile Asp Asn Ser Asn Pro Val Val Gln Ala Glu Asn Leu Asn Trp Glu
            980                 985                 990

Tyr Phe Leu Leu Asn Tyr Gly Lys Leu Met Gly Tyr Asn Pro Asp Gly
            995                 1000                1005

Asn Phe Asp Gly Phe Arg Val Asp Ala Ala Asp Asn Ile Asp Ala
            1010                1015            1020

Asp Val Leu Asp Gln Met Gly Gln Leu Met Asn Asp Met Tyr His
            1025            1030                1035

Thr Lys Gly Asn Pro Gln Asn Ala Asn Asp His Leu Ser Tyr Asn
            1040            1045                1050

Glu Gly Tyr His Ser Gly Ala Ala Gln Met Leu Asn Glu Lys Gly
            1055            1060                1065

Asn Pro Gln Leu Tyr Met Asp Ser Gly Glu Phe Tyr Thr Leu Glu
            1070            1075                1080

Asn Val Leu Gly Arg Ala Asn Asn Arg Asp Ser Ile Gly Asn Leu
            1085            1090                1095

Ile Thr Asn Ser Val Val Asn Arg Gln Asn Asp Thr Thr Glu Asn
            1100            1105                1110

Glu Ala Thr Pro Asn Trp Ser Phe Val Thr Asn His Asp Gln Arg
            1115            1120                1125

Lys Asn Leu Ile Asn Arg Leu Ile Ile Lys Gly His Pro Asn Ile
            1130            1135                1140

Pro Asp Ile Met Gly Ser Ala Tyr Lys Ala Glu Tyr Ala Asn Gln
            1145            1150                1155

Ala Trp Gln Glu Phe Tyr Ala Asp Gln Lys Lys Thr Asn Lys Gln
            1160            1165                1170

Tyr Asp Gln Tyr Asn Val Pro Ala Gln Tyr Ala Ile Leu Leu Ser
            1175            1180                1185

Asn Lys Asp Thr Val Pro Gln Val Tyr Tyr Gly Asp Leu Tyr Asn
            1190            1195                1200

Glu Thr Ala Gln Tyr Met Gln Glu Lys Ser Ile Tyr Tyr Asp Thr
            1205            1210                1215

Ile Thr Thr Leu Met Lys Ala Arg Lys Gln Phe Val Ser Gly Gly
            1220            1225                1230

Gln Thr Met Thr Lys Leu Asn Asn Asn Leu Leu Ala Ser Val Arg
            1235            1240                1245

Tyr Gly Lys Gly Val Ala Asp Ser Asn Ser Asn Gly Thr Asp Lys
            1250            1255                1260

Leu Ser Arg Thr Ser Gly Ile Ala Val Leu Val Gly Asn Asp Ser
            1265            1270                1275

Asn Met Ala Gln Gln Thr Val Ala Ile Asn Met Gly Arg Ala His
            1280            1285                1290

-continued

```
Ala Asn Gln Gln Tyr Arg Asn Leu Ile Asp Thr Thr Glu Asn Gly
    1295                1300                1305

Leu Thr Tyr Asp Gly Glu Asn Ser Glu Asn Pro Ala Ile Leu Thr
    1310                1315                1320

Thr Asp Ser Asn Gly Ile Leu Lys Val Thr Val Lys Gly Tyr Ser
    1325                1330                1335

Asn Pro Tyr Val Ser Gly Tyr Leu Gly Val Trp Val Pro Val Ile
    1340                1345                1350

Ser Gly Asp Gln Asp Val Thr Thr Ser Ala Ser Asp Val Val Ala
    1355                1360                1365

Asp Lys Glu Lys Thr Phe Glu Ser Asn Ala Ala Leu Asp Ser His
    1370                1375                1380

Met Ile Tyr Glu Asp Phe Ser Leu Phe Gln Pro Glu Pro Thr Asn
    1385                1390                1395

Val Glu Asn His Ala Tyr Asn Val Ile Ala Lys Asn Ala Asn Leu
    1400                1405                1410

Phe Asn Asp Leu Gly Ile Thr Asp Phe Trp Met Ala Pro Ala Tyr
    1415                1420                1425

Thr Pro Phe Gly Met Ser Arg Tyr Asn Glu Gly Tyr Ser Met Thr
    1430                1435                1440

Asp Arg Tyr Asn Leu Gly Thr Thr Ala Asn Pro Thr Lys Tyr Gly
    1445                1450                1455

Ser Gly Glu Glu Leu Ala Asn Thr Ile Ala Ala Leu His Lys Val
    1460                1465                1470

Gly Leu Lys Val Gln Glu Asp Ile Val Met Asn Gln Met Ile Gly
    1475                1480                1485

Phe Ser Gly Gln Glu Ala Val Thr Val Thr Arg Thr Asn Asn Arg
    1490                1495                1500

Gly Met Gln Ile His Val Asn Gly Gln Thr Tyr Ala Asn Gln Ile
    1505                1510                1515

Tyr Phe Ala Tyr Thr Thr Gly Gly Gly Asn Gly Gln Glu Thr Tyr
    1520                1525                1530

Gly Gly Lys Tyr Leu Ala Glu Leu Gln Lys Asn Tyr Pro Asp Leu
    1535                1540                1545

Phe Thr Thr Lys Ala Ile Ser Thr Glu Val Val Pro Asp Pro Thr
    1550                1555                1560

Val Arg Ile Asn Lys Trp Ser Ala Lys Tyr Glu Asn Gly Thr Ser
    1565                1570                1575

Leu Gln Asn Ile Gly Ile Gly Leu Ala Val Lys Leu Ala Asn Gly
    1580                1585                1590

Asp Tyr Ala Tyr Leu Asn Ser Gly Asp Asn Lys Ala Phe Asn Thr
    1595                1600                1605

Leu Leu Pro Thr Ala Ile Ser Leu Asn Phe Asn Asn
    1610                1615                1620

<210> SEQ ID NO 64
<211> LENGTH: 695
<212> TYPE: PRT
<213> ORGANISM: Lactobacillus reuteri

<400> SEQUENCE: 64

Trp Tyr Arg Pro Tyr Gly Thr Ser Gln Asp Gly Lys Thr Trp Tyr Glu
1               5                   10                  15

Thr Thr Ala Met Asp Trp Arg Pro Leu Leu Met Tyr Ile Trp Pro Ser
            20                  25                  30
```

-continued

```
Lys Asp Val Gln Ala Gln Phe Ile Lys Tyr Phe Val Asn Asn Gly Tyr
         35                  40                  45

Glu Asn Ala Asn Tyr Gly Leu Thr Glu Ser Ser Val Ala Ser Phe Ser
 50                  55                  60

Lys Asp Thr Asn Ala Asn Leu Leu Asp Val Thr Ala Gln Asn Leu Arg
 65                  70                  75                  80

Tyr Val Ile Glu Gln Ser Ile Ala Ala Asn Lys Gly Thr Ser Lys Leu
                 85                  90                  95

Ala Asn Asp Ile Asn Ser Phe Ala Ala Thr Val Pro Glu Leu Ser Ala
                100                 105                 110

Ser Ser Glu Leu Ser Leu Gln Ser Met Pro Asn Tyr Arg Pro Asp Glu
            115                 120                 125

Ser Gly Thr Val Asp Ser Asp Gln Val Ile Phe Val Asn Asn Asn Ser
130                 135                 140

Lys Asp Pro Arg Lys Gly Asn Thr Gly Tyr Ala Asp Ser Asn Tyr Arg
145                 150                 155                 160

Leu Met Asn Arg Thr Ile Asn Asn Gln Ala Gly Asn Asn Ser Asp
                165                 170                 175

Asn Ser Pro Glu Leu Leu Val Gly Asn Asp Ile Asp Asn Ser Asn Pro
                180                 185                 190

Val Val Gln Ala Glu Asn Leu Asn Trp Glu Tyr Phe Leu Leu Asn Tyr
                195                 200                 205

Gly Lys Leu Met Gly Tyr Asn Pro Asp Gly Asn Phe Asp Gly Phe Arg
210                 215                 220

Val Asp Ala Ala Asp Asn Ile Asp Ala Asp Val Leu Asp Gln Met Gly
225                 230                 235                 240

Gln Leu Met Asn Asp Met Tyr His Thr Lys Gly Asn Pro Gln Asn Ala
                245                 250                 255

Asn Asp His Leu Ser Tyr Asn Glu Gly Tyr His Ser Gly Ala Ala Gln
                260                 265                 270

Met Leu Asn Glu Lys Gly Asn Pro Gln Leu Tyr Met Asp Ser Gly Glu
                275                 280                 285

Phe Tyr Thr Leu Glu Asn Val Leu Gly Arg Ala Asn Asn Arg Asp Ser
290                 295                 300

Ile Gly Asn Leu Ile Thr Asn Ser Val Val Asn Arg Gln Asn Asp Thr
305                 310                 315                 320

Thr Glu Asn Glu Ala Thr Pro Asn Trp Ser Phe Val Thr Asn His Asp
                325                 330                 335

Gln Arg Lys Asn Leu Ile Asn Arg Leu Ile Ile Lys Gly His Pro Asn
                340                 345                 350

Ile Pro Asp Ile Met Gly Ser Ala Tyr Lys Ala Glu Tyr Ala Asn Gln
                355                 360                 365

Ala Trp Gln Glu Phe Tyr Ala Asp Gln Lys Thr Asn Lys Gln Tyr
370                 375                 380

Asp Gln Tyr Asn Val Pro Ala Gln Tyr Ala Ile Leu Leu Ser Asn Lys
385                 390                 395                 400

Asp Thr Val Pro Gln Val Tyr Tyr Gly Asp Leu Tyr Asn Glu Thr Ala
                405                 410                 415

Gln Tyr Met Gln Glu Lys Ser Ile Tyr Tyr Asp Thr Ile Thr Thr Leu
                420                 425                 430

Met Lys Ala Arg Lys Gln Phe Val Ser Gly Gly Gln Thr Met Thr Lys
                435                 440                 445
```

Leu Asn Asn Asn Leu Leu Ala Ser Val Arg Tyr Gly Lys Gly Val Ala
        450                 455                 460

Asp Ser Asn Ser Asn Gly Thr Asp Lys Leu Ser Arg Thr Ser Gly Ile
465                 470                 475                 480

Ala Val Leu Val Gly Asn Asp Ser Asn Met Ala Gln Gln Thr Val Ala
            485                 490                 495

Ile Asn Met Gly Arg Ala His Ala Asn Gln Gln Tyr Arg Asn Leu Ile
        500                 505                 510

Asp Thr Thr Glu Asn Gly Leu Thr Tyr Asp Gly Glu Asn Ser Glu Asn
    515                 520                 525

Pro Ala Ile Leu Thr Thr Asp Ser Asn Gly Ile Leu Lys Val Thr Val
530                 535                 540

Lys Gly Tyr Ser Asn Pro Tyr Val Ser Gly Tyr Leu Gly Val Trp Val
545                 550                 555                 560

Pro Val Ile Ser Gly Asp Gln Asp Val Thr Thr Ser Ala Ser Asp Val
            565                 570                 575

Val Ala Asp Lys Glu Lys Thr Phe Glu Ser Asn Ala Ala Leu Asp Ser
        580                 585                 590

His Met Ile Tyr Glu Asp Phe Ser Leu Phe Gln Pro Glu Pro Thr Asn
    595                 600                 605

Val Glu Asn His Ala Tyr Asn Val Ile Ala Lys Asn Ala Asn Leu Phe
610                 615                 620

Asn Asp Leu Gly Ile Thr Asp Phe Trp Met Ala Pro Ala Tyr Thr Pro
625                 630                 635                 640

Phe Gly Met Ser Arg Tyr Asn Glu Gly Tyr Ser Met Thr Asp Arg Tyr
            645                 650                 655

Asn Leu Gly Thr Thr Ala Asn Pro Thr Lys Tyr Gly Ser Gly Glu Glu
        660                 665                 670

Leu Ala Asn Thr Ile Ala Ala Leu His Lys Val Gly Leu Lys Val Gln
    675                 680                 685

Glu Asp Ile Val Met Asn Gln
    690                 695

<210> SEQ ID NO 65
<211> LENGTH: 1363
<212> TYPE: PRT
<213> ORGANISM: Lactobacillus reuteri

<400> SEQUENCE: 65

Met Asn Leu Pro Thr Ile Pro Asn Thr Asn Val Gln Thr Asp Asn Asn
1               5                   10                  15

Trp Tyr Leu Val Asp Asn Gly Ile Ala Gln Ser Gly Val Gln Gln Trp
            20                  25                  30

Ala Gly Ser Tyr Tyr Tyr Phe Asn Pro Ser Thr Tyr Leu Arg Val Asp
        35                  40                  45

Asn Glu Tyr Arg Gln Ser Gln Trp Gly Asp Trp Tyr Met Phe Gly Lys
    50                  55                  60

Asp Gly Arg Ala Val Thr Gly Leu Tyr Asp Tyr Asn Gly Asn Thr Tyr
65                  70                  75                  80

Tyr Ala Asn Pro Thr Thr Tyr Leu Arg Glu Thr Asn Lys Tyr Ile Ser
            85                  90                  95

Thr Ser Lys Gly Asn Met Leu Leu Gly Asn Asp Gly Ala Ala Leu Ser
        100                 105                 110

Gly Ile Gln Ser Val Asn Gly Lys Tyr Tyr Tyr Phe Asp Pro Val Thr
    115                 120                 125

His Leu Gln Ala Asn Lys Glu Asn Tyr Val Gln Ser Gln Trp Gly Asp
    130                 135                 140

Trp Tyr Leu Ile Gly Asn Asp Gly Gln Val Leu Ser Gly Val Gln Gln
145                 150                 155                 160

Trp Ala Gly Thr Tyr Tyr Tyr Phe Asp Pro Thr Thr Tyr Leu Arg Val
                165                 170                 175

Asp Asn Asp Tyr Arg Gln Ser Gln Trp Gly Leu Trp Tyr Met Phe Gly
            180                 185                 190

His Asp Gly Arg Ile Val Thr Lys Val Tyr Pro Trp Ala Gly Thr Tyr
        195                 200                 205

Tyr Tyr Phe Asp Pro Thr Thr Tyr Leu Arg Val Asp Asn Ala Tyr Leu
    210                 215                 220

Gln Ser Gln Trp Gly Asp Trp Tyr Leu Phe Gly Asn Asp Gly Arg Ile
225                 230                 235                 240

Gln Ser Gly Val Gln Arg Trp Ala Gly Thr Tyr Tyr Tyr Phe Asp Pro
                245                 250                 255

Thr Thr Tyr Leu Arg Val Asp Asn Asp Tyr Val Thr Ser Gln Trp Gly
            260                 265                 270

Ser Lys Tyr Met Phe Gly Pro Asp Gly Arg Ile Val Thr Gly Leu Tyr
        275                 280                 285

Lys Trp Ser Lys Asn Asn Gln Leu Tyr Phe Asp Pro Val Thr Tyr
    290                 295                 300

Leu Ala Val Thr Asn Asn Tyr Ile Lys Ala Asn Asn Gly Asn Trp Tyr
305                 310                 315                 320

Leu Phe Thr Ala Asp Gly Thr Ala Ala Ser Lys Val Ala Pro Trp Ala
                325                 330                 335

Gly Ser Tyr Tyr Tyr Phe Asp Pro Val Thr His Leu Arg Val Asp Asn
            340                 345                 350

Ala Tyr Val Gln Ser Gln Trp Gly Asp Trp Tyr Met Phe Gly Pro Asp
        355                 360                 365

Gly Arg Ile Val Thr Gly Leu Lys Glu Trp Tyr Gly Ser Tyr Tyr Tyr
    370                 375                 380

Phe Asp Pro Thr Thr Tyr Leu Lys Val Thr Asn Lys Trp Ile Asp Asn
385                 390                 395                 400

Lys Tyr Phe Gly Pro Asp Gly Arg Gln Ala Ile Ser Ser Leu Glu Asn
                405                 410                 415

Ile Asn Asn Lys Phe Tyr Cys Phe Asp Gly Asn Gly Gln Ile Ile Arg
            420                 425                 430

Asn Gln Phe Lys Lys Ile Asp Thr His Thr Tyr Tyr Phe Gly Ser Asp
        435                 440                 445

Gly Ala Ala Leu Val Gly Lys Gln Thr Ile Asp Gly Lys Asn Tyr His
    450                 455                 460

Phe Ala Ser Asn Gly Gln Leu Leu Gly Asn Leu Tyr Gly Lys Ile Val
465                 470                 475                 480

Asp Gly Lys Phe Asn Ile Tyr Asp Ser Leu Ser Asn Lys Leu Ile Lys
                485                 490                 495

Thr Leu Asp Ser Gly Asp Trp Glu Asn Met Ala Tyr Ser Gln Asp Ser
            500                 505                 510

Ser Ser Ile Asn Asn Thr Asp Gly Tyr Leu Ser Tyr Ser Gly Trp Tyr
        515                 520                 525

Arg Pro Tyr Gly Thr Ser Gln Asp Gly Lys Thr Trp Tyr Lys Thr Thr
    530                 535                 540

-continued

```
Ala Ser Asp Trp Arg Pro Leu Leu Met Tyr Thr Trp Pro Ser Lys Asp
545                 550                 555                 560

Val Glu Ala Lys Phe Ile Lys Tyr Phe Val Asp Asn Gly Tyr Thr Asn
            565                 570                 575

Thr Asp Tyr Gly Leu Thr Lys Asp Asn Val Thr Asn Leu Ser Gln Asp
        580                 585                 590

Thr Asp Thr Gln Thr Leu Asn Lys Tyr Ala Arg Asn Leu Arg Phe Val
    595                 600                 605

Ile Glu Lys Ser Ile Ala Ala Asn Lys Ser Thr Gly Pro Leu Ala Asn
610                 615                 620

Asp Ile Asn Lys Phe Met Leu Thr Ile Pro Glu Leu Ser Ala Lys Ser
625                 630                 635                 640

Glu Leu Pro Val Glu Tyr Ser Asn Gly Tyr Val Pro Asp Val Ser Gly
            645                 650                 655

Ser Ile Asp Asn Asn Gln Leu Ile Phe Ile Asn Asn Ser Asp Asn
        660                 665                 670

Gln Ala Lys Gly Asn Thr Ser Tyr Ala Asp Ser Asn Tyr Arg Leu Met
    675                 680                 685

Asn Arg Thr Ile Asn Asn Gln Thr Asn Asn Asp Asn Ser Asp Gln Ser
690                 695                 700

Pro Glu Leu Leu Val Gly Asn Asp Ile Asp Asn Ser Asn Pro Ala Val
705                 710                 715                 720

Gln Ala Glu Asn Phe Asn Trp Glu Tyr Phe Leu Leu Asn Tyr Gly Lys
            725                 730                 735

Leu Met Lys Tyr Asn Ala Asp Gly Asn Phe Asp Gly Phe Arg Val Asp
        740                 745                 750

Ala Ala Asp Asn Ile Asp Ala Asp Val Leu Asp Gln Leu Gly Gln Leu
    755                 760                 765

Val Asn Asp Met Tyr His Thr Lys Gly Asn Gln Glu Asn Ala Asn Asn
770                 775                 780

His Leu Val Tyr Asn Glu Gly Tyr His Ser Gly Ala Ala Arg Met Leu
785                 790                 795                 800

Asn Asp Lys Gly Asn Pro Glu Leu Phe Met Asp Ala Gly Tyr Phe Tyr
            805                 810                 815

Thr Leu Glu Asn Val Leu Gly Gln Ala Glu Asn Lys Arg Asp Asn Val
        820                 825                 830

Asn Asn Leu Ile Thr Asn Ser Val Val Asn Arg Ala Asn Asp Ile Thr
    835                 840                 845

Glu Asn Thr Ala Thr Pro Asn Trp Ser Phe Val Thr Asn His Asp Gln
850                 855                 860

Arg Lys Asn Val Ile Asn Gln Ile Ile Asp Asn His Pro Asn Ile
865                 870                 875                 880

Pro Asp Ile Met Ala Asn Ser Tyr Lys Ser Thr Tyr Ala Gln Lys Ala
            885                 890                 895

Trp Asp Glu Phe Tyr Ala Asp Gln Ala Lys Ala Asp Lys Lys Tyr Ala
        900                 905                 910

Gln Tyr Asn Leu Pro Ala Gln Tyr Ala Leu Leu Ser Asn Lys Asp
    915                 920                 925

Thr Val Pro Gln Val Tyr Gly Asp Leu Tyr Lys Glu Thr Asp Gln
930                 935                 940

Tyr Met Lys Thr Lys Ser Met Tyr Tyr Asp Ala Ile Thr Thr Leu Met
945                 950                 955                 960

Lys Ala Arg Gly Glu Phe Val Asn Gly Gly Gln Thr Met Thr Lys Val
```

-continued

```
                965                 970                 975
Asn Asp Asn Leu Ile Thr Ser Val Arg Tyr Gly Lys Gly Val Val Asp
            980                 985                 990
Val Ser Ser Asn Gly Thr Asp Pro Leu Ser Arg Thr Thr Gly Met Ala
        995                1000                1005
Val Ile Val Gly Asn Asn Pro Ser Met Ser Glu Gln Val Val Ala
    1010                1015                1020
Ile Asn Met Gly Leu Ala His Ala Asn Glu Gln Tyr Arg Asn Leu
    1025                1030                1035
Ile Asp Ser Thr Ala Asp Gly Leu Thr Tyr Asn Ser Asn Gly Ser
    1040                1045                1050
Val Asn Pro Ser Val Leu Thr Thr Asp Ser Lys Gly Ile Leu Arg
    1055                1060                1065
Val Thr Val Lys Gly Tyr Ser Asn Pro Tyr Val Ser Gly Tyr Leu
    1070                1075                1080
Ser Val Trp Val Pro Leu Ile Asn Gly Thr Gln Asn Ala Arg Thr
    1085                1090                1095
Ser Ala Gln Glu Val Arg Asn Val Pro Gly Lys Val Phe Thr Ser
    1100                1105                1110
Asn Ala Ala Leu Asp Ser His Met Ile Tyr Glu Asp Phe Ser Leu
    1115                1120                1125
Phe Gln Pro Glu Pro Thr Thr Val Asn Glu His Ala Tyr Asn Val
    1130                1135                1140
Ile Lys Asp Asn Val Ala Leu Phe Asn Gln Leu Gly Ile Thr Asp
    1145                1150                1155
Phe Trp Met Ala Pro Ser Tyr Thr Pro Phe Asn Thr Ser Arg Tyr
    1160                1165                1170
Asn Glu Gly Tyr Ala Met Thr Asp Arg Tyr Asn Leu Gly Thr Ala
    1175                1180                1185
Asp Asn Pro Thr Lys Tyr Gly Asn Gly Glu Glu Leu Ser Asn Ala
    1190                1195                1200
Ile Ala Ala Leu His Gln Ala Gly Leu Lys Val Gln Glu Asp Leu
    1205                1210                1215
Val Met Asn Gln Met Ile Gly Phe Ser Thr Gln Glu Ala Val Thr
    1220                1225                1230
Val Thr Arg Val Asp Arg Asp Ala Lys Gln Leu Ser Val Asp Gly
    1235                1240                1245
Gln Thr Phe Ala Asp Gln Ile Tyr Phe Gly Tyr Thr Arg Gly Gly
    1250                1255                1260
Gly Gln Gly Gln Gln Asp Tyr Gly Gly Lys Tyr Leu Ala Glu Leu
    1265                1270                1275
Lys Gln Lys Tyr Pro Asp Leu Phe Thr Thr Lys Ala Ala Ser Thr
    1280                1285                1290
Gly Val Ala Pro Asp Pro Asn Thr Arg Ile Thr Glu Trp Ser Ala
    1295                1300                1305
Lys Tyr Glu Asn Gly Thr Ser Leu Gln Asn Val Gly Ile Gly Leu
    1310                1315                1320
Ala Val Lys Met Pro Asn Gly Tyr Tyr Ala Tyr Leu Asn Asp Gly
    1325                1330                1335
Asn Asn Lys Ala Phe Ala Thr Thr Leu Pro Asp Ala Ile Ser Ser
    1340                1345                1350
Ala Asp Tyr Tyr Ala Asn Gln Glu Asn Ile
    1355                1360
```

<210> SEQ ID NO 66
<211> LENGTH: 696
<212> TYPE: PRT
<213> ORGANISM: Lactobacillus reuteri

<400> SEQUENCE: 66

```
Trp Tyr Arg Pro Tyr Gly Thr Ser Gln Asp Gly Lys Thr Trp Tyr Lys
1               5                   10                  15

Thr Thr Ala Ser Asp Trp Arg Pro Leu Leu Met Tyr Thr Trp Pro Ser
            20                  25                  30

Lys Asp Val Glu Ala Lys Phe Ile Lys Tyr Phe Val Asp Asn Gly Tyr
        35                  40                  45

Thr Asn Thr Asp Tyr Gly Leu Thr Lys Asp Asn Val Thr Asn Leu Ser
    50                  55                  60

Gln Asp Thr Asp Thr Gln Thr Leu Asn Lys Tyr Ala Arg Asn Leu Arg
65                  70                  75                  80

Phe Val Ile Glu Lys Ser Ile Ala Ala Asn Lys Ser Thr Gly Pro Leu
                85                  90                  95

Ala Asn Asp Ile Asn Lys Phe Met Leu Thr Ile Pro Glu Leu Ser Ala
            100                 105                 110

Lys Ser Glu Leu Pro Val Glu Tyr Ser Asn Gly Tyr Val Pro Asp Val
        115                 120                 125

Ser Gly Ser Ile Asp Asn Asn Gln Leu Ile Phe Ile Asn Asn Asn Ser
    130                 135                 140

Asp Asn Gln Ala Lys Gly Asn Thr Ser Tyr Ala Asp Ser Asn Tyr Arg
145                 150                 155                 160

Leu Met Asn Arg Thr Ile Asn Asn Gln Thr Asn Asn Asp Asn Ser Asp
                165                 170                 175

Gln Ser Pro Glu Leu Leu Val Gly Asn Asp Ile Asp Asn Ser Asn Pro
            180                 185                 190

Ala Val Gln Ala Glu Asn Phe Asn Trp Glu Tyr Phe Leu Leu Asn Tyr
        195                 200                 205

Gly Lys Leu Met Lys Tyr Asn Ala Asp Gly Asn Phe Asp Gly Phe Arg
    210                 215                 220

Val Asp Ala Ala Asp Asn Ile Asp Ala Asp Val Leu Asp Gln Leu Gly
225                 230                 235                 240

Gln Leu Val Asn Asp Met Tyr His Thr Lys Gly Asn Gln Glu Asn Ala
                245                 250                 255

Asn Asn His Leu Val Tyr Asn Glu Gly Tyr His Ser Gly Ala Ala Arg
            260                 265                 270

Met Leu Asn Asp Lys Gly Asn Pro Glu Leu Phe Met Asp Ala Gly Tyr
        275                 280                 285

Phe Tyr Thr Leu Glu Asn Val Leu Gly Gln Ala Glu Asn Lys Arg Asp
    290                 295                 300

Asn Val Asn Asn Leu Ile Thr Asn Ser Val Val Asn Arg Ala Asn Asp
305                 310                 315                 320

Ile Thr Glu Asn Thr Ala Thr Pro Asn Trp Ser Phe Val Thr Asn His
                325                 330                 335

Asp Gln Arg Lys Asn Val Ile Asn Gln Ile Ile Asp Asn His Pro
            340                 345                 350

Asn Ile Pro Asp Ile Met Ala Asn Ser Tyr Lys Ser Thr Tyr Ala Gln
        355                 360                 365

Lys Ala Trp Asp Glu Phe Tyr Ala Asp Gln Ala Lys Ala Asp Lys Lys
```

Tyr Ala Gln Tyr Asn Leu Pro Ala Gln Tyr Ala Leu Leu Ser Asn
385             390             395             400

Lys Asp Thr Val Pro Gln Val Tyr Tyr Gly Asp Leu Tyr Lys Glu Thr
            405             410             415

Asp Gln Tyr Met Lys Thr Lys Ser Met Tyr Tyr Asp Ala Ile Thr Thr
            420             425             430

Leu Met Lys Ala Arg Gly Glu Phe Val Asn Gly Gly Gln Thr Met Thr
            435             440             445

Lys Val Asn Asp Asn Leu Ile Thr Ser Val Arg Tyr Gly Lys Gly Val
            450             455             460

Val Asp Val Ser Ser Asn Gly Thr Asp Pro Leu Ser Arg Thr Thr Gly
465             470             475             480

Met Ala Val Ile Val Gly Asn Asn Pro Ser Met Ser Glu Gln Val Val
            485             490             495

Ala Ile Asn Met Gly Leu Ala His Ala Asn Glu Gln Tyr Arg Asn Leu
            500             505             510

Ile Asp Ser Thr Ala Asp Gly Leu Thr Tyr Asn Ser Asn Gly Ser Val
            515             520             525

Asn Pro Ser Val Leu Thr Thr Asp Ser Lys Gly Ile Leu Arg Val Thr
530             535             540

Val Lys Gly Tyr Ser Asn Pro Tyr Val Ser Gly Tyr Leu Ser Val Trp
545             550             555             560

Val Pro Leu Ile Asn Gly Thr Gln Asn Ala Arg Thr Ser Ala Gln Glu
            565             570             575

Val Arg Asn Val Pro Gly Lys Val Phe Thr Ser Asn Ala Ala Leu Asp
            580             585             590

Ser His Met Ile Tyr Glu Asp Phe Ser Leu Phe Gln Pro Glu Pro Thr
            595             600             605

Thr Val Asn Glu His Ala Tyr Asn Val Ile Lys Asp Asn Val Ala Leu
            610             615             620

Phe Asn Gln Leu Gly Ile Thr Asp Phe Trp Met Ala Pro Ser Tyr Thr
625             630             635             640

Pro Phe Asn Thr Ser Arg Tyr Asn Glu Gly Tyr Ala Met Thr Asp Arg
            645             650             655

Tyr Asn Leu Gly Thr Ala Asp Asn Pro Thr Lys Tyr Gly Asn Gly Glu
            660             665             670

Glu Leu Ser Asn Ala Ile Ala Ala Leu His Gln Ala Gly Leu Lys Val
            675             680             685

Gln Glu Asp Leu Val Met Asn Gln
690             695

<210> SEQ ID NO 67
<211> LENGTH: 1014
<212> TYPE: PRT
<213> ORGANISM: Lactobacillus fermentum

<400> SEQUENCE: 67

Gln Thr His Leu Arg Val Asp Asp Asn Tyr Val Gln Ser Gln Trp Gly
1               5                   10                  15

Asp Trp Tyr Met Phe Gly Lys Asp Gly Arg Ile Ala Thr Gly Leu Tyr
                20                  25                  30

Lys Trp Asp Lys Asn Asn Gln Trp Tyr Tyr Phe Asp Pro Val Thr Tyr
            35                  40                  45

```
Leu Lys Val Thr Asn Lys Trp Val Asp Gly Asn Tyr Asp Glu Asp
 50                  55                  60

Gly Ala Gln Ala Ile Ser Lys Leu Val Thr Ile Asn Asn Arg Leu Tyr
 65                  70                  75                  80

Tyr Phe Asp Asp Gln Gly Lys Glu Ile Ser Asn Gln Phe Arg Thr Ile
                     85                  90                  95

His Gly Asn Thr Tyr Tyr Phe Gly Asn Asp Ser Ala Ala Val Thr Gly
                100                 105                 110

Gln Gln Thr Ile Asp Gly Lys Val Tyr Lys Phe Ser Asn Tyr Gly Tyr
                115                 120                 125

Leu Leu Gly Asn Arg Tyr Gly Lys Ile Glu Asn Gly Lys Leu Asn Ile
130                 135                 140

Tyr Ser Leu Ala Asp Asn Ser Leu Ile Lys Thr Val Glu Ala Gly Pro
145                 150                 155                 160

Trp Glu Asn Met Ala Tyr Ser Met Asp Ser Asn Ser Ile Asn Asn Ile
                165                 170                 175

Asp Gly Tyr Ile Ser Tyr Thr Gly Trp Tyr Arg Pro Tyr Gly Thr Ser
                180                 185                 190

Gln Asp Gly Lys Thr Trp Tyr Pro Thr Thr Val Ala Asp Trp Arg Pro
                195                 200                 205

Ile Leu Met Tyr Val Trp Pro Ser Lys Asp Val Gln Val Lys Phe Ile
210                 215                 220

Gln Tyr Phe Val Asn His Gly Tyr Glu Asn Ser Asn Tyr Gly Leu Thr
225                 230                 235                 240

Ala Gly Ser Val Lys Asp Leu Ser Glu Asn Thr Ala Ser Ile Lys Leu
                245                 250                 255

Asn Glu Val Ala Gln Asn Leu Arg Tyr Val Ile Glu Gln His Ile Val
                260                 265                 270

Ala Ala Lys Ser Thr Ser Gln Leu Ala Asn Asp Ile Asn Asn Phe Ile
                275                 280                 285

Thr Thr Ile Pro Glu Leu Ser Lys Ala Ser Glu Leu Ser Val Val Asn
                290                 295                 300

Arg Tyr Gly Tyr Gln Pro Asp Tyr Ser Gly Ser Val Asp Asp Gln
305                 310                 315                 320

Val Ile Phe Val Asn Asn Asp Ser Lys Asn Gln Lys Ile Gly Asn Thr
                325                 330                 335

Ser Tyr Ala Asp Ser Asn Tyr Arg Leu Met Asn Arg Thr Ile Asn Asn
                340                 345                 350

Gln Asn Gly Asp Asn Ser Asp Asp Ser Pro Glu Leu Leu Val Gly
                355                 360                 365

Asn Asp Ile Asp Asn Ser Asn Pro Val Val Gln Ala Glu Asn Leu Asn
370                 375                 380

Trp Glu Tyr Phe Leu Leu Asn Tyr Gly Lys Phe Met Asn Tyr Asn Pro
385                 390                 395                 400

Asn Gly Asn Phe Asp Gly Phe Arg Ile Asp Ala Ala Asn Ile Asp
                405                 410                 415

Ala Asp Val Leu Asp Gln Ala Ala Gln Leu Ile Asn Ser Ile Tyr Asn
                420                 425                 430

Thr Lys Gly Asn Gln Ala Asn Ala Asn Asp His Leu Ile Tyr Asn Glu
                435                 440                 445

Gly Tyr His Ser Gly Ala Ala Asn Met Leu Asp Arg Lys Ser Asn Pro
450                 455                 460

Glu Leu Tyr Met Asp Ser Gly Tyr Phe Tyr Thr Leu Glu Asn Val Leu
```

-continued

```
              465                 470                 475                 480
        Gly Arg Ala Ser Asp Arg Asp Ile Asn Asn Leu Ile Thr Asn Ser
                          485                 490                 495
        Ile Val Asn Arg Gln Asn Asp Val Ser Glu Asn Val Ala Thr Pro Asn
                          500                 505                 510
        Trp Ser Phe Val Thr Asn His Asp Gln Arg Lys Asn Leu Ile Asn Gln
                          515                 520                 525
        Ile Val Ile Asp Asp His Pro Gly Val Ala Asp Ile Met Ser Asp Gly
                          530                 535                 540
        Tyr Lys Ala Glu Tyr Val Asn Gln Ala Trp Lys Glu Phe Tyr Ala Asp
        545                 550                 555                 560
        Gln Ala Arg Thr Asp Lys Lys Tyr Thr Gln Tyr Asn Leu Pro Ala Gln
                          565                 570                 575
        Tyr Ala Leu Leu Leu Thr Asn Lys Asp Thr Val Pro Gln Val Tyr Tyr
                          580                 585                 590
        Gly Asp Leu Tyr Asp Glu Thr Asp Gln Tyr Met Gln Asn Lys Ser Val
                          595                 600                 605
        Tyr Tyr Asp Ala Ile Thr Thr Leu Met Lys Ala Arg Lys Ser Tyr Val
                          610                 615                 620
        Ser Gly Gly Gln Ser Met Ile Lys Ile Asn Asp His Leu Leu Thr Ser
        625                 630                 635                 640
        Val Arg Tyr Gly Lys Gly Ile Ile Asp Gly Asn Val Ser Met Thr Asp
                          645                 650                 655
        Ile Leu Gly Arg Asn Ser Gly Ile Ala Val Val Gly Asn Asp Ala
                          660                 665                 670
        Gln Met Ala Asn Gln Thr Ile Ser Ile Asn Met Gly Lys Ala His Ala
                          675                 680                 685
        Asn Gln Ala Tyr Lys Gln Leu Leu Gly Thr Ile Asp Ser Gly Leu Thr
                          690                 695                 700
        Ser Ser Asp Thr Thr Ile Tyr His Thr Asp Ser Asn Gly Val Leu Asn
        705                 710                 715                 720
        Val Thr Val Lys Gly Tyr Ser Asn Pro Tyr Val Ser Gly Tyr Leu Gly
                          725                 730                 735
        Val Trp Val Pro Leu Asn Gly Gly Ala Asn Ile Thr Thr Lys Ala Ser
                          740                 745                 750
        Glu Val Thr Asn Gln Ser Asp Lys Thr Tyr Ser Ser Asn Ala Ala Leu
                          755                 760                 765
        Asp Ser His Val Ile Tyr Glu Asp Phe Ser Leu Phe Gln Pro Glu Pro
                          770                 775                 780
        Thr Ser Lys Ala Glu His Ala Tyr Asn Ile Ile Ala Asp Asn Ala Ser
        785                 790                 795                 800
        Leu Phe Asn Glu Leu Gly Ile Thr Asp Phe Trp Met Ala Pro Ala Tyr
                          805                 810                 815
        Thr Pro Phe Asn Arg Ser Arg Tyr Asn Glu Gly Tyr Ser Met Thr Asp
                          820                 825                 830
        Arg Tyr Asn Leu Gly Thr Glu Ala Asn Pro Thr Lys Tyr Gly Ser Gly
                          835                 840                 845
        Glu Glu Leu Ser Asn Ala Ile Ala Ala Leu His Asp Ala Gly Leu Lys
                          850                 855                 860
        Val Gln Glu Asp Leu Val Met Asn Gln Met Ile Gly Phe Ser Gly Gln
        865                 870                 875                 880
        Glu Ala Val Thr Val Thr Arg Thr Asp Ala His Thr Lys Gln Leu Thr
                          885                 890                 895
```

Val Asp Gly Lys Thr Phe Ala Asn Gln Ile Tyr Phe Ala Tyr Thr Arg
            900                 905                 910

Gly Gly Gly Glu Gly Gln Lys Asn Tyr Gly Lys Tyr Leu Asp Glu
        915                 920                 925

Leu Gln Lys Lys Tyr Pro Glu Leu Phe Thr Thr Lys Ala Val Ser Thr
    930                 935                 940

Gly Val Ala Pro Asp Pro Ser Val His Ile Thr Glu Trp Ser Ala Lys
945                 950                 955                 960

Tyr Gln Asn Gly Thr Ser Leu Gln Asn Ile Gly Ile Gly Leu Ala Val
                965                 970                 975

Lys Leu Ala Asn Gly Asp Tyr Ala Tyr Leu Asn Asp Ser Asn Asn Lys
            980                 985                 990

Ala Phe Asn Thr Ala Leu Pro Glu Thr Met Ser Ser Ala Asp Tyr Tyr
        995                 1000                1005

Ala Asn Ile Glu Asp Asp
    1010

<210> SEQ ID NO 68
<211> LENGTH: 689
<212> TYPE: PRT
<213> ORGANISM: Lactobacillus fermentum

<400> SEQUENCE: 68

Trp Tyr Arg Pro Tyr Gly Thr Ser Gln Asp Gly Lys Thr Trp Tyr Pro
1               5                   10                  15

Thr Thr Val Ala Asp Trp Arg Pro Ile Leu Met Tyr Val Trp Pro Ser
            20                  25                  30

Lys Asp Val Gln Val Lys Phe Ile Gln Tyr Phe Val Asn His Gly Tyr
        35                  40                  45

Glu Asn Ser Asn Tyr Gly Leu Thr Ala Gly Ser Val Lys Asp Leu Ser
    50                  55                  60

Glu Asn Thr Ala Ser Ile Lys Leu Asn Glu Val Ala Gln Asn Leu Arg
65                  70                  75                  80

Tyr Val Ile Glu Gln His Ile Val Ala Ala Lys Ser Thr Ser Gln Leu
                85                  90                  95

Ala Asn Asp Ile Asn Asn Phe Ile Thr Thr Ile Pro Glu Leu Ser Lys
            100                 105                 110

Ala Ser Glu Leu Ser Val Val Asn Arg Tyr Gly Tyr Gln Pro Asp Tyr
        115                 120                 125

Ser Gly Ser Val Asp Asp Gln Val Ile Phe Val Asn Asn Asp Ser
    130                 135                 140

Lys Asn Gln Lys Ile Gly Asn Thr Ser Tyr Ala Asp Ser Asn Tyr Arg
145                 150                 155                 160

Leu Met Asn Arg Thr Ile Asn Asn Gln Asn Gly Asp Asn Ser Asp
                165                 170                 175

Asp Ser Pro Glu Leu Leu Val Gly Asn Asp Ile Asp Asn Ser Asn Pro
            180                 185                 190

Val Val Gln Ala Glu Asn Leu Asn Trp Glu Tyr Phe Leu Leu Asn Tyr
        195                 200                 205

Gly Lys Phe Met Asn Tyr Asn Pro Asn Gly Asn Phe Asp Gly Phe Arg
    210                 215                 220

Ile Asp Ala Ala Asp Asn Ile Asp Ala Asp Val Leu Asp Gln Ala Ala
225                 230                 235                 240

Gln Leu Ile Asn Ser Ile Tyr Asn Thr Lys Gly Asn Gln Ala Asn Ala
                245                 250                 255

```
            Asn Asp His Leu Ile Tyr Asn Glu Gly Tyr His Ser Gly Ala Ala Asn
                        260                 265                 270

Met Leu Asp Arg Lys Ser Asn Pro Glu Leu Tyr Met Asp Ser Gly Tyr
                        275                 280                 285

Phe Tyr Thr Leu Glu Asn Val Leu Gly Arg Ala Ser Asp Arg Asp Asp
                        290                 295                 300

Ile Asn Asn Leu Ile Thr Asn Ser Ile Val Asn Arg Gln Asn Asp Val
            305                 310                 315                 320

Ser Glu Asn Val Ala Thr Pro Asn Trp Ser Phe Val Thr Asn His Asp
                        325                 330                 335

Gln Arg Lys Asn Leu Ile Asn Gln Ile Val Ile Asp Asp His Pro Gly
                        340                 345                 350

Val Ala Asp Ile Met Ser Asp Gly Tyr Lys Ala Glu Tyr Val Asn Gln
                        355                 360                 365

Ala Trp Lys Glu Phe Tyr Ala Asp Gln Ala Arg Thr Asp Lys Lys Tyr
                        370                 375                 380

Thr Gln Tyr Asn Leu Pro Ala Gln Tyr Ala Leu Leu Thr Asn Lys
            385                 390                 395                 400

Asp Thr Val Pro Gln Val Tyr Tyr Gly Asp Leu Tyr Asp Glu Thr Asp
                        405                 410                 415

Gln Tyr Met Gln Asn Lys Ser Val Tyr Tyr Asp Ala Ile Thr Thr Leu
                        420                 425                 430

Met Lys Ala Arg Lys Ser Tyr Val Ser Gly Gln Ser Met Ile Lys
                        435                 440                 445

Ile Asn Asp His Leu Leu Thr Ser Val Arg Tyr Gly Lys Gly Ile Ile
            450                 455                 460

Asp Gly Asn Val Ser Met Thr Asp Ile Leu Gly Arg Asn Ser Gly Ile
            465                 470                 475                 480

Ala Val Val Val Gly Asn Asp Ala Gln Met Ala Asn Gln Thr Ile Ser
                        485                 490                 495

Ile Asn Met Gly Lys Ala His Ala Asn Gln Ala Tyr Lys Gln Leu Leu
                        500                 505                 510

Gly Thr Ile Asp Ser Gly Leu Thr Ser Ser Asp Thr Thr Ile Tyr His
                        515                 520                 525

Thr Asp Ser Asn Gly Val Leu Asn Val Thr Val Lys Gly Tyr Ser Asn
            530                 535                 540

Pro Tyr Val Ser Gly Tyr Leu Gly Val Trp Val Pro Leu Asn Gly Gly
            545                 550                 555                 560

Ala Asn Ile Thr Thr Lys Ala Ser Glu Val Thr Asn Gln Ser Asp Lys
                        565                 570                 575

Thr Tyr Ser Ser Asn Ala Ala Leu Asp Ser His Val Ile Tyr Glu Asp
                        580                 585                 590

Phe Ser Leu Phe Gln Pro Glu Pro Thr Ser Lys Ala Glu His Ala Tyr
                        595                 600                 605

Asn Ile Ile Ala Asp Asn Ala Ser Leu Phe Asn Glu Leu Gly Ile Thr
                        610                 615                 620

Asp Phe Trp Met Ala Pro Ala Tyr Thr Pro Phe Asn Arg Ser Arg Tyr
            625                 630                 635                 640

Asn Glu Gly Tyr Ser Met Thr Asp Arg Tyr Asn Leu Gly Thr Glu Ala
                        645                 650                 655

Asn Pro Thr Lys Tyr Gly Ser Gly Glu Glu Leu Ser Asn Ala Ile Ala
                        660                 665                 670
```

```
Ala Leu His Asp Ala Gly Leu Lys Val Gln Glu Asp Leu Val Met Asn
        675                 680                 685
Gln
```

GLUCOOLIGOSACCHARIDES COMPRISING (ALPHA 1->4) AND (ALPHA 1->6) GLYCOSIDIC BONDS, USE THEREOF, AND METHODS FOR PROVIDING THEM

This application is the U.S. National Phase of, and Applicants claim priority from, International Patent Application Number PCT/NL2010/050269 filed May 10, 2010, European Patent Application bearing serial No. EP 09159825.0 filed May 8, 2009 and U.S. Provisional Patent Application bearing Ser. No. U.S. 61/181,315 filed May 27, 2009, which are incorporated herein by reference in their entirety.

INCORPORATION OF SEQUENCE LISTING

Incorporated herein by reference in its entirety is the Sequence Listing for the above-identified Application. The Sequence Listing is disclosed on a computer-readable ASCII text file titled "Sequence Listing 294_404PCTUS.txt", modified on Mar. 29, 2016. The sequence.txt file is 108 KB.

BACKGROUND OF THE INVENTION

The invention relates to the field of poly- and oligosaccharides and their nutritional effects. In particular, it relates to the application of α-glucanotransferases in methods for preparing dietary fibers, including prebiotic oligosaccharides, and to novel oligosaccharides obtainable thereby.

The term 'dietary fibre' was first used in 1953 by Hipsley to describe the plant cell wall components of food. Today there are many definitions of fibre in use, but as yet there is no universally accepted definition. Generally, fibres are derived from carbohydrate sources that have a non-digestible component. Fibres are typically divided into two categories; the insoluble fibres such as wheat bran, resistant starch, hemicelluloses, lignin etc., and the soluble fibres, which can be further classified into two subdivisions: short chain length soluble fibres, including polydextrose, inulin and oligosaccharides, and long chain length soluble fibres including pectins, gums (guar, locust bean, carrageenan, xanthan) and β-glucan (from oat or barley for example).

Prebiotics are dietary fibres, as they are not digested by human enzymes but fermented by the flora of the large intestine. Thus they increase biomass and frequency of defecation, thus having a positive effect on constipation and on the health of the mucosa of the large intestine. Prebiotic carbohydrates are naturally occurring and can be found in numerous foods, including asparagus, chicory, tomatoes and wheat, as well as being a natural component of breast milk.

The term prebiotic was first defined by Gibson and Roberfroid in 1995. However, the initial definition proved difficult to verify and since then the authors have further developed the concept proposing a new definition: "A prebiotic is a selectively fermented ingredient that allows specific changes both in the composition and/or activity in the gastrointestinal microflora that confers benefit upon host well-being and health" (Nutr Res Rev 2004; 17: 259-275). In order to qualify for prebiotic classification, an ingredient is therefore required to (i) resist digestion (gastric acidity, hydrolysis by mammalian enzymes and gastrointestinal absorption); (ii) be fermented by the gastrointestinal microbiota; and (iii) selectively stimulate the growth and/or activity of intestinal bacteria associated with health and well-being. The latter criterion is the main distinguishing feature between a dietary fibre and a prebiotic. Prebiotics are generally recognised for their ability to alter the colonic microbiota, promoting a healthier composition and/or activity by increasing the prevalence of saccharolytic (carbohydrate fermenting) micro-organisms while reducing putrefactive (protein fermenting) micro-organisms.

Established non-digestible carbohydrates that fulfil the prebiotic criteria include fructo-oligosaccharides (FOS), galacto-oligosaccharides (GOS), lactulose, inulin and polydextrose.

Polydextrose is a polysaccharide composed of randomly cross-linked glucose units with all types of glycosidic bonding. Litesse polydextrose is resistant to digestion due to its unique arrangement of glycosidic linkages. Molecularly, (α1→6) bonds predominate, but about 13% of the polymer has (α1→4) linkages, which can be hydrolyzed by enzymes in the human small intestine. It is fermented throughout the colon and is particularly efficient at mediating a prebiotic effect in the distal colon. Human intervention studies have demonstrated that Litesse polydextrose enhances both bifidobacteria and lactobacilli in a dose dependent manner.

Starch is a polysaccharide found commonly in green plants—those containing chlorophyll—as a means of storing energy. Starch forms an integral part of the multi-billion food ingredients market and is characterised by its complex and consolidated nature. Starch is an ideal example of an essential commodity with a wide array of industrial applications, which include paper and card-board making, fermentation, biofuels, biodegradable plastics and detergents, bio-pesticides, surfactants, polyurethane, resins, binders and solvents. However, it is the food industry that provides the largest market for starch and its derivatives.

Starch is either degraded completely in the small intestine to glucose and taken up in the blood or those parts that escape digestion end up in the large intestine where they serve as a general substrate for the colonic microbial flora. Starch and its derivatives in itself do not stimulate specific beneficial colon microbes. Thus, starch in itself is not a prebiotic compound. The partial solution to the problem is to degrade starch into the disaccharide maltose and then use a transglucosidase enzyme to convert the maltose into (α1→6)-linked isomalto-oligosaccharides (IMO) with a degree of polymerization of 2 to 4. These IMO products are, however, too short and are mostly degraded in the small intestine, thus not reaching the colon. That part of the IMO product that reaches the colon is quickly degraded in the proximal part of the colon by the intestinal microflora and does not reach the distal part were more malign, protein degrading bacteria reside. To outcompete these malign bacteria by stimulating beneficial bacterial species, in particular bifidobacteria, longer isomalto-oligosaccharides are required.

Previously, various methods have been developed for chemical modification of malto-oligosaccharides (MOS) and starch (amylose, amylopectin). More recently, also various transglycosylase enzymes (cyclodextrin glucanotransferase, amylomaltase, starch branching enzyme) have been used for modification of starch (amylose, amylopectin).

DESCRIPTION OF THE INVENTION

The present invention provides further means and methods for the (enzymatic) modification of starch, starch derivatives and/or MOS of different chain length in order to change their functional properties and enhance their nutritional value.

It was surprisingly found that these aims can be met by the use of an α-glucanotransferase of the GTFB type of glucansucrases, member of glycoside hydrolase family GH70 whereas glucansucrase enzymes catalyze conversion of sucrose into α-glucan poly- and oligosaccharides, it was previously reported that GTFB is not reactive with sucrose at all (Kralj 2004). It is disclosed herein that GTFB displays a high activity towards gluco-oligosaccharides comprising (α1→4) linked glucose residues, such as malto-oligosaccharides (MOS). GTFB catalyzes a disproportionating type of reaction, shortening one substrate molecule and elongating a second substrate molecule. Both products can be substrates again in the next reaction. GTFB activity can thus yield a series of linear gluco-oligosaccharides up to at least DP35. Structural analysis of the products has revealed that GTFB cleaves (α1→4) glucosidic bonds and makes new (α1→4) and (α1→6) bonds. It is the first example of an enzyme with this reaction and product specificity. Accordingly, this enzyme is designated as (1→4)-α-D-glucan: (1→4) (1→6)-α-D-glucan α-D-glucanotransferase or, alternatively, as α-glucanotransferase. Glucansucrase enzymes also use MOS but only as acceptor substrates in the presence of sucrose as donor substrate, This results in synthesis of a range of oligosaccharides, e.g. a maltose extended with a series of glucose units bound via (α1→6) linkages in case of dextransucrase. In case of glucansucrases, however, the (α1→4) linkages in MOS substrates are not cleaved and MOS are only used as acceptor substrate. This is a major difference with the GFTB enzyme that fails to act on sucrose and instead uses MOS as donor and acceptor substrates, cleaving the (α1→4) linkages, and introducing via a disproportionation type of reaction new (α1→6) and (α1→4) linkages. The products that GTFB can synthesize from starch or starch derivatives contain relatively long isomalto-oligosaccharide (IMO) side chains, in particular IMO side chains with a degree of polymerization of 4 and higher. Part of the IMO-maltodextrin (IMO-MALT) is degraded in the small intestine, being less than what would have been degraded when unmodified starch/derivatives would have been consumed. This is because those parts of the maltodextrin that are close to the IMO part will not be degraded by the intestinal amylases, since amylases need a certain length of linear (α1→4) linked glucose residues to act on. IMO-MALT can therefore be considered as a partially resistant starch derivative giving less glucose production in the small intestine than unmodified maltodextrin would give. This is considered beneficial and contributes to a healthy life style (reduce the risk of developing obesity, type II diabetes, and heart and coronary diseases related to the overconsumption of quickly degradable starch/derivatives). The IMO-MALT part that passes unmodified into the colon will be further degraded by the residual microflora. The IMO part of the IMO-MALT containing (α1→6) linkages can act as a specific substrate for beneficial bifidobacteria, making IMO-MALT a prebiotic ingredient. IMO-MALT therefore has at least the following benefits:

1. partially resistant maltodextrin/starch, giving less glucose production and thereby contributing to prevention of obesity and type II diabetes 2. prebiotic effect stimulating beneficial gut bifidobacteria and thereby promote gut health In a first embodiment, the invention relates to a method for producing a mixture of gluco-oligosaccharides having one or more (α1→6) glucosidic linkages and one or more (α1→4) glucosidic linkages, comprising contacting a poly- and/or oligosaccharide substrate comprising at its non-reducing end at least two (α1→4)-linked D-glucose units with an α-glucanotransferase enzyme capable of cleaving (α1→4) glucosidic linkages and making new (α1→4) and (α1→6) glucosidic linkages. Alternatively, or in addition, the α-glucanotransferase is capable of transferring a maltosyl-, a maltotriosyl- or a maltotetraosyl-unit to the substrate via a new (α1→6) glucosidic linkage.

It is advantageous, especially for application as dietary fibre, that the gluco-oligosaccharide product(s) are linear or contain linear stretches/moieties of primarily (α1→4) and (α1→6) glucosidic linkages, rendering them resistant to enzymatic attack in the small intestine. Accordingly, the α-glucanotransferase preferably does not introduce (α1→6) branching points, (α1→2) nor (α1→3) linkages.

In a specific aspect, the α-glucanotransferase (GTFB) is a new member of the GH70family of glucansucrases, or a functional homolog thereof having the specified enzymatic activity and substrate preference as described above, For example, the enzyme is selected from those shown in Table 2 or from the group consisting of GTFB from *Lactobacillus reuteri* 121, GTF106B from *Lactobacillus reuteri* TMW 1.106, GTML4 from *Lactobacillus reuteri* ML1 and GTFDSM from *Lactobacillus reuteri* DSM 20016A, GTF from *Lactobacillus fermentum* ATCC 14931, all of the art both at the protein and nucleic acid level. See in particular FIG. 2 and Table 2 herein below for accession numbers. Of course, natural or artificial homologs (mutant) of these known sequences can also be used, including genetically engineered variants displaying desirable properties with respect to thermal stability, substrate specificity, enzymatic activity and the like. In one embodiment, a GTFB homolog is used that shows at least 55%, preferably at least 60%, 75%, like at least 80%, 85%, or at least 90%, sequence identity at the amino acid level with GTFB from the GTFB (-like) enzymes listed in Table 2, or, preferably, with *Lactobacillus reuteri* 121 (AAU08014), GTF106B from *Lactobacillus reuteri* TMW 1.106 (ABP88725), GTML4 from *Lactobacillus reuteri* ML1 (AAU08003), GTFDSM from *Lactobacillus reuteri* DSM 20016A (ABQ83597) or GTF from *Lactobacillus fermentum* ATCC 14931 (ZP_03945763). For example, a GTFB homolog is used that shows at least 55%, preferably at least 60%, 75%, like at least 80%, 85%, or at least 90%, sequence identity at the amino acid level with GTFB from *Lactobacillus reuteri* 121.

It is preferred that the enzyme shows at least 45%, more preferably at least 50%, sequence identity or at least 60% sequence identity at the amino acid level with the catalytic core of GTFB, the catalytic core being represented by the contiguous amino acid sequence $W^{790}YRP \ldots IVMNQ^{1484}$ as found in the protein sequence of GFTB of *L. reuteri* 121: GenBank accession number AAU08014 (protein code).

The GTFB homolog preferably comprises one or more of the following conserved amino acid residues, wherein the numbering corresponds to the position in GTFB of *Lactobacillus reuteri* 121: Arg1013; Asp1015; Ala1017; Asn1019; Glu1053, Gly1054, Tyr1055, His1124, Asp1125, Gln1126, Arg1127, Lys1128, Asp1479; Ile1480, Met1482, Asn1483, Gln1484. Preferably, at least the catalytic residues Asp1015, Glu1053 and Asp1125 are present. More preferably, all of these residues are present.

Four conserved regions have been identified in the catalytic domain of GTF enzymes. Previous protein engineering studies have demonstrated that amino acid residues located in conserved sequence region III and IV (see FIG. 1 for a sequence alignment) control the product specificity of GTF enzymes regarding the glycosidic bond type formed (Hellmuth et al. Biochemistry (2008); Kralj et al. (2005) Biochemistry 44, 9206-9216; Kralj et al. (2006) FEBS J. 273, 3735-3742). Also region I and region II contain amino acid residues that contribute to enzyme activity and reaction specificity [Kralj et al. (2005); Swistowska et al. (2007) FEBS Lett. 581, 4036-4042.]. In a specific aspect, the enzyme comprises at least one of the following consensus sequences wherein the numbering corresponds to the amino acid position in GTFB (see FIG. 1):

A) (conserved region II): $F^{1009}$DGFRVDAADNIDADVLDQA$^{1027}$ (SEQ ID NO. 1)
B) (conserved region III): $H^{1048}$L(S/V)YNEGYHSGAA$^{1060}$ (SEQ ID NO. 12/13)
C) (conserved region IV): $W^{1118}$SFVTNHDQRKN(L/V)I$^{1131}$ (SEQ ID NO. 14/15)
D) (conserved region I): $G^{1473}$LKVQED(I/L)VMNQ$^{1484}$ (SEQ ID NO. 16/17)

In one embodiment, the enzyme is a GTFA member from the glucansucrase group, for instance GTFA from *Lactobacillus reuteri* 121 (GenBank accession number AX306822 or AY697435 (GTF sequence+flanking sequences a.o. GTFB+ transposases), that has been genetically engineered to obtain the unique "GTFB-like" substrate specificity and activity required for practicing a method of the present invention. The invention thus also relates to a genetically modified enzyme belonging to the gtfA type of glucansucrase enzymes comprising at least one of the mutations of Table 1, said enzyme being capable of cleaving ($\alpha$1→4)glucosidic linkages and making new ($\alpha$1→4) and ($\alpha$1→6) glucosidic linkages and having a substrate preference for poly- and/or oligosaccharide substrates comprising ($\alpha$1→4)-linked D-glucose units, in particular malto-oligosaccharides. The skilled person will understand that mutations equivalent to those mentioned in Table 1 can be introduced in GTFA enzyme homologues from other organisms. For example, GTF180 from *Lactobacillus reuteri* 180, GTFML1 from *Lactobacillus reuteri* ML1, DSRS from *Leuconostoc mesenteroides* B512-F, GTFD from *Streptococcus mutans* GS-5 (also see van Hijum et al. 2006). Preferably, multiple mutations selected from Table 1 are introduced. In a specific embodiment, all positions shown in Table 1 are altered.

TABLE 1

Mutations for introducing GTFB-like (a-glucanotransferase) activity in a GTFA-like (glucansucrase) enzyme

| Position# | Mutation* |
|---|---|
| 981 | L → V |
| 1026 | P → A |
| 1062 | D → G |
| 1063 | W → Y |
| 1064 | N → H |
| 1062-1064 | DWN → GYH |
| 1134 | N → Q |
| 1135 | N → R |
| 1136 | delete S |
| 1134-1136 | NNS → QR |
| 1137 | Q → K |
| 1414 | N → L |
| 1463 | D → R, T or M |
| 1510 | W → I or L |
| 1512 | P → M |
| 1513 | D → N | numbering corresponding to *Lactobacillus reuteri* 121 GTFA
*single-letter amino acid code Also provided is the use of an enzyme capable of cleaving ($\alpha$1→4) glucosidic linkages and making new ($\alpha$1→4) and ($\alpha$1→6) glucosidic linkages, and/or transferring a maltosyl-, a maltotriosyl- or a maltotetraosyl-unit making a new ($\alpha$1→6) glucosidic linkage, in a method for producing starch derivatives, preferably (partially) indigestible starch derivatives. In one embodiment, the enzyme is a GTFB type of glucansucrase, for example selected from Table 2 or from the group consisting of GTFB from *Lactobacillus reuteri* 121, GTF106B from *Lactobacillus reuteri* TMW 1.106, GTML4 from *Lactobacillus reuteri* ML1, GTFDSM from *Lactobacillus reuteri* DSM 20016$^4$ or GTF from *Lactobacillus fermentum* ATCC 14931, or a natural or artificial homolog (mutant) thereof. Preferably, the enzyme is GTFB from *Lactobacillus reuteri* 121.

The person skilled in the art will be able to determine suitable process conditions for performing a method as provided herein by routine experimentation, such as temperature, incubation time, pH, amount of enzyme, etc. A pH range of 4-5, preferably 4-4.5, can be used. In one embodiment, a temperature of at least 30° C., preferably 37° C. is used. In another embodiment, for instance in view of substrate properties and/or sterility, it may be desirable to work at a more elevated temperature, like at least 70° C., provided that the enzyme is sufficiently heat stable. The dry matter content of the reaction mixture can vary. In one embodiment, it is at least 10%, preferably at least 25%.

Various oligosaccharide or glucan substrates or substrate mixtures can be used in a method according to the invention, provided that they comprises poly- and/or oligosaccharides whose non-reducing end contains ($\alpha$1→4) linked glucose residues. Preferably, said non-reducing end contains 3 or more consecutive ($\alpha$1→4)-linked glucose residues. Linear substrates are preferred. Accordingly, also provided is a method for producing a mixture of linear gluco-oligosaccharides having one or more ($\alpha$1→6) glucosidic linkages and one or more ($\alpha$1→4) glucosidic linkages, comprising contacting, e.g. by incubating, a linear poly- and/or oligosaccharide substrate comprising at its non-reducing end at least two ($\alpha$1→4)-linked D-glucose units with an $\alpha$-glucanotransferase enzyme capable of cleaving ($\alpha$1→4) glucosidic linkages and making new ($\alpha$1→4) and ($\alpha$1→6) glucosidic linkages.

Very good results are observed when the substrate has a degree of polymerization of at least 4, preferably at least 5, more preferably at least 6. The substrate is for instance selected from the group consisting of native starch, modified starch, starch-derivatives, malto-oligosaccharides, amylose, amylopectin, maltodextrins, ($\alpha$1→4) glucans, reuteran, or combinations thereof. The term "starch derivative" as used herein refers to the product of native starch that has undergone one or more modifications, be it by physical and/or (bio)chemical means. Modifications include depolymerization, cross linking and substitution. The starch or starch derivative can originate from various plant sources, including potato, maize, tapioca or wheat. Some of the other raw materials include; rice, cassava, arrowroot, mung bean, peas, barley, oats, buckwheat, banana, sorghum and lentils. Starch (derivative) from potato, maize, tapioca or wheat is preferred.

In a specific aspect, a method of the invention uses amylomaltase (AMase)-treated starch (ATS), preferably potato starch, as substrate. ATS is commercially available from AVEBE (Veendam The Netherlands) under the trade name Etenia™. A further specific embodiment employs reuteran as substrate, which is an $\alpha$-glucan product of reuteransucrase activity and comprises ($\alpha$1→4) and ($\alpha$1→6) linkages. Also a mixture of reuteran and malto-oligosaccharides (MOS) yields very good results. Also provided is the treatment of a product obtainable by the incubation of starch, a starch derivative, maltodextrin or maltooligosaccharide with GTFB or GTFB-related enzyme with a hydrolytic enzyme that degrades alpha, 1-4-O-glycosidic linkages such as alpha-amylase, beta-amylase, alpha-glucosidase, or maltogenic amylase. This provides a slow or non-digestible oligosaccharide/fiber.

As is exemplified herein below, a method of the invention as described above will typically yield a mixture of various linear gluco-oligosaccharides having one or more consecutive (α1→6) glucosidic linkages and one or more, preferably two or more, consecutive (α1→4) glucosidic linkages. For many industrial (e.g. nutritional) applications, the mixture can essentially be used as such and does not require further purification. However, if desired it is of course possible to isolate or remove one or more individual gluco-oligosaccharides from the mixture. To that end, various methods known in the art can be used, for example precipitation-fractionation or chromatography techniques. In one embodiment, a method of the invention comprises subjecting the mixture to size exclusion and/or anion exchange chromatography and isolating at least one gluco-oligosaccharide having one or more (α1→6) glucosidic linkages and one or more, preferably two or more, (α1→4) glucosidic linkages.

As said, an enzyme activity as disclosed herein can give rise to an oligosaccharide with a unique structure. Provided is a linear (i.e. non-branched) gluco-oligosaccharide of the general formula A-B, a glucan comprising such linear moiety or a mixture comprising different gluco-oligosaccharides/moieties of the general formula A-B, wherein the linkage between the moiety A and the moiety B is an (α1→6) glucosidic linkage and wherein B comprises at least two, preferably at least three, consecutive (α1→4) linked glucose residues. Preferably, only (α1→6) and (α1→4) glucosidic linkages are present. The linear moiety of the general formula A-B can be attached to any type of glucan (be it branched or unbranched), for example waxy amylopectin.

In one embodiment, the linear (i.e. unbranched) gluco-oligosaccharide of the general formula A-B, or the mixture comprising different gluco-oligosaccharides of the general formula A-B, characterized in that (i) the linkage between the moiety A and the moiety B is an (α1→6) glucosidic linkage, (ii) moiety A comprises two or more consecutive (α1→6) glucosidic linkages, preferably wherein A comprises an isomalto-oligosaccharide with a degree of polymerization of at least 4 glucose residues and (iii) B comprises at least two, preferably at least three, consecutive (α1→4) linked glucose residues. For example, the A moiety consists of a series of consecutive (α1→6) linked glucose residues and the B moiety consists of a series of consecutive (α1→4) linked glucose residues.

In another embodiment, the A moiety comprises one or more consecutive (α1→4) glucosidic linkages, preferably wherein A comprises a malto-oligosaccharide with at least four (α1→4) linked glucose residues. Thus, a stretch of (α1→4) linked residues can be linked via an (α1→6) linkage to another stretch of (α1→4) linked residues.

Oligosaccharides of varying chain lengths are provided. In one embodiment, the gluco-oligosaccharide (moiety) has a degree of polymerization (DP) of at least 7 (DP≥7), preferably at least 10 (DP≥10), more preferably at least 15, up to about 50.

Oligosaccharides with a length up to more than 30 residues have been observed according to MALDI-TOF-MS analysis. Typically, the relative amount of the high molecular mass products DP10-DP35 in a mixture is less than the amount of products DP<10. An exemplary mixture has an average degree of polymerization of at least 5, preferably at least 6, such as between 6 and 15.

When using malto-oligosaccharides (e.g. DP7, or DP6) as substrates, a series of linear gluco-oligosaccharides are produced, and often different structures of a given DP are observed. For instance, at least 4 DP8 structures were identified, each differing with respect to the number of (α1→6) and (α1→4) glucosidic linkages. See also FIG. 6. Generally speaking, the ratio (α1→6) to (α1→4) glucosidic linkages and the structural diversity increases with increasing chain length.

In one aspect, at least 20%, preferably at least 25%, of the linkages is (α1→6). The ratio between (α1→6) and (α1→4) glucosidic linkages generally ranges between 20:80 and 90:10. For example, provided is a linear DP7 product with two consecutive (α1→6) linkages and four consecutive (α1→4) linkages; linear DP8 product with two consecutive (α1→6) linkages and five consecutive (α1→4) linkages; or a DP8 with three consecutive (α1→6) linkages and four consecutive (α1→4) linkages; a DP9 with five consecutive (α1→6) linkages and three consecutive (α1→4) linkages; a DP9 with four consecutive (α1→6) linkages and four consecutive (α1→4) linkages; a DP10 with five consecutive (α1→6) linkages and four consecutive (α1→4) linkages (see FIG. 6)

For application as nutritional ingredient that provides the consumer with a prebiotic fiber as well as a source of energy, the oligosaccharide (mixture) preferably comprises substantial amounts of both (α1→6) and (α1→4) glucosidic linkages. Therefore, in one embodiment the ratio between (α1→6) and (α1→4) glucosidic linkages is between 30:70 and 70:30.

A gluco-oligosaccharide or gluco-oligosaccharide mixture according to the invention has important industrial applications, in particular in nutritional and dietary compositions. Provided is a (human or animal) food product comprising a gluco-oligosaccharide or gluco-oligosaccharide (mixture) according to the invention. The food product can be a solid, semi-solid or liquid food product. The food product can be a conventional nutritional product or a dietetic product. It can be a ready-to-eat food item or a food product that requires further handling prior to consumption, like a bake-off bread product. Exemplary products include a dairy product, baby or infant formula, bakery product, pasta product, noodle product, confectionery product, liquid drink, sport drink, beverage and ice cream.

A further embodiment relates to the use of a gluco-oligosaccharide or gluco-oligosaccharide mixture according to the invention as food additive, for example as prebiotic fiber. Prebiotics can be used in multiple food applications from dairy through to bakery, confectionery and beverage applications. Due to their chemical and physical structure they tend to be highly soluble and have the ability to improve body, texture and mouth feel.

Another useful application relates to inhibiting enzymes of the alpha-amylase type, such as salivary and pancreatic amylases. These enzymes normally act on a (α1→4) malto-oligosaccharide chain with DP ranging from 4-6. It is hypothesized that the presence of (non-hydrolyzable) (α1→6) linkages in an oligosaccharide of the invention only results in enzyme binding but not in glucose release. Addition of such oligosaccharides would lower the rate of metabolism of (e.g. starch metabolism), thereby reducing the glycaemic index (GI) of a food product. A gluco-oligosaccharide (mixture) according to the invention can therefore also help to reduce caloric value and/or the glycaemic load of food products. It thus contributes to a low GI diet. This is of particular interest for human health in general as well as in specific metabolic diseases, including diabetes mellitus and obesity.

In a further embodiment, the gluco-oligosaccharide (mixture) finds its use in a therapeutical or cosmetic application, in particular for controlling a normal skin flora and promoting a healthy skin. The oligosaccharide can bring about a probiotic effect in that it can preferably be utilized selectively by saprophytic bacteria. For example, the oligosaccharide can promote the growth of beneficial skin bacteria (e.g. *Micrococcus kristinae*) compared to the growth of less desirable bacteria such as *Staphylococcus aureus* and *Corynebacterium xerosis*. Provided is a cosmetic composition comprising a gluco-oligosaccharide or gluco-oligosaccharide mixture according to the invention and a suitable carrier. It is also possible to employ the gluco-oligosaccharide (mixture) in a personal care item, for instance to include an absorbent article such as a disposal diaper, sanitary napkin, or the like which can reduce odor and dermatitis (rash) generated when such an absorbent article is worn.

LEGENDS TO THE FIGURES

FIG. 1. Amino acid sequence alignment of conserved regions (II, III, IV and I) in the catalytic domains of (A) (putative) α-glucanotransferase enzymes, (B) DSRE and DSRP, glucansucrase enzymes containing two catalytic domains (CD1 and CD2) and (C) dextran-, mutan-, alternan- and reuteransucrase enzymes of lactic acid bacteria. The seven strictly conserved amino acid residues (1-7), having important contributions to the −1 and +1 subsites glucansucrase enzymes are also conserved in the α-glucanotransferase enzymes (shown underlined GTFA and GTFB of *L. reuteri* 121). Amino acid numbering (italics) is according to GTF180 of *L. reuteti* 180. GTFB amino acid D1015 (putative nucleophilic residue) is shown in bold type.

FIG. 2. Phylogenentic tree of GTFB-like proteins derived from ahylogenetic analysis of all 108 glycoside hydrolase family 70 protein sequences available in the Pfam database. See table 2 above for more details on the sequences in this cluster.

Figure 3:
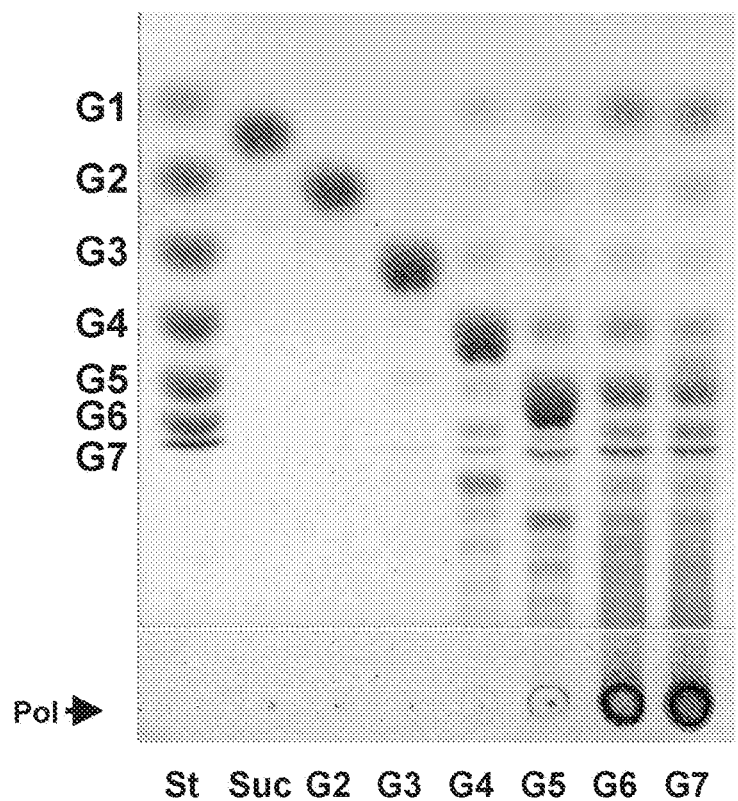

FIG. 3. TLC analysis of the reaction products of 90 nM GTFB incubated for 13 h in 50 mM NaAc buffer pH 4.7, 1 mM $CaCl_2$ with 25 mM sucrose or 25 mM malto-oligosaccharides. St=standard, Suc, sucrose; G1, glucose; G2, maltose; G3, maltotriose; G4, maltotetraose; G5, maltopentaose; G6, maltohexaose; G7, maltoheptaose; Pol, polymer FIG. 4. Dionex analysis of the reaction products of 90 nM GTFB incubated for either 0, 1, 2 or 8 h in 50 mM NaAc buffer pH 4.7, 1 mM $CaCl_2$ with A) 25 mM maltohexaose or B) 25 mM maltoheptaose.

Figure 5:
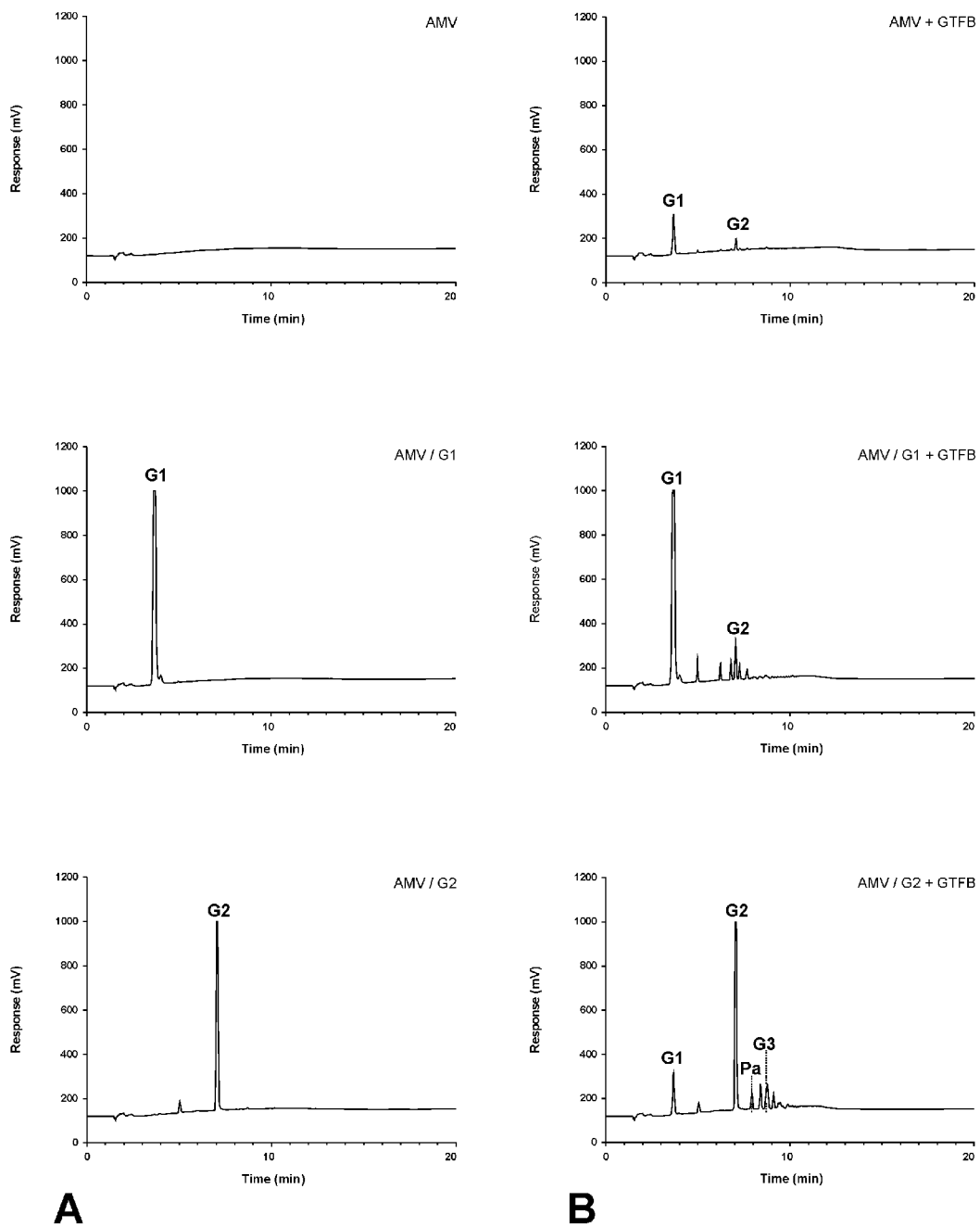

FIG. 5. Dionex analysis of incubated substrate samples without enzyme (panels A) or with 90 nM GTFB (panels B) incubated overnight at 37° C. in 25 mM NaAc pH 4.7, 1 mM $CaCl_2$ with 0.25% amylose-V (abbreviated to AMV) alone as donor substrate and amylose-V with 25 mM glucose (G1) or 25 mM maltose (G2) as acceptor substrates.

Figure 6:
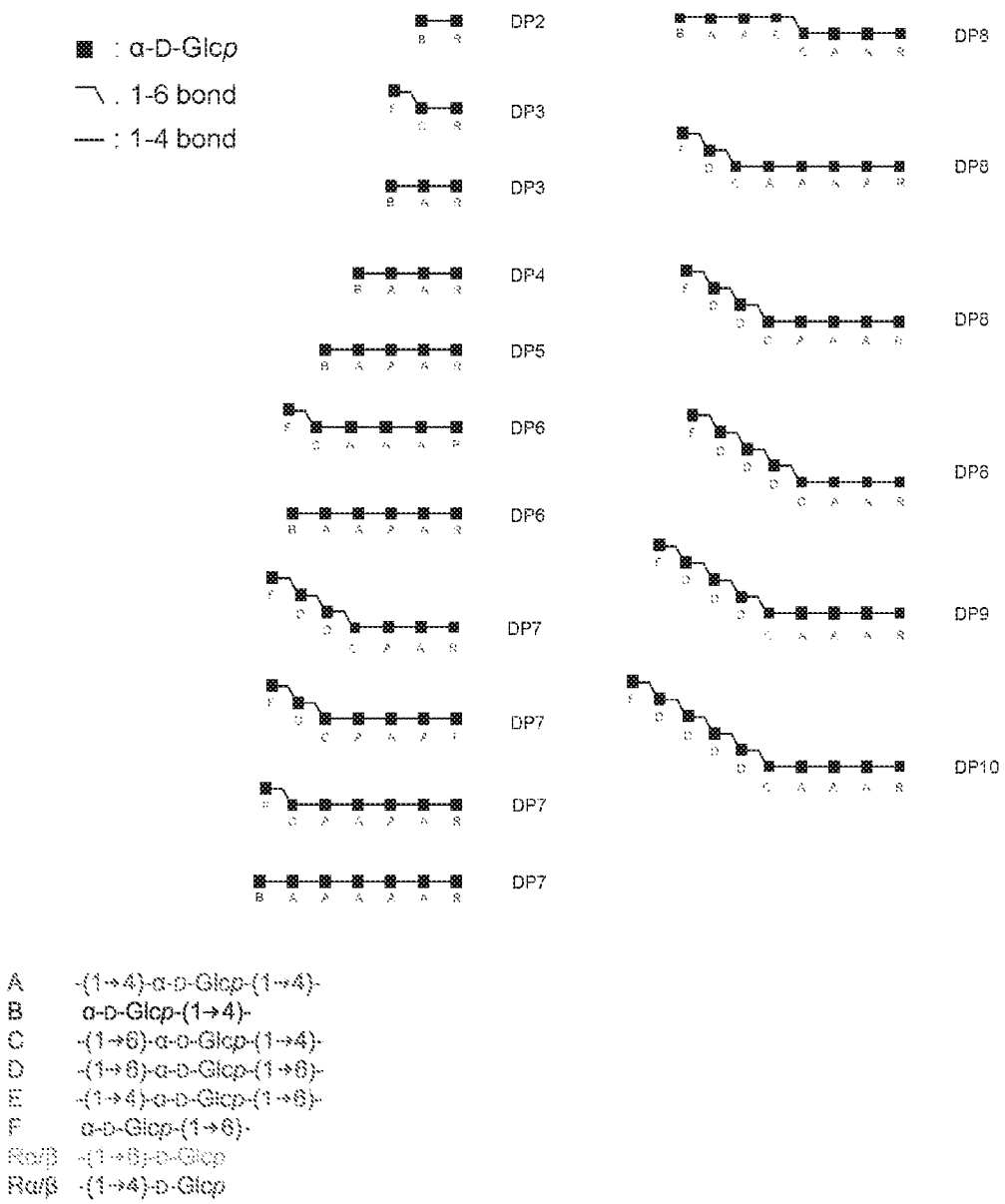

FIG. 6. Schematic representation of the various α-glucans in the product mixture of the incubation of malto-oligosaccharide DP7 with GTFB(-like) activity.

Figure 7:
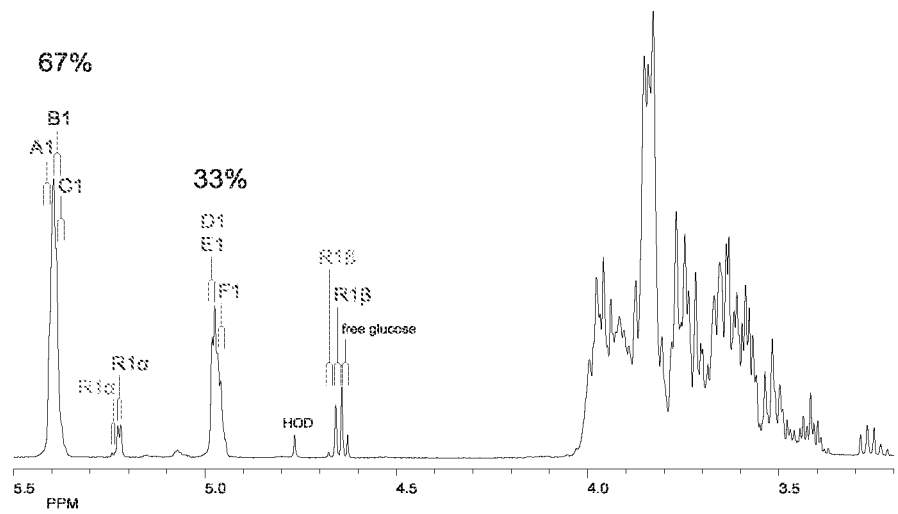

FIG. 7. $^1$H NMR spectrum of the product mixture following incubation of malto-oligosaccharide DP7 (100 mM) with GTFB (250 mM) for 120 h.

Figure 8:
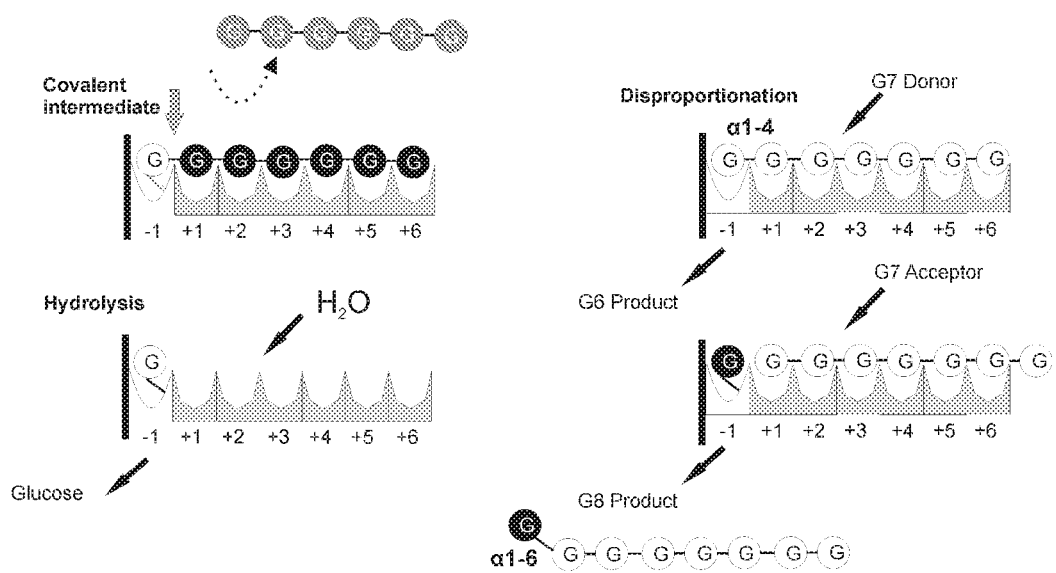

FIG. 8. Possible mode of action of GTFB. Schematic representation of the reaction sequences occurring in the active site of GTFB type of enzymes. The donor and (acceptor) subsites of GTFB type of enzymes are mapped out based on the available 3D structural information of glucansucrase enzymes (with one donor (−1) sub site) and data obtained in the present study. Binding of G7 to subsites −1 and +1 to +6 results in cleavage of the α-1,4 glycosidic bond (G6 released, shown in grey), and formation of a (putative) covalent intermediate at subsite −1 (indicated with a grey line). Depending on the acceptor substrate used, hydrolysis (with water) or glycosyltransfer with an oligosaccharide acceptor (see below). The *Lb. reuteri* 121 GTFB enzyme also catalyzes a disproportionation reaction with maltooligosaccharides. Two molecules of maltoheptaose (G7) for instance are converted into one G6 molecule and into a G8 product containing 8 glucose residues but with a newly synthesized α-1,6 glycosidic linkage at the non-reducing end.

EXPERIMENTAL SECTION

Introduction

Glucansucrase (GS) (or glucosyltransferase; GTF) enzymes (EC 2.4.1.5) of lactic acid bacteria (LAB) use sucrose to synthesize a diversity of α-glucans with (α1→6) [dextran, mainly found in *Leuconostoc*], (α1→3) [mutan, mainly found in *Streptococcus*], alternating (α1→3) and (α1→6) [alternan, only reported in *Leuconostoc mesenteroides*], (α1→4) [reuteran, by GTFA and GTFO from *Lactobacillus reuteri* strains] glucosidic bonds {Monchois, 1999; van Hijum, 2006; Arguello-Morales, 2000; Kralj, 2002; Kralj, 2005}.

*Lactobacillus reuteri* 121 uses the glucansucrase GTFA and sucrose as substrate to synthesize a reuteran product with large amounts of (α1→4) glucosidic linkages. Upstream of this gtfA gene another putative glucansucrase gene was identified designated gtfB. Previously it has been shown that after cloning and expression of this gene the enzyme showed no activity on sucrose as substrate. Also in the genome of *L. reuteri* ML1 the putative catalytic and C-terminal domain of a gtfB homolog, gtfML4, was identified upstream of gtfML1 encoding a mutansucrase {Kralj, 2004}. In the recently elucidated genome sequence of *L. reuteri* DSM 20016 also a GTFB homolog could be identified (73% identity 85% similarity in 883 amino acids). Furthermore, also *L. reuteri* TMW1.106 contains besides a GTFA homolog (GTFA106) a GTFB homolog (GTFB106). This enzyme showed 92% identity and 95% similarity in 1383 amino acids with GTFB from *L. reuteri* 121. However, in contrast to GTFB, GTF106B showed low (after 27 h of incubation) hydrolyzing activity on sucrose {Kaditzky, 2008}.

It is shown herein that GTFB has a disproportionation type and polymerizing type of activity on malto-oligosaccharides. The enzyme uses malto-oligosaccharides (containing only (α1→4) glucosidic linkages) as substrate to synthesize oligosaccharides up to a degree of polymerization (DP) of 35. During this elongation/polymerization process large numbers of (α1→6) glucosidic linkages (~32%) are introduced in the final product. Furthermore, we show that with a large amylose substrate (Amylose-V) as donor and smaller saccharides (glucose, maltose) as acceptor also larger saccharides linked via (α1→4) glucosidic linkages are synthesized containing more than five glucose units. Detailed analysis of the product synthesized from maltoheptaose by methylation analysis and 1H NMR showed that up to 32% of (α1→6) glucosidic linkages were introduced in the final product. Although the primary structure of GTFB is similar to GH70 enzymes, including the permuted $(\beta/\alpha)_8$ barrel, its activity resembles more the GH13 α-amylase type of enzymes using malto-oligosaccharides as preferred substrate.

Materials and Methods

Bacterial strains, plasmids, media and growth conditions. *Escherichia coli* TOP 10 (Invitrogen, Carlsbad, Calif.) was used as host for cloning purposes. Plasmids pET15b (Novagen, Madison, Wis.) was used for expression of the (mutant) gtfB genes in *E. coli* BL21 Star (DE3). (Invitrogen). *E. coli* strains were grown aerobically at 37° C. in LB medium {Ausubel, 1987}. *E. coli* strains containing recombinant plasmids were cultivated in LB medium with 100 μg ml$^{-1}$ ampicillin. Agar plates were made by adding 1.5% agar to the LB medium.

Amino acid sequence alignment of GTFB from *L. reuteri*. Multiple amino acid sequence alignments of GTFB and known glucansucrases and putative α-glucanotransferases from lactic acid bacteria were made with the ClustalW interface in MEGA version 4 with gap-opening and extension penalties of 10 and 0.2, respectively.

Molecular techniques. General procedures for gene cloning, *E. coli* DNA transformations, DNA manipulations, and agarose gel electrophoresis were as described {Sambrook, 1989}. Restriction endonuclease digestions and ligations with T4 DNA ligase were performed as recommended by the enzyme suppliers (New England Biolabs, Beverly, Mass.; Roche Biochemicals, Basel, Switzerland). Primers were obtained from Eurogentec, Seraing, Belgium. Sequencing was performed by GATC (Konstanz, Germany). DNA was amplified by PCR on a DNA Thermal Cycler PTC-200 (MJ Research, Waltham, Mass.) using Pwo DNA polymerase (Roche Biochemicals) or Expand High Fidelity polymerase (Fermentas). Plasmid DNA of *E. coli* was isolated using a Wizard Plus SV plasmid extraction kit (Sigma)

Construction of plasmids. Appropriate primer pairs and template DNA were used to create two different expression constructs with a C-terminal His-tag: for the complete GTFB (1587 amino acids), constructed using three separate PCR reactions using the method previously described for GTFA from *Lb. reuteri* 121 (see below){Kralj, 2002}, and an N-terminally truncated variant (without N-terminal) variable region of GTFB (889 amino acids).

To facilitate future mutagenesis and nucleotide sequencing, gtfB was divided and cloned in three parts. The first of the two PstI restriction sites (1385 bp, 1751 bp) was altered, using the megaprimer method {Sarkar, 1990} and the following primers: BpstI for 5'-GTAAGTCGTTACTCAGCA-GATGCTAATGG-3' (SEQ ID NO. 5) containing a mutated PstI restriction site (underlined, silent mutation by change of base shown in bold face), and, BpstI rev 5'-GGTCAG-TAAATCCACCGTTATTAATTGG-3'. (SEQ ID NO. 6) In a subsequent PCR reaction the amplified product (420 bp) was used as (reverse) primer together with Bfor: 5'-GCAATT-GTCGACCATGGATACAAATACTGGTGATCAG-CAAACTGAACA-GG-3' (SEQ ID NO. 7) containing SalI (italics) and NcoI (bold) restriction sites. The resulting product of 1700 bp was digested with SalI and PstI and ligated in the corresponding sites of pBluescript II SK$^+$, yielding pBSP1600. The amplified 420 by product was also used as a forward primer together with BrevBamHI 5'-GGACTGTTATCACTATTATTATTTCCGGCC-3' (SEQ ID NO. 8) 70 bp downstream of a BamHI restriction site. The resulting product of (—4500 bp) was digested with Pst1 and BamHI and ligated in the corresponding sites of pBluescript II SK$^+$, yielding pBPB1000. The third fragment was obtained using primers BforBamHI 5'-CGCTATGTAATT-GAACAGAGTATTGCTGC-3' (SEQ ID NO. 9) 200 bp downstream of a BamHI restriction site and BRevHis 5'-CCTCCTTTCTAGATCTATTAGTGATGGTGATGGT-GATGGTTGTTAAAGTTTAATG AAATTGCAGTTGG-3' (SEQ ID NO. 10) containing XbaI (italics) and BglI (bold) and a 6×histidine tag (underlined). The resulting product of 2300 bp was digested with BamHI and XbaI and ligated in the corresponding sites of pBluescript II SK+, yielding pBBX2300. The complete gene was assembled as follows: pBPB1000 was digested with PstI and BamHI and the resulting fragment was ligated into pBSP1600 restricted with the same restriction enzymes yielding pBSB2600 (containing the first and second fragment). Subsequently, plasmid pBBX2300 was digested with BamHI and SacII (present on the plasmid, used instead of XbaI) and the fragment was ligated into pBSB2600 yielding pBSS4900 containing the full length gtfB gene. This plasmid was digested with NcoI and BglII and the gtfB gene was ligated in the NcoI and BamHI sites of pET15b, yielding pET15B-GTFB.

Expression and purification of GTFB. An overnight culture of *E. coli* BL21star (DE3) harbouring (mutant) GTFB {Kralj, 2004} was diluted 1/100. Cells were grown to OD$_{600}$ 0.4 and induced with 0.2 mM IPTG, after 4 h of growth cells were harvested by centrifugation (10 mM at 4° C. at 10,000×g). Proteins were extracted by sonication and purified by Ni-NTA and anion exchange chromatography as described previously for the GTFA (reuteransucrase) from *Lactobacillus reuteri* 121 {Kralj, 2004}, with the following modification: for anion exchange chromatography a 1 ml Hi-trap™Q HP column was used (Ge Healthcare).

(i) pH and temperature optima. pH and temperature optima were determined by measuring qualitatively on TLC the amount of oligo- and polysaccharides synthesized from 25 mM maltotetraose after overnight incubation (data not shown).

(ii) Products synthesized from malto-oligosaccharides and other saccharides. Single substrate incubations 90 nM GTFB and 25 mM of sucrose (Acros), raffinose (Sigma), turanose (Sigma), palatinose (Sigma), panose (Sigma), 0.25% Amylose-V (Avebe, Foxhol, The Netherlands), 0.25% amylopectin, 25 mM isomaltopentaose, isomaltohexaose (sigma), malto-oligosaccharides with a different degree of polymerization (G2-G7) were incubated separately overnight in 25 mM NaAc pH 4.7 1 mM CaCl$_2$ at 37° C. and analysed by TLC. Products synthesized from G6 and G7 over time were analyzed by TLC and HPAEC.

Acceptor/donor studies. 90 nM GTFB and 25 mM of glucose and malto-oligosaccharides with a different degree of polymerization (G2-G7) were incubated overnight together with 0.25% amylose-V in 25 mM NaAc pH 4.7 1 mM CaCl$_2$ at 37° C. and analysed by TLC.

(i) Characterization of the oligosaccharides and polysaccharides produced from G7. Purified GTFB enzyme preparations (90 nM) were incubated for 7 days with 150 mM G7 (sigma), using the conditions described above under enzyme assays. Oligo- and polysaccharides produced by purified recombinant GTFB were separated by precipitation with 96% ethanol (most of the larger saccharide product precipitates) {van Geel-Schutten, 1999}.

(ii) Methylation analysis. Oligo- and polysaccharides were permethylated using methyl iodide and dimesyl sodium (CH$_3$SOCH$_2$—Na$^+$) in DMSO at room temperature {Kralj, 2004}

Results

Alignment of GTFB

GTFB is the first representative of a group of homologues enzymes identified in different Lactobacilli. Alignments of members of this novel group of enzymes with other glucansucrases showed similarities but also some characteristics differences. The three catalytic residues present (D1024, E1061 and D1133 GTFA *L. reuteri* 121 numbering used throughout unless indicated otherwise) in glucansucrases are also present in the group of α-glucanotransferases (D1015, E1053 and D1125 GTFB *L. reuteri* 121 numbering. Nevertheless, a large number of amino acid residues conserved in glucansucrase in region I, II, III and IV are absent in the α-glucanotransferase group of enzymes (FIG. 1). In region II (encompassing the putative nucleophilic residue) the conserved V1025 (Pro in GTFA and GTFO) is substituted by an alanine in the α-glucanotransferases. Region III, the region downstream of the putative acid/base catalyst E1061 is completely different between the glucansucrases and the α-glucanotransferases.

Nevertheless, a large number of amino acid residues conserved in glucansucrase in region I, II, III and IV are absent in the α-glucanotransferase group of enzymes (FIG. 1). In region II (encompassing the putative nucleophilic residue) the conserved P1025 (Pro in GTFA and GTFO, Val in most GTFs) is substituted by a alanine in the α-glucanotransferases. Region III, the region downstream of the putative acid/base catalyst E1061 is completely different between the glucansucrases and the α-glucanotransferases. The conserved tryptophan 1063 is substituted by a tyrosine residue in the α-glucanotransferases (FIG. 1). In region IV the GTFB homologues contain a gap immediately upstream of the location of the Q1137 residue and at the position of the conserved glutamine a lysine residue is present.

GTFB Homologs

Gene and protein sequence databank searches showed several sequences that may have the same catalytic activity as GTFB. The info is based on a phylogenetic tree of all glycoside hydrolase family 70 members (108 sequences as available in the Pfam database on 27 Apr. 2010). Also the phylogenetic tree is available from the Pfam server, see FIG. 2.

TABLE 2

Glycoside hydrolase family 70 sequences from the Pfam database (http://pfam.sanger.ac.uk) with clear similarity to GTFB, apparent from the alignments and phylogenetic trees.

|  | UniProt entry | Microorganism |
|---|---|---|
| 1 | B1YMN6[1] | *Exiguobacterium sibiricum* 255-15 |
| 2 | C0X0D3 | *Lactobacillus fermentum* ATCC 14931 |
| 3 | C2F8B9 | *Lactobacillus reuteri* MM4-1 |
| 4 | C0YXW9 | *Lactobacillus reuteri* MM2-3 |
| 5 | A5VL73 | *Lactobacillus reuteri* DSM 20016 |
| 6 | B2G8K2 | *Lactobacillus reuteri* JCM 1112 |
| 7 | B7U9D3 | *Weissella confusa* MBF8-1 |
| 8 | A9Q0J0 | *Lactobacillus reuteri* TMW1.106 |
| 9 | Q5SBM0 | GTFB (*Lactobacillus reuteri* 121) |
| 10 | Q5SBN1 | *Lactobacillus reuteri* ML1 |
| 11 | Q9R4L7[2] | *Leuconostoc mesenteroides* |
| 12 | B1YMN6[1] | *Exiguobacterium sibiricum* 255-15 |

Note that no. 9 is GTFB and that the numbers follow the order as seen in the phylogenetic tree of FIG. 2.
[1]This sequence is listed twice in the table since two fragments of this sequence are in the tree.
[2]The apparent sequence similarity of number 11 is based on 20 amino acids only. This sequence is therefore ignored.

Of the nine GTFB-like sequences, the putative dextransucrase from *Lactobacillus reuteri* DSM 20016 (nr. 5 in the table) was cloned and expressed in *Escherichia coli*. The recombinant protein was purified by a combination of affinity and anion exchange chromatography. The purified protein showed GTFB-like activity when incubated with malto-oligosaccharides. The putative dextransucrase from *Lactobacillus reuteri* DSM 20016 showed no activity with sucrose, instead it uses maltose, maltotriose, maltotetraose, maltopentaose, maltohexaose and maltoheptaose as substrate producing a ladder of shorter and longer products. Proton-NMR analysis of the products demonstrated that α-1,6-glycosidic bonds were introduced, as also seen for the GTFB incubations. Moreover, the putative dextransucrase from *Lactobacillus reuteri* DSM 20016 also increased the percentage of α-1,6-glycosidic bonds in soluble potato starch of Sigma-Aldrich.

Cloning and Expression of GTFB

The full length, N-terminal truncated version and putative nucleophilic mutant of GTFB were constructed and expressed successfully. Both the full length as well as the N-terminal truncated variant showed clear activity on malto-oligosacharides as measured by TLC (data not shown). The constructed truncated GTFB version (GTFB-ΔN) was not expressed as efficiently as the full length GTFB and therefore all experiments were performed using full length GTFB. To rule out any background activity emerging from *E. coli* itself, an empty pET15b plasmid was purified, and already after His-tag purification no activity on malto-oligosaccharides (G2-G7) was detected (data not shown). Furthermore, the purified full length D1015N (putative) nucleophilic mutant showed no activity on malto-oligosaccharides (G2-G7; data not shown).

Enzyme Characteristics

The optimal activity for GTFB with maltotetraose as a substrate as determined qualitatively by TLC was at a temperature of 30-37° C. and a pH of 4-5 (data not shown). Combinations of different temperatures and pH buffers indicated optimal activity at a temperature of 37° C. and a pH of 4.7, which was used in all subsequent assays.

Donor Substrates

Since it had already been shown that GTFB is not able to use sucrose as donor substrate {Kralj, 2004}, different sucrose analogues (turanose, palatinose) and raffinose were tested for activity. We were not able to detect activity on any of these substrates (data not shown). Also no activity was observed on isomalto-oligosaccharides (IG5 and IG6) substrates (data not shown). Activity on oligosaccharides derived from a partially purified reuteran (GTFA) hydrolysate or panose was also not detected (data not shown). However, on linear malto-oligosaccharides clear activity was observed already after short incubation times. Especially on malto-oligosaccharides with a degree of polymerization of 4 and larger, different oligosaccharides were synthesized (FIG. 3). From a DP of 6 and larger, besides oligosaccharides also larger polymeric material started to accumulate. On amylose-V (Avebe, Foxhol, The Netherlands) also low activity (mainly G1 and G2 release) was observed (FIG. 5). On maltose alone virtually no activity was observed. However, when amylose-V was incubated simultaneously with glucose or maltose a range of oligosaccharides were synthesized (FIG. 5). Using amylose-V as donor and glucose as acceptor larger numbers of maltose were synthesized compared to incubation on amylose-V alone, indicating (α1→4) synthesizing capability. On amylose-V alone virtually no G3 was released. Incubation of amylose-V with maltose as acceptor clearly yielded panose and G3 indicating GTFB capability to besides panose (indicating (α1→6) synthesizing capability) also maltotriose was synthesized demonstrating the enzyme capability to synthesize (α1→4) glucosidic linkages.

Product Characterization in Time on G6 and G7

Figure 4:
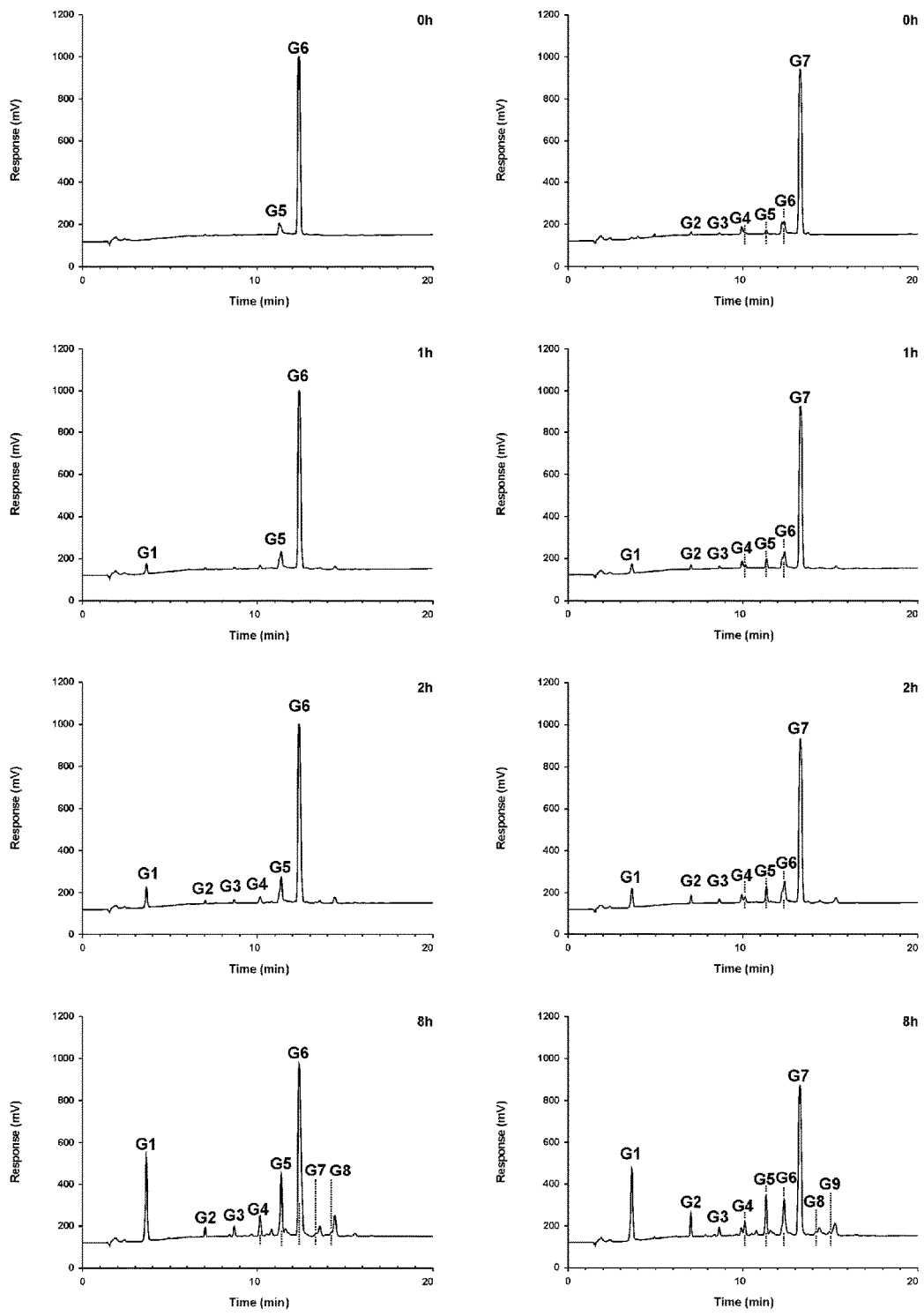

The first reaction products detectable on G6 were G1 (glucose) and G5 (maltopentaose) (FIG. 4). Also on G7 the first products released were G1 (glucose) and G6 (maltohexaose). Later in time on G6 also other malto-oligosaccharides such as G2, G3 and G4 appeared. Also unknown saccharides next to G7 and G8 were identified, which besides (α1→4) glucosidic linkages also must contain other linkages indicated by the shift in their retention time.

After incubation of maltoheptaose with GTFB for 120 h, the 1D $^1$H-NMR spectrum of the total product mixture (FIG. 7) indicated the presence of newly formed (α1→6) linkages by a broad signal at $\delta_{H-1}$~4.96. The (α1→4) signal is present at $\delta_{H-1}$~5.39. After 120 h of incubation, the ratio (α1→4):(α1→6) is 67:33 in the product mixture. MALDI-TOF MS analysis of the product mixture revealed the presence of compounds ranging from DP2 up to DP35 (m/z 365-m/z 5711, [M+Na]$^+$).

In the reaction mixture obtained from incubation of MOS DP7 with recombinant GFTB, seventeen different structures (FIG. 6), ranging from DP2-DP10, could be elucidated in detail by NMR spectroscopy. The elucidated structures constitute only a part of the total number of compounds that were formed. More high molecular mass products are present, including polysaccharides. It is clear that the oligosaccharides smaller than DP7 must be stemming from hydrolysis activity of GTFB on the substrate [products containing (α1→4) only] as well as from hydrolysis activity on the formed oligosaccharides [products containing (α1→4) and (α1→6)]. It has to be noted that no structures were found having a 6-substituted reducing-end glucose residue. Until now, only one structure (DP8) was found having a (α1→6)-linked glucose residue elongated by successive (α1→4)-linked glucose residues. In the other cases, only (successive) (α1→6) elongation has occurred. All oligosaccharides have a 4-substituted glucose residue at the reducing end. However, in the 1D $^1$H NMR spectrum (FIG. 7) of the total product mixture a trace of a terminal reducing-(1→)-D-Glc unit was found (H-1α at δ 5.240 and H-1β at δ 4.669), but this unit was not found in the elucidated structures.

Thus, recombinant GTFB catalyzes the cleavage of only (α1→4) linkages and initiates formation of new (α1→4) and (α1→6) bonds. In this way, many products are formed, ranging from monosaccharide to polysaccharide (DP>30). Different structures for a single-molecular-mass product are possible, as is shown clearly for the formed DP7- and DP8-oligosaccharides(-alditols). Furthermore, it was observed that the amount of (α1→6) bonds compared to (α1→4) bonds increases with increasing chain length, to a maximum of 50:50. No 4,6- or other types of branching points are introduced. The fact that the recombinant GTFB enzyme showed similar activities on the free malto-oligosaccharides as well as on their reduced forms (malto-oligosaccharide-alditols), demonstrates a non-reducing end elongation mechanism.

Important conclusions which can be drawn from the above results are the following:
- no structures were found having a 6-substituted reducing-end glucose residue;
- GTFB catalyzes the cleavage of only (α1→4) linkages and initiates formation of new (α1→4) and (α1→6) bonds;
- the amount of (α1→6) bonds compared to (α1→4) bonds increases with increasing chain length, to a maximum of 50:50.
- no 4,6- or other types of branching points are introduced;
- GTFB has a non-reducing end elongation mechanism.

Introducing GTFB Like Activity in GTFA Via Protein Engineering

Previous protein engineering studies have demonstrated that amino acid residues located in conserved sequence region III and IV (see FIG. 1 for a sequence alignment) control the product specificity of GTF enzymes regarding the glycosidic bonding type formed. Also region I and region II contain amino acid residues that contribute to enzyme activity and reaction specificity. The amino acid residues of the conserved sequence regions form part of the acceptor substrate binding region of GTF enzymes. In the polymerization reaction using sucrose as substrate these residues interact with the glucose (subsite-1) and fructose (subsite+1) moiety of sucrose. As GTFB utilizes maltoheptaose (and other malto-oligosaccharides) as substrate a glucose moiety will interact at the acceptor subsites in the GTFB enzyme. The unique substrate specificity of GTFB compared to the traditional GTFs is therefore most likely determined by differences at the acceptor subsites. Thus, to introduce GTFB-like activity in a traditional GTFA enzyme it is envisaged to substitute residues at the acceptor subsites, located in the regions I, II, III and IV, to resemble the sequence of the GTFB enzyme.

Furthermore, the 3D structure of GTF180 (Vujicic, PhD thesis University of Groningen) shows some additional residues interacting at subsites −1 and +1 that are likely important for the interconversion of reaction specificity of GTFs. The 981 L→V mutations is based on an interaction seen in the 3D structure of GTF180, where Leu981 has a Van Der Waals interaction with the fructosyl moiety of sucrose. In GTFB this position is occupied by a valine residue as well as in the other α-glucanotransferases GTFDSM, GTF106B, GTFML4. The 1463 D→R, T or M mutations are aimed at substituting the aspartate residue, which is highly conserved in glucansucrases, but not in GTFB and the related enzymes, and interacts with the glucose moiety at subsite −1 in GTF180 3D structure.

Additionally, the mutations may be combined in any manner to obtain a stronger effect in alteration of the reaction specificity GTF enzymes. The proposed mutations are as follows:

Region I
position W1510:W→I/L
position P1512:P→
position D1513:D→N
Region II
position 1026: P→A
Region III
position 1062: D→G
position 1063: W→Y
position 1064: N→H
position 1062-1064 DWN→GYH
Region IV
position 1134: N→Q
position 1135: N→R
position 1136: S→delete this residue
position 1134-1136: NNS→QR
position 1137:Q→K
3D structure
position 981: L→V
position 1414: N→L
position 1463: D→R, T or M

REFERENCES

Arguello-Morales M A, Remaud-Simeon M, Pizzut S, Sarcabal P & Monsan P (2000) *FEMS Microbiol. Lett.* 182, 81-85.

Ausubel, F. M., Brent, R. E., Kingston, D. D., Moore, J. G., Seidman, J. G., Smith, J. A., & Struhl, K. (1987) *Current protocols in molecular biology*. John Wiley & Sons, Inc, New York.

Barends T R, Bultema J B, Kaper T, van der Maarel M J, Dijkhuizen L & Dijkstra B W (2007) *J. Biol. Chem.* 282, 17242-17249.

Fabre E, Bozonnet S, Arcache A, Willemot R M, Vignon M, Monsan P & Remaud-Simeon M (2005) *J. Bacteriol.* 187, 296-303.

van Geel-Schutten G H, Faber E J, Smit E, Bonting K, Smith M R, Ten Brink B, Kamerling J P, Vliegenthart J F & Dijkhuizen L (1999) *Appl. Environ. Microbiol.* 65, 3008-3014.

Hard K, Van Z G, Moonen P, Kamerling J P & Vliegenthart F G (1992). *Eur. J. Biochem.* 209, 895-915.

Hondoh H, Kuriki T & Matsuura Y (2003) *J. Mol. Biol.* 326, 177-188.

van Hijum S A, Kralj S, Ozimek L K, Dijkhuizen L & van Geel-Schutten IG (2006). *Microbiol. Mol. Biol. Rev.* 70, 157-176.

Kaditzky, S., Behr, J., Stocker, A., Kaden, P., & Vogel, R. F. Food Biotechnol. 22[4], 398-418. 2008.

Kamerling, J. P. & Vliegenthart, J. F. (1989) Mass Spectrometry. In Clinical Biochemistry—Principles, Methods, Applications. (Lawson, A. M., ed), pp. 176-263. Walter de Gruyter, Berlin.

Kelly R M, Dijkhuizen L & Leemhuis H (2009). *J. Biotechnol.* 140, 184-193

Kralj S, van Geel-Schutten G H, Rahaoui H, Leer R J, Faber E J, van der Maarel M J & Dijkhuizen L (2002) *Appl. Environ. Microbiol.* 68, 4283-4291.

Kralj S, van Geel-Schutten G H, van der Maarel M J & Dijkhuizen L (2003). *Biocatal. Biotransform.* 21, 181-187.

Kralj S, van Geel-Schutten G H, Dondorff M M, Kirsanovs S, van der Maarel M J & Dijkhuizen L (2004) *Microbiology* 150, 3681-3690.

Kralj S, van Geel-Schutten G H, van der Maarel M J & Dijkhuizen L (2004) *Microbiology* 150, 2099-2112.

Kralj S, Stripling E, Sanders P, van Geel-Schutten G H & Dijkhuizen L (2005). *Appl. Environ. Microbiol.* 71, 3942-3950.

van Leeuwen S S, Kralj S, van Geel-Schutten I H, Gerwig G J, Dijkhuizen L & Kamerling J P (2008) *Carbohydr. Res.* 343, 1237-1250.

van Leeuwen S S, Kralj S, van Geel-Schutten I H, Gerwig G J, Dijkhuizen L & Kamerling J P (2008) *Carbohydr. Res.* 343, 1251-1265.

van Leeuwen S S, Leeflang B R, Gerwig G J & Kamerling J P (2008) *Carbohydr. Res.* 343, 1114-1119.

Linden A, Mayans O., Meyer-Klaucke W, Antranikian G & Wilmanns M (2003). *J. Biol. Chem.* 278, 9875-9884.

MacGregor E A, Jespersen H M & Svensson B (1996) *FEBS Lett.* 378, 263-266.

MacGregor E A, Janecek S & Svensson B (2001) *Biochim. Biophys. Acta* 1546, 1-20.

Monchois V, Willemot R M & Monsan P (1999) *FEMS Microbiol. Rev.* 23, 131-151.

Moore A D, Bjorklund A K, Ekman D, Bornberg-Bauer E & Elofsson A (2008). *Trends Biochem. Sci.* 33, 444-451.

Peisajovich S G, Rockah L & Tawfik D S (2006) *Nat. Genet.* 38, 168-174.

Pijning T, Vuijičić-Žagar A, Kralj S, Eeuwema W, Dijkstra BW & Dijkhuizen L (2008). *J. Biocatal. Biotransform.* 26, 12-17.

Przylas I, Tomoo K, Terada Y, Takaha T, Fujii K, Saenger W & Strater N (2000) *J. Mol. Biol.* 296, 873-886.

Rondeau-Mouro C, Veronese G & Buleon A (2006) *Biomacromolecules.* 7, 2455-2460.

Sambrook, J., Fritsch, E. F., & Maniates, T. (1989) *Molecular cloning: a laboratory manual,* 2 edn. Cold Spring Harbor Laboratory Press, New York.

Sarkar G & Sommer S S (1990). *Biotechniques* 8, 404-407.

Stam M R, Danchin E G, Rancurel C, Coutinho P M & Henrissat B (2006) *Protein Eng Des Sel.* 19, 555-562.

Tokuriki N & Tawfik D S (2009). *Science.* 324, 203-207.

Uitdehaag J C, Mosi R, Kalk K H, van der Veen B A, Dijkhuizen L, Withers S G & Dijkstra B W (1999) *Nat. Struct. Biol.* 6, 432-436.

Vuijičić-Žagar, A. 2007. University of Groningen. PhD Thesis/Dissertation

---

The invention claimed is:

1. A method for producing a mixture of gluco-oligosaccharides having one or more consecutive (α1→6) glucosidic linkages and one or more consecutive (α1→4) glucosidic linkages, comprising contacting a poly- and/or oligosaccharide substrate comprising at its non-reducing end at least two α1→4-linked D-glucose units with an α-glucanotransferase enzyme capable of cleaving (α1→4) glucosidic linkages and making new (α1→4) and (α1→6) glucosidic linkages, wherein said α-glucanotransferase enzyme comprises a polypeptide sequence having at least 60% identity to the catalytic core of α-glucanotransferase enzyme GTFB from Lactobacillus reuteri 121(SEQ ID NO. 59), wherein the α-glucanotransferase does not introduce (α1→6) branching points.

2. The method according to claim 1, wherein said α-glucanotransferase does not introduce (α1→6) branching points nor (α1→2) or (α1→3) linkages.

3. The method according to claim 1, wherein said α-glucanotransferase is from the GH70 glycoside hydrolase family.

4. The method according to claim 1, wherein said α-glucanotransferase is selected from the group consisting of GTFB from Lactobacillus reuteri 121(SEQ ID NO. 59), GTF106B from Lactobacillus reuteri TMW 1.106(SEQ ID NO. 61), GTML4 from Lactobacillus reuteri ML1 (SEQ ID NO. 63), GTFDSM from Lactobacillus reuteri DSM 20016$^4$ (SEQ ID NO. 65), and GTF from Lactobacillus fermentum ATCC 14931 (SEQ ID NO. 67).

5. The method according to claim 1, wherein said substrate has a degree of polymerization of at least 4.

6. Method according to claim 1, wherein said substrate is selected from the group consisting of starch, waxy starch, high amylose starch, their derivatives, malto-oligosaccharides, amylose, amylopectin, maltodextrins, (α1→4) glucans, reuteran, or combinations thereof.

7. Method according to claim 6, wherein said starch, waxy starch, high amylose starch or starch derivative is derived from potato, maize, tapioca, pea, mung bean, rice or wheat.

8. Method according to claim 6, wherein said starch derivative is produced by treating starch, waxy starch or high amylose starch with amylomaltase/4-alpha-glucanotransferase or glycogen -branching enzyme.

9. The method according to claim 1, further comprising the step of isolating from the mixture at least one gluco-oligosaccharides having one or more consecutive (α1→6) glucosidic linkages and one or more consecutive (α1→4) glucosidic linkages.

10. The method according to claim 9, wherein said isolation comprises at least one of precipitation-fractionation and chromatography.

11. The method according to claim 1, wherein said α-glucanotransferase enzyme comprises at least one conserved amino acid residue selected from the group consisting of Asp1015, Glu1053, and Asp1125 of GTFB of Lactobacillus reuteri 121(SEQ ID NO. 59), and equivalent residues in-homologous α-glucanotransferase enzymes selected from the group consisting of GTF106B from Lactobacillus reuteri TMW 1.106(SEQ ID NO. 61), GTML4 from Lactobacillus reuteri ML1 (SEQ ID NO. 63), GTFDSM from Lactobacillus reuteri DSM 20016$^4$(SEQ ID NO. 65), and GTF from Lactobacillus fermentum ATCC 14931 (SEQ ID NO. 67).

12. The method according to claim 1, wherein said substrate has a degree of polymerization of at least 6.

13. The method according to claim 1, wherein said α-glucanotransferase enzyme comprises at least three conserved amino acid residues selected from the group consisting of Arg1013, Asp1015, Ala1017, Asn1019, Glu1053, Gly1054, Tyr1055, His1124, Asp1125, Gln1126, Arg1127, Lys1128, Asp1479, Ile1480, Met1482, Asn1483, and Gln1484 of GTFB of Lactobacillus reuteri 121 (SEQ ID NO. 59), and equivalent residues in homologous α-glucanotransferase enzymes selected from the group consisting of GTF106B from Lactobacillus reuteri TMW 1.106(SEQ ID NO. 61), GTML4 from Lactobacillus reuteri ML1 (SEQ ID NO. 63), GTFDSM from Lactobacillus reuteri DSM 20016$^4$ (SEQ ID NO. 65), and GTF from Lactobacillus fermentum ATCC 14931 (SEQ ID NO. 67).

14. The method according to claim 1, wherein said α-glucanotransferase enzyme comprises Asp1015, Glu1053, and Asp1125 of GTFB of Lactobacillus reuteri 121(SEQ ID NO. 59), or equivalent residues in homologous α-glucanotransferase enzymes selected from the group consisting of GTF106B from Lactobacillus reuteri TMW 1.106(SEQ ID NO. 61), GTML4 from Lactobacillus reuteri ML1 (SEQ ID NO. 63), GTFDSM from Lactobacillus reuteri DSM 20016$^4$ (SEQ ID NO. 65), and GTF from Lactobacillus fermentum ATCC 14931 (SEQ ID NO. 67).

15. The method according to claim 1, wherein said α-glucanotransferase enzyme comprises Arg1013, Asp1015, Ala1017, Asn1019, Glu1053, Gly1054, Tyr1055, His1124, Asp1125, Gln1126, Arg1127, Lys1128, Asp1479, Ile1480, Met1482, Asn1483, and Gln1484 of GTFB of Lactobacillus reuteri 121(SEQ ID NO. 59); or equivalent residues in homologous α-glucanotransferase enzymes selected from the group consisting of GTF106B from Lactobacillus reuteri TMW 1.106(SEQ ID NO. 61), GTML4 from Lactobacillus reuteri ML1 (SEQ ID NO. 63), GTFDSM from Lactobacillus reuteri DSM 20016$^4$(SEQ ID NO. 65), and GTF from Lactobacillus fermentum ATCC 14931 (SEQ ID NO. 67).

16. The method according to claim 1, wherein the catalytic core of GTFB from Lactobacillus reuteri 121 comprises SEQ ID NO. 60.

17. A method for producing starch derivatives or partially indigestible starch derivatives comprising contacting an enzyme capable of cleaving (α1→4) glucosidic linkages and making new (α1→4) and (α1→6) glucosidic linkages, and/or transferring a maltose, maltotriose or maltotetraosyl-unit making a new (α1→6) glucosidic linkage with a sequence having at least 60% identity to the catalytic core of an α-glucanotransferase enzyme selected from the group consisting of GTFB from Lactobacillus reuteri 121(SEQ ID NO. 59).

* * * * *